(12) United States Patent
Yanofsky

(10) Patent No.: US 7,485,772 B2
(45) Date of Patent: Feb. 3, 2009

(54) METHODS OF SUPPRESSING FLOWERING IN TRANSGENIC PLANTS

(75) Inventor: Martin F. Yanofsky, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 308 days.

(21) Appl. No.: 11/241,551

(22) Filed: Sep. 29, 2005

(65) Prior Publication Data

US 2006/0070142 A1 Mar. 30, 2006

Related U.S. Application Data

(62) Division of application No. 09/869,582, filed as application No. PCT/US99/24407 on Oct. 15, 1999, now Pat. No. 6,987,214.

(60) Provisional application No. 60/104,604, filed on Oct. 16, 1998.

(51) Int. Cl.
*C12N 15/29* (2006.01)
*C12N 15/82* (2006.01)
*A01H 5/00* (2006.01)

(52) U.S. Cl. ............... 800/278; 800/298; 800/287; 800/294; 536/24.1

(58) Field of Classification Search ............ None
See application file for complete search history.

(56) References Cited

U.S. PATENT DOCUMENTS 5,554,798 A  9/1996  Lundquist

FOREIGN PATENT DOCUMENTS

WO  WO 97/27287  7/1997
WO  WO 98/13503  4/1998

OTHER PUBLICATIONS

Kagaya et al (1995, Mol. Gen. Genet. 248 :668-674).*
Benfey et al (1990, Science 250:959-966).*
Benfey et al (1989, EMBO J, 8(8):2195-2202.*
Day et al (1995, Development 121:2887-2895.*
Ma et al (1991, Genes and Development 5:484-495.*
Hempel, Frederick D. et al.; "Floral determination and expression of floral regulatory genes in *Arabidopsis*"; 1997, Development, vol. 124, pp. 3845-3853.
Nilsson, Ove et al.; "Genetic ablation of flowers in transgenic *Arabidopsis*"; 1998, The Plant Journal, vol. 15, No. 6, pp. 799-804.
Izawa, et al., "Plant bZIP Protein DNA Binding Specificity," 1993, J.Mol.Biol. 230, pp. 1131-1144.
Hao, et al,. "Unique Mode of GCC Box Recognition by the DNA-binding Domain of Ethylene-Responsive Element-Binding Factor (ERF Domain) in Plant," 1998, The J. of Biological Chemistry 273 (41), pp. 26857-26861.
Busch, et al., "Activation of a Floral Homeotic Gene in a *Arabidopsis*," 1999, Science, 285, pp. 585-587.
Lohmann, et al., "A Molecular Lind Between Stem Cell Regulation and Floral Patterning in *Arabidopsis*," 2001, Cell 105, pp. 793-803.
Benfey, et al., "The Cauliflower Mosaic Virus 35S Promoter: Combinatorial Regulation of Transcription in Plants," 1990 Science, 250, pp. 959-966.
Benfey, et al., "The CaMV 35S Enhancer Contains at Least Two Domains Which Can Confer Different Developmental and Tissue-Specific Expression Patters," 1989, EMBO J, 8(8), pp. 2195-2202.
Day, et al., "Genetic Ablation of Petal and Stamen Primordial to Elucidate Cell Interactions During Floral Development," 1995, Development 121, pp. 2887-2895.
Ma, et al., "AGL1-AGL6, an *Arabidopsis* gene family with similarity to floral homeotic and transcription factor genes"; Genes & Development vol. 5, No. 3, pp. 484-495 (Mar. 1991).
Palmiter, et al. "Cell Lineage Ablation in Transgenic Mice by Cell-specific Expression of a Toxin Gene"; Cell, vol. 50 pp. 435-443 (Jul. 1987).
Federspiel, et al. "*Arabidopsis thaliana* chromosome I BAC F316 genomic sequence, complete sequence" EMBL Sequence Database, (Aug. 1997) Heidelberg DE.
Mandel, et al. "*Arabidopsis thaliana* MADS-box (AGL9) mRNA, complete cds." EMBL Sequence Database (Aug. 1997) Heidelberg DE.
Rounsley, et al. "T33C10TF TAMU *Arabidopsis thaliana* genomic clone T33C10, genomic survey sequence" EMBL Sequence Database, (Apr. 1998) Heidelberg DE.

* cited by examiner

*Primary Examiner*—Stuart F. Baum
(74) *Attorney, Agent, or Firm*—Townsend and Townsend and Crew LLP

(57) ABSTRACT

The present invention provides a transgenic plant characterized by suppressed flowering. The transgenic plant contains a nucleic acid molecule including a floral organ selective regulatory element operatively linked to a nucleotide sequence encoding a cytotoxic gene product, wherein the nucleic acid molecule is heritable by progeny thereof.

17 Claims, 43 Drawing Sheets

Sequence Range: 1 to 4512

```
                                                                  50
          AGATCTCTAT GAAAAATGGC AAAATCAACA ATAATCCCTT GGCTATATGG TGGTATTTCT
          TCTAGAGATA CTTTTTACCG TTTTAGTTGT TATTAGGGAA CCGATATACC ACCATAAAGA

100
          GTTAAAAGTG ACTTATGGG AGATTTTTA GCTTCATAGA TTCTTGTCG AAAAAAAATT
          CAATTTTCAC TGAATACCCA TCTAAAAAAT CGAAGTATCT AAGAAACAGC TTTTTTTTAA

150
          ACTTTGTACA TTTTAGTGGA GTTATTTAAA TTTCCCAATT GAACAAAACC ATATATTGAT
          TGAAACATGT AAAATCACCT CAATAAATTT AAAGGGTTAA CTTGTTTTGG TATATAACTA

200
          GAAATTCGCA AATGCAATCC AAAAATAAAT ATGTTCCACT CTTTTGGTTA GCTTTTAACT
          CTTTAAGCGT TTACGTTAGG TTTTTATTTA TACAAGGTGA GAAAACCAAT CGAAAATTGA 250                                                300
          AAACATGCGT TTT------- TTCCAGCTAG TACGAGTCTC TATATATAAA CTTTCTTAAT
          TTTGTACGCA AAA------- AAGGTCGATC ATGCTCAGAG ATATATATTT GAAAGAATTA

350
          ATCGCTAACA ATTTACTTCA AGTTTGTAAT GTGATAAGTG AAAGACCGTA TATACATACA
          TAGCGATTGT TAAATGAAGT TCAAACATTA CACTATTCAC TTTCTGGCAT ATATGTATGT

400
          CATGTTAATC AACTGATAAC CTTTGTGCCT CGTGTGTCTA GTTACTAGTC AACCATCAAA
          GTACAATTAG TTGACTATTG GAAACACGGA GCACACAGAT CAATGATCAG TTGGTAGTTT

450
          CGTGCATGAT GCTGTTTTTC TTAGAGTACT ATTGTTGTGT TATATATAAC TAAACATAAA
          GCACGTACTA CGACAAAAAG AATCTCATGA TAACAACACA ATATATATTG ATTTGTATTT

500
          CAATTTGCTA TTATGATATA AACATAGAAT TTTCAAGCAA TGATATGTTT AGATGTTTTG
          GTTAAACGAT AATACTATAT TTGTATCTTA AAAGTTCGTT ACTATACAAA TCTACAAAAC 550                                          600
          TATAAATATT CCATAAATAG TAGACACCCA TATATACACA AACATGAATT CTACCTGAGG
          ATATTTATAA GGTATTTATC ATCTGTGGGT ATATATGTGT TTGTACTTAA GATGGACTCC

650
          AGAAACACAT AGATGTTCAA ATTAAATAAT AACCCTATAA TGAAAACTCT AAAGTAAGTA
          TCTTTGTGTA TCTACAAGTT TAATTTATTA TTGGGATATT ACTTTTGAGA TTTCATTCAT

700
          ATACGAAATA AAAATTTATC CTTTAAATAA CATATAACAT ATATATCAAC TTTAATTGGT
          TATGCTTTAT TTTTAAATAG GAAATTTATT GTATATTGTA TATATAGTTG AAATTAACCA

750
          AATTGTATCA CAAGAGCCAA TTATTTGGTG ACTGTATCAC ACGTGCTTAA AGAGAGCGTG
          TTAACATAGT GTTCTCGGTT AATAAACCAC TGACATAGTG TGCACGAATT TCTCTCGCAC

800
          GGAATGAAAG TAAAGAAGAA TAAAGAAGCA GAGAGATGGG CTAGAAATGA GAAAACACAC
          CCTTACTTTC ATTTCTTCTT ATTTCTTCGT CTCTCTACCC GATCTTTACT CTTTTGTGTG 850                                          900
          CAAACCCTAA CCTCACCCTC ACACATTTCT TATCTTTTGC TCTCAATAGA TTCCATTGAT
          GTTTGGGATT GGAGTGGGAG TGTGTAAAGA ATAGAAAACG AGAGTTATCT AAGGTAACTA
```

Fig. 1a

```
                                                       950
TCAAAACAAA ATTTTCATTA AGATTTCACA ACCTCCACAC ACTTCCAAAC ACAATTAAAG
AGTTTTGTTT TAAAAGTAAT TCTAAAGTGT TGGAGGTGTG TGAAGGTTTG TGTTAATTTC

1000
AGAGGAAAAA GAATCAATAA CCCTATAAAT AAAAAATCAG ACAAACAGAA GTTTCCTCTT
TCTCCTTTTT CTTAGTTATT GGGATATTTA TTTTTTAGTC TGTTTGTCTT CAAAGGAGAA

1050
CTTCTTCCTT AAGCTAGTAC CTTTTGTTCT TGAAATTAGG GTTAATTTCT TTTTTCCAAA
GAAGAAGGAA TTCGATCATG GAAAACAAGA ACTTTAATCC CAATTAAAGA AAAAAGGTTT

1100
TACCATCAAT TCTCCAGACC ATAAAAACTC AAAAAGATCA GATCTTTCCT CTGAAAAAGA
ATGGTAGTTA AGAGGTCTGG TATTTTTGAG TTTTTCTAGT CTAGAAAGGA GACTTTTTCT 1150                                                    1200
GATACCCAAC TTATGTTTTT GTGTGTCTGT ATATAGATAA ACATTACATA CCCATATTTG
CTATGGGTTG AATACAAAAA CACACAGACA TATATCTATT TGTAATGTAT GGGTATAAAC

1250
TGTATAGACA TAAAAAGTGG AAATTAAGGT AACAAAAAGA AATGGGAAGA GGAAGAGTAG
ACATATCTGT ATTTTTCACC TTTAATTCCA TTGTTTTTCT TTACCCTTCT CCTTCTCATC

1300
AGCTGAAGAG GATAGAGAAC AAAATCAACA GACAAGTAAC GTTTGCAAAG CGTAGGAACG
TCGACTTCTC CTATCTCTTG TTTTAGTTGT CTGTTCATTG CAAACGTTTC GCATCCTTGC

1350
GTTTGTTGAA GAAAGCTTAT GAATTGTCTG TTCTCTGTGA TGCTGAAGTT GCTCTCATCA
CAAACAACTT CTTTCGAATA CTTAACAGAC AAGAGACACT ACGACTTCAA CGAGAGTAGT

1400
TCTTCTCCAA CCGTGGAAAG CTCTATGAGT TTTGCAGCTC CTCAAAGTAA ACAACTCTCT
AGAAGAGGTT GGCACCTTTC GAGATACTCA AAACGTCGAG GAGTTTCATT TGTTGAGAGA 1450                                                    1500
CACTCTTTAT CAGTTTCTTG ATTGAGTTTT TGCTAGATCT GAGCTTAGAT CTTTGTCTCA
GTGAGAAATA GTCAAAGAAC TAACTCAAAA ACGATCTAGA CTCGAATCTA GAAACAGAGT

1550
AGGACTTGTT ATATATAGAT CACACGATCT TGATTTCTAC GAAGTTGAGT TAATTAGATT
TCCTGAACAA TATATATCTA GTGTGCTAGA ACTAAAGATG CTTCAACTCA ATTAATCTAA

1600
TCTTGATTTC ATTTTCTAGG GTTTTTTTCC AATTCTTGAA ATTTAAGATC TGGTTTTTTT
AGAACTAAAG TAAAAGATCC CAAAAAAAGG TTAAGAACTT TAAATTCTAG ACCAAAAAAA

1650
GTTGTCAATG ATTTAGAACT GTGAATTTTG TAATCGAATA GATTCCAAAT CCTGATATGC
CAACAGTTAC TAAATCTTGA CACTTAAAAC ATTAGCTTAT CTAAGGTTTA GGACTATACG

1700
AATCTGAAAA GTTTTATATA ATTAATATAT GTCTGTGTGA TTGGAAACTT AAAAGTTGGA
TTAGACTTTT CAAAATATAT TAATTATATA CAGACACACT AACCTTTGAA TTTTCAACCT 1750                                                 1800
ATCACAGATT TCTATGAAAA TTACAAGTAT CCAACGTAGA ATTGATAATA TATGGTTACA
TAGTGTCTAA AGATACTTTT AATGTTCATA GGTTGCATCT TAACTATTAT ATACCAATGT

1850
TGCATTAACC ATTTGTTAGT TCATCATACT TTATGGTGGT TAAAACTTCA AACGCGTGTA
```

Fig. 1b

```
ACGTAATTGG TAAACAATCA AGTAGTATGA AATACCACCA ATTTTGAAGT TTGCGCACAT
                              1900
TATCTATGAA GGCAAAGATT GTTTGTTTTT TCTTAAAAAC AATGTTTAAT AGATTTTTAA
ATAGATACTT CCGTTTCTAA CAAACAAAAA AGAATTTTTG TTACAAATTA TCTAAAAATT
                   1950
TTATATGTTA AAATAGTTTT GCTTACATGC ATTCAAGAAA ATATAGCGAT TAATTCCTTT
AATATACAAT TTTATCAAAA CGAATGTACG TAAGTTCTTT TATATCGCTA ATTAAGGAAA
              2000
TTTCAAATCA CAATTTGTGA ATCAAACGAA AACGTAAGAT ATTGCTTGCA AATGATAGGA
AAAGTTTAGT GTTAAACACT TAGTTTGCTT TTGCATTCTA TAACGAACGT TTACTATCCT
         2050                                             2100
TTGAACTATT GATATTTGTA AATATAAATA CGAAACTTTA CGTTTGAAAG TTGAAACAAT
AACTTGATAA CTATAAACAT TTATATTTAT GCTTTGAAAT GCAAACTTTC AACTTTGTTA
                                        2150
CAAATCCAAA TCAACTCGTA TATAATCAGA TAAATAATGG AAACAATCTT CAATTTTGAT
GTTTAGGTTT AGTGAGCAT ATATTAGTCT ATTTATTACC TTTGTTAGAA GTTAAAACTA
                              2200
GGAAGAATAC TTTAAAACTT GAAGAGCTTT TTTTTTTTAT GGTGATTTAT AGGTTTAGAT
CCTTCTTATG AAATTTTGAA CTTCTCGAAA AAAAAAAATA CCACTAAATA TCCAAATCTA
                    2250
CTCCAAAGTC AAGTATGATC TTTTTAATAA ACTCTTATTC TCTCTTTTTG AGTTATTTTC
GAGGTTTCAG TTCATACTAG AAAAATTATT TGAGAATAAG AGAGAAAAAC TCAATAAAAG
              2300
AGCATGCTCA AGACACTTGA TCGGTACCAG AAATGCAGCT ATGGATCCAT TGAAGTCAAC
TCGTACGAGT TCTGTGAACT AGCCATGGTC TTTACGTCGA TACCTAGGTA ACTTCAGTTG
         2350                                             2400
AACAAACCTG CCAAAGAACT TGAGGTGTTC TTAATTCAAA TACTATTTTG AGTTCCTATC
TTGTTTGGAC GGTTTCTTGA ACTCCACAAG AATTAAGTTT ATGATAAAAC TCAAGGATAG
                                        2450
ATATCATTTC AAGAAAGATC TTTTTTTTTA AAAGTTTGTT TTCGTGAAAT ATTTCAGAAC
TATAGTAAAG TTCTTTCTAG AAAAAAAAAT TTTCAAACAA AAGCACTTTA TAAAGTCTTG
                              2500
AGCTACAGAG AATATCTGAA GCTTAAGGGT AGATATGAGA ACCTTCAACG TCAACAGAGG
TCGATGTCTC TTATAGACTT CGAATTCCCA TCTATACTCT TGGAAGTTGC AGTTGTCTCC
                    2550
TACATATCTA TCTATACCTC CATATATTTA CTCAATTCTG TATCCATGTA GATTCATATT
ATGTATAGAT AGATATGGAG GTATATAAAT GAGTTAAGAC ATAGGTACAT CTAAGTATAA
              2600
TGTAGGTGTG TGTGGCTTTT GTTGGTGCAG AAATCTTCTT GGGGAGGATT TAGGACCTTT
ACATCCACAC ACACCGAAAA CAACCACGTC TTTAGAAGAA CCCCTCCTAA ATCCTGGAAA
         2650                                             2700
GAATTCAAAG GAGTTAGAGC AGCTTGAGCG TCAACTGGAC GGCTCTCTCA AGCAAGTTCG
CTTAAGTTTC CTCAATCTCG TCGAACTCGC AGTTGACCTG CCGAGAGAGT TCGTTCAAGC
                                        2750
GTCCATCAAG GTATCTTTAT GCATGGAATC AATGATTCAA ATGAGATTAA TTTGTGTTGT
CAGGTAGTTC CATAGAAATA CGTACCTTAG TTACTAAGTT TACTCTAATT AAACACAACA
```

Fig. 1c

```
                                            2800
TTAATTATAC TACTATGGTG GTATGATGAT TGTTTGCAGA CACAGTACAT GCTTGACCAG
AATTAATATG ATGATACCAC CATACTACTA ACAAACGTCT GTGTCATGTA CGAACTGGTC

2850
CTCTCGGATC TTCAAAATAA AGAGCAAATG TTGCTTGAAA CCAATAGAGC TTTGGCAATG
GAGAGCCTAG AAGTTTTATT TCTCGTTTAC AACGAACTTT GGTTATCTCG AAACCGTTAC

2900
AAGGTATAAT TACAGAATAA ATGCATTTGG TGACTTGCGA TCAATCTCTT TCACAGAGTT
TTCCATATTA ATGTCTTATT TACGTAAACC ACTGAACGCT AGTTAGAGAA AGTGTCTCAA 2950                                                      3000
TAAGTTTCTA AATATGTTTT GAAACATCTC TAGTTTTCTT GTTTCTGATT ATAGTCTTTT
ATTCAAAGAT TTATACAAAA CTTTGTAGAG ATCAAAAGAA CAAAGACTAA TATCAGAAAA

3050
GGTGAAATGT AAATGTTTAG CTGGATGATA TGATTGGTGT GAGAAGTCAT CATATGGGAG
CCACTTTACA TTTACAAATC GACCTACTAT ACTAACCACA CTCTTCAGTA GTATACCCTC

3100
GATGGGAAGG CGGTGAACAG AATGTTACCT ACGCGCATCA TCAAGCTCAG TCTCAGGGAC
CTACCCTTCC GCCACTTGTC TTACAATGGA TGCGCGTAGT AGTTCGAGTC AGAGTCCCTG

3150
TATACCAGCC TCTTGAATGC AATCCAACTC TGCAAATGGG GTAAATCTGC CTTGAAAAAT
ATATGGTCGG AGAACTTACG TTAGGTTGAG ACGTTTACCC CATTTAGACG GAACTTTTTA

3200
CATCTGCAAA TCAGTTTGTG TACTTAACTA CTAAGATTGT CCTTATTTAA GGTTCTTTAG
GTAGACGTTT AGTCAAACAC ATGAATTGAT GATTCTAACA GGAATAAATT CCAAGAAATC 3250                                            3300
TTGCTTGGTG TAAAGAGGAT CATCAATGTG TGTGAACCTT CTAAGTTGAT GTTTTGGCGA
AACGAACCAC ATTTCTCCTA GTAGTTACAC ACACTTGGAA GATTCAACTA CAAAACCGCT

3350
TGATGATGAT GATGCAGGTA TGATAATCCA GTATGCTCTG AGCAAATCAC TGCGACAACA
ACTACTACTA CTACGTCCAT ACTATTAGGT CATACGAGAC TCGTTTAGTG ACGCTGTTGT

3400
CAAGCTCAGG CGCAGCCGGG AAACGGTTAC ATTCCAGGAT GGATGCTCTG AGAATCATGT
GTTCGAGTCC GCGTCGGCCC TTTGCCAATG TAAGGTCCTA CCTACGAGAC TCTTAGTACA

3450
ACTGTGATGA AGCTCACCCA CAAAAGACCT TATATATATA TAAAGTATAG ATACAAGACT
TGACACTACT TCGAGTGGGT GTTTTCTGGA ATATATATAT ATTTCATATC TATGTTCTGA

3500
TGGATTTGTA GACATAAGTG GCTAATATAA TGGTCCTGAG GATCTTCTAG ACATTTGTAT
ACCTAAACAT CTGTATTCAC CGATTATATT ACCAGGACTC CTAGAAGATC TGTAAACATA 3550                                            3600
CTTTTGGGAA TCCTTGCTTA TATTAAGAAT TCAAATGTGT GGAACTTGTT TTAACACTGA
GAAAACCCTT AGGAACGAAT ATAATTCTTA AGTTTACACA CCTTGAACAA AATTGTGACT

3650
ACCATGACAC TGGTTTATTA TCATGTAATG AGAGAAACAT TTGGGTTACA ATGTGATCTC
TGGTACTGTG ACCAAATAAT AGTACATTAC TCTCTTTGTA AACCCAATGT TACACTAGAG

3700
TCCTTGACCC AAATACACAA TATAAACCCT ATGCCAAAAT ACAAGCATCA CATATATATA
```

Fig. 1d

```
AGGAACTGGG TTTATGTGTT ATATTTGGGA TACGGTTTTA TGTTCGTAGT GTATATATAT
                      3750
TTCATAAAAG GTTTAAGTAA TCATACAAAT GATGTAAAAA GTTTCATGCC TTGAACAAAA
AAGTATTTTC CAAATTCATT AGTATGTTTA CTACATTTTT CAAAGTACGG AACTTGTTTT
           3800
CACTGCGCCA AAGGCAAATG GTAAGAAACA TGTCAGATTC CTGTGTGCAT CTGTTTTGCT
GTGACGCGGT TTCCGTTTAC CATTCTTTGT ACAGTCTAAG GACACACGTA GACAAAACGA 3850                                                    3900
GCTGCTGCTG TTGTTATCTC TCAAGAGGGT TTCCTCAGAA CTCCATAAGC CAAACGTGCA
CGACGACGAC AACAATAGAG AGTTCTCCCA AAGGAGTCTT GAGGTATTCG GTTTGCACGT

3950
GAGAGACGTT TCCTCATTCC CCCATCGTAT ACAATACCAT ATATTGTTAA AAAAAAGATA
CTCTCTGCAA AGGAGTAAGG GGGTAGCATA TGTTATGGTA TATAACAATT TTTTTTCTAT
                                4000
TCACAGATCA AATCAATTTG CACATCTCTC TGCTGCCTTG TCAATCTCCT CAGGTCCGGT
AGTGTCTAGT TTAGTTAAAC GTGTAGAGAG ACGACGGAAC AGTTAGAGGA GTCCAGGCCA

4050
CAAGGCAGAT CAAGACAGGA TCAATGGCAA CAAGTTACGG TGTTTCGTTG AACTCCATCA
GTTCCGTCTA GTTCTGTCCT AGTTACCGTT GTTCAATGCC ACAAAGCAAC TTGAGGTAGT

4100
CCTGCAAATG AGACGAATTC ACAGCAGAGA AAAAAATATT CTTTAGTCAA CATGAATGAG
GGACGTTTAC TCTGCTTAAG TGTCGTCTCT TTTTTTATAA GAAATCAGTT GTACTTACTC 4150                                          4200
AAATAATTCA AATGTTCTGA GTTTCAGGAA GAATGATTAG CCATATTTGT ACTAGACAAG
TTTATTAAGT TTACAAGACT CAAAGTCCTT CTTACTAATC GGTATAAACA TGATCTGTTC

4250
ACAAGTAAAG ATTTTACGCA TGTGCTTCTA GGGTTGTTGT ACATCTTTCA TTCTATTGAT
TGTTCATTTC TAAAATGCGT ACACGAAGAT CCCAACAACA TGTAGAAAGT AAGATAACTA

4300
CTCTGGATCA CTCGTCTATT TATGCGTGAT GGTGTCTGAG TCTGACTCTG AAACACTAGT
GAGACCTAGT GAGCAGATAA ATACGCACTA CCACAGACTC AGACTGAGAC TTTGTGATCA

4350
AAATGAGAAG CCGAAAACTG GCTTGGAAGA ACATGAAAAG TGTTTACCTT TCCACAAACA
TTTACTCTTC GGCTTTTGAC CGAACCTTCT TGTACTTTTC ACAAATGGAA AGGTGTTTGT

4400
GGGCAGTTTT CACTTCTCTC CATCCATTCA TAAATGCAAC TAAGGTGGAA ATGGTGAGAA
CCCGTCAAAA GTGAAGAGAG GTAGGTAAGT ATTTACGTTG ATTCCACCTT TACCACTCTT 4450                                4500
CACTTTGTAA CAATCTTCGG GTTCTCTGAT ATGTATTCTA CAAAACACAC GAAATAATCT
GTGAAACATT GTTAGAAGCC CAAGAGACTA TACATAAGAT GTTTTGTGTG CTTTATTAGA

GATACTAAGC TT
CTATGATTCG AA
```

Fig. 1e

```
                                                                  -1104
TGATAGCGCT  TCGTTCATCA  TGCAGAAGAA  ACCAATGTTT  CCCCAATCTC
ACTATCGCGA  AGCAAGTAGT  ACGTCTTCTT  TGGTTACAAA  GGGGTTAGAG

-1054
ACGCGCCTCC  TCCTATCTAC  CACCACTTGG  ACAAATCCCC  TTTGCAGTAT
TGCGCGGAGG  AGGATAGATG  GTGGTGAACC  TGTTTAGGGG  AAACGTCATA

-1004
TCGTTTTTTT  TTCCGGACAT  TGTACATTCA  AAAGCATTCC  AAGTGTCTAA
AGCAAAAAAA  AAGGCCTGTA  ACATGTAAGT  TTTCGTAAGG  TTCACAGATT

-954
TAAACATAAC  TAACCACTCC  AAGATGCAAA  ATCTAGCTAC  GACGAACAAA
ATTTGTATTG  ATTGGTGAGG  TTCTACGTTT  TAGATCGATG  CTGCTTGTTT

-904
TTTTAAACTA  TAGAGATGAA  CTTTAAATTC  GGGCATTAAT  TAGTGGAACT
AAAATTTGAT  ATCTCTACTT  GAAATTTAAG  CCCGTAATTA  ATCACCTTGA

-854
TGAGCTATTG  ATGATCGAGT  TTTCTGACTT  TTTGAAGCTT  AAGCTTAATT
ACTCGATAAC  TACTAGCTCA  AAAGACTGAA  AAACTTCGAA  TTCGAATTAA

-804
GAGTTTTATA  TACACTATAT  AGGCTTGTAA  TAATATGGAT  CAAACAAGAA
CTCAAAATAT  ATGTGATATA  TCCGAACATT  ATTATACCTA  GTTTGTTCTT

-754
AAATACAAAC  TACAAATTGG  GAATTGGGTT  TTAAAACGTT  ATCGTTCTAT
TTTATGTTTG  ATGTTTAACC  CTTAACCCAA  AATTTTGCAA  TAGCAAGATA

-704
TTTAATTCAG  GCACGTACCT  TTAGAATATC  AAGATCCATG  TTTCAATATT
AAATTAAGTC  CGTGCATGGA  AATCTTATAG  TTCTAGGTAC  AAAGTTATAA

-654
TCTGTTGACA  AATAAATAAA  GATGTCTCAA  ATATAAGTTG  GGCAACGTAC
AGACAACTGT  TTATTTATTT  CTACAGAGTT  TATATTCAAC  CCGTTGCATG

-604
GTGTAGACCT  AAAAGAGTCG  AAACATTGGT  ATCTAAGTTA  TATATCTACA
CACATCTGGA  TTTTCTCAGC  TTTGTAACCA  TAGATTCAAT  ATATAGATGT

-554
TGGATTATAT  AACAAGACAA  CGTTTGTTTT  AAAAACTTCA  TTGATTTTTC
ACCTAATATA  TTGTTCTGTT  GCAAACAAAA  TTTTTGAAGT  AACTAAAAAG

-504
TTAATTAGTA  GCAACTAGCA  ACTAACTACT  CATGGCAAAT  AATGGCGTCT
AATTAATCAT  CGTTGATCGT  TGATTGATGA  GTACCGTTTA  TTACCGCAGA

-454
GCGTGGCACG  CGACTTGGGA  GAGAAGGTGT  GAGAATGTTT  TTACTTTCTG
CGCACCGTGC  GCTGAACCCT  CTCTTCCACA  CTCTTACAAA  AATGAAAGAC

```
TGTAAAAGAT GGAAGAGAGA GAAAGAGTAA AGAAGTAGAG AGAGAGATAT
ACATTTTCTA CCTTCTCTCT CTTTCTCATT TCTTCATCTC TCTCTCTATA

-354
TGTATCACCA AACCCTAATG ATCTCTCACC CTCACAAATT TTCTTATCTT
ACATAGTGGT TTGGGATTAC TAGAGAGTGG GAGTGTTTAA AAGAATAGAA

-304
TATAGCTTTT ATAGATTCAC AAAAACTTTT CTTCAGATTC ACAATCTCAT
ATATCGAAAA TATCTAAGTG TTTTTGAAAA GAAGTCTAAG TGTTAGAGTA

-254
CACAACCCTT CAAAAAGAGA AAAGATCTAA AGAATAAACA AGAGCCCTAA
GTGTTGGGAA GTTTTTCTCT TTTCTAGATT TCTTATTTGT TCTCGGGATT

-204
TATCAAATCA CAACCAAAAA AACCAAAGAA AGCTAATTAA AGTTTTCTCT
ATAGTTTAGT GTTGGTTTTT TTGGTTTCTT TCGATTAATT TCAAAAGAGA

-154
CTAGCTATTC CTCTTCTTTT CTTGTTCTTG AAAACTAGGG TTTACTTCAC
GATCGATAAG GAGAAGAAAA GAACAAGAAC TTTTGATCCC AAATGAAGTG

-104
CAAAAAGATA AGATCTTTCC CCAGAAAAAG CAATACCCAA GTCATGTTTC
GTTTTTCTAT TCTAGAAAGG GGTCTTTTTC GTTATGGGTT CAGTACAAAG

-54
TGTGTGTCTG TATATAGATA AAACATTACA TACCCTAATA AGGTTACACA
ACACACAGAC ATATATCTAT TTTGTAATGT ATGGGATTAT TCCAATGTGT

-4
AATAGCTATA AAAGAGGGAA AATAAGATAG GGATTTTTTG GGGTGAGGAA
TTATCGATAT TTTCTCCCTT TTATTCTATC CCTAAAAAAC CCCACTCCTT

47
AGATGGGAAG AGGAAGAGTA GAGCTCAAGA GGATAGAGAA CAAAATCAAC
TCTACCCTTC TCCTTCTCAT CTCGAGTTCT CCTATCTCTT GTTTTAGTTG

97
AGACAAGTGA CGTTTGCTAA ACGTAGAAAT GGTTTCGTGA AAAAAGCTTA
TCTGTTCACT GCAAACGATT TGCATCTTTA CCAAAGCACT TTTTTCGAAT

147
TGAGCTTTCT GTTCTCTGCG ATGCTGAAGT CTCTCTCATC GTCTTCTCCA
ACTCGAAAGA CAAGAGACGC TACGACTTCA GAGAGAGTAG CAGAAGAGGT

197
ACCGTGGCAA GCTCTACGAG TTCTGCAGCA CCTCCAAGTA CTTCTCTTTC
TGGCACCGTT CGAGATGCTC AAGACGTCGT GGAGGTTCAT GAAGAGAAAG

247
TTTATACACT TATTAGATCT GTGTGTAGAT CTTTCATTTT TTCTAGTCTT
AAATATGTGA ATAATCTAGA CACACATCTA GAAAGTAAAA AAGATCAGAA

297
GTGATGAGTT TTATCTTTCT TGATTGCTTT TTAACAAAAT ACTTGATATA
```

Fig. 2b

```
CACTACTCAA AATAGAAAGA ACTAACGAAA AATTGTTTTA TGAACTATAT

347
TTTTCAGTTT CTTAATCTGA CTCTAATTAG GTTTTGATTA ATAGGAAGGA
AAAAGTCAAA GAATTAGACT GAGATTAATC CAAAACTAAT TATCCTTCCT

397
AATAAATCCA GGTACCTTTC AAGGTGAATT G------GAG ATCTGATCTT
TTATTTAGGT CCATGGAAAG TTCCACTTAA C------CTC TAGACTAGAA

447
AATTTAATCA TCATGTCAAA TTCTTAGGGA TTTAATTGCA ATCTATTTTT
TTAAATTAGT AGTACAGTTT AAGAATCCCT AAATTAACGT TAGATAAAAA

497
AGATTTATCG GAGCTAGGAA AGTATCATAA TGATATACTA TTATTATCAT
TCTAAATAGC CTCGATCCTT TCATAGTATT ACTATATGAT AATAATAGTA

547
GTAATTTCAT TGTCTCTACA CGGATATATA TGTGATTAGA ACTTGGTAAA
CATTAAAGTA ACAGAGATGT GCCTATATAT ACACTAATCT TGAACCATTT

597
GTAAACTAAA GATTCACAGT CTTCAATGAA ATTGAAAAGA TCCAACGTAG
CATTTGATTT CTAAGTGTCA GAAGTTACTT TAACTTTTCT AGGTTGCATC

647
AATAATTAGT GGTTCCATGC ATTAACCAGT CTAATTAAAG CTCATGCAGA
TTATTAATCA CCAAGGTACG TAATTGGTCA GATTAATTTC GAGTACGTCT

697
CATTTAAGCA CCACATGAAT TTAATATCTT TTTAATTAAG GGATCTTCTT
GTAAATTCGT GGTGTACTTA AATTATAGAA AAATTAATTC CCTAGAAGAA

747
TTTATAAATT TTCTTTTGTT AGCTTTTAAA ATTTTAGTTT GTTCATTAAA
AAATATTTAA AAGAAAACAA TCGAAAATTT TAAAATCAAA CAAGTAATTT

797
ATTTATAGAT CCTCCTCTCC TGATTTGTGT TTTCCGATCC TTTCCAGCAT
TAAATATCTA GGAGGAGAGG ACTAAACACA AAAGGCTAGG AAAGGTCGTA

847
GCTCAAGACA CTGGAAAGGT ATCAGAAGTG TAGCTATGGC TCCATTGAAG
CGAGTTCTGT GACCTTTCCA TAGTCTTCAC ATCGATACCG AGGTAACTTC

897
TCAACAACAA ACCTGCTAAA CAGCTTGAGG TTTAATCTCC AACATCTCTT
AGTTGTTGTT TGGACGATTT GTCGAACTCC AAATTAGAGG TTGTAGAGAA

947
CGATCTTAAT TATTTATCCT TTTTTAATTT TATCTAAAGA AAATGTTTGA
GCTAGAATTA ATAAATAGGA AAAAATTAAA ATAGATTTCT TTTACAAACT

997
TTTTGAGACA AAAGCCCTTC AAAGTTTCTT ACATAGATAT TCAATTGTCT
AAAACTCTGT TTTCGGGAAG TTTCAAAGAA TGTATCTATA AGTTAACAGA
```

Fig. 2c.

```
                                                           1047
ATTATCTTCG CAATTTTCAG AACAGCTACA GAGAGTACTT GAAGCTGAAA
TAATAGAAGC GTTAAAAGTC TTGTCGATGT CTCTCATGAA CTTCGACTTT

1097
GGTAGATATG AAAATCTGCA ACGTCAGCAG AGGTATATAC ATTAATGTGG
CCATCTATAC TTTTAGACGT TGCAGTCGTC TCCATATATG TAATTACACC

1147
ATGATGATCA TTTATAAACA GCATATATAT ATATATATAT ATATATATAT
TACTACTAGT AAATATTTGT CGTATATATA TATATATATA TATATATATA

1197
ATATAGAAAG TATTGATCAT GAAAGTGTGT TGCAGCAGAA ATCTTCTTGG
TATATCTTTC ATAACTAGTA CTTTCACACA ACGTCGTCTT TAGAAGAACC

1247
AGAGGATCTT GGACCTCTGA ATTCAAAGGA GCTAGAGCAG CTTGAGCGTC
TCTCCTAGAA CCTGGAGACT TAAGTTTCCT CGATCTCGTC GAACTCGCAG

1297
AACTAGACGG CTCTCTGAAG CAAGTTCGCT GCATCAAGGT GATTTACTTC
TTGATCTGCC GAGAGACTTC GTTCAAGCGA CGTAGTTCCA CTAAATGAAG

1347
TGTACATACA CTGAAAGATT CACACAAATC TTTCTCTATA TATAGACTGA
ACATGTATGT GACTTTCTAA GTGTGTTTAG AAAGAGATAT ATATCTGACT

1397
GACACATGCA TGAAATGTTT TTGATGCGTG AGGTTATCTG AAAATGCCTC
CTGTGTACGT ACTTTACAAA AACTACGCAC TCCAATAGAC TTTTACGGAG

1447
TTCTTTTTTG CAGACACAGT ATATGCTTGA CCAGCTCTCT GATCTTCAAG
AAGAAAAAAC GTCTGTGTCA TATACGAACT GGTCGAGAGA CTAGAAGTTC

1497
GTAAGGAGCA TATCTTGCTT GATGCCAACA GAGCTTTGTC AATGAAGGTA
CATTCCTCGT ATAGAACGAA CTACGGTTGT CTCGAAACAG TTACTTCCAT

1547
TATGATGATG TTTCTCTCTC TCTCCTCCAG TTTCTATTTA TAGATGGAAA
ATACTACTAC AAAGAGAGAG AGAGGAGGTC AAAGATAAAT ATCTACCTTT

1597
CTTTAAATAG TCCAATTTAT ATATATGAGT CTAAATTTCA CATTCTTCAA
GAAATTTATC AGGTTAAATA TATATACTCA GATTTAAAGT GTAAGAAGTT

1647
CTGCTACATG TTTCTTTTGT ATTATTTCTA TGATATCTTC AGGAAAGTTT
GACGATGTAC AAAGAAAACA TAATAAAGAT ACTATAGAAG TCCTTTCAAA

1697
GAAAAATATT GTGTTTTGTT TAGCTGGAAG ATATGATCGG CGTGAGACAT
CTTTTTATAA CACAAAACAA ATCGACCTTC TATACTAGCC GCACTCTGTA
```

Fig. 2d

```
                                                  1747
CACCATATAG GAGGAGGATG GGAAGGTGGT GATCAACAGA ATATTGCCTA
GTGGTATATC CTCCTCCTAC CCTTCCACCA CTAGTTGTCT TATAACGGAT

1797
TGGACATCCT CAGGCTCATT CTCAGGGACT ATACCAATCT CTTGAATGTG
ACCTGTAGGA GTCCGAGTAA GAGTCCCTGA TATGGTTAGA GAACTTACAC

1847
ATCCCACTTT GCAAATTGGG TAAATCAAAC AACTTTTCTT GCTTTAAGAC
TAGGGTGAAA CGTTTAACCC ATTTAGTTTG TTGAAAAGAA CGAAATTCTG

1897
ATCAACTTAG GTTATAAACA GTTAGCAGTT TGCTTTAAGC CCAACATTGT
TAGTTGAATC CAATATTTGT CAATCGTCAA ACGAAATTCG GGTTGTAACA

1947
CTTTGTTTCA TAGAGGCTTT GGTTAAAACT CGTGTTGTTT AGTCTAAGGA
GAAACAAAGT ATCTCCGAAA CCAATTTTGA GCACAACAAA TCAGATTCCT

1997
TTCAGCACTT TGATGTCTGA AGTATGGAAA ATCAATCTCT CAGACTTGAA
AAGTCGTGAA ACTACAGACT TCATACCTTT TAGTTAGAGA GTCTGAACTT

2047
AATGTGGGTT TCTATTGTTG ACTTCGAAAC TATGTTGTTG TGGTGTTGCA
TTACACCCAA AGATAACAAC TGAAGCTTTG ATACAACAAC ACCACAACGT

2097
AACAGATATA GCCATCCAGT GTGCTCAGAG CAAATGGCTG TGACGGTGCA
TTGTCTATAT CGGTAGGTCA CACGAGTCTC GTTTACCGAC ACTGCCACGT

2147
AGGTCAGTCC CAACAAGGAA ACGGCTACAT CCCTGGCTGG ATGCTGTGAG
TCCAGTCAGG GTTGTTCCTT TGCCGATGTA GGGACCGACC TACGACACTC

2197
CGATACTTCT TCCCCCAATA AAGATCTTAA GCAAGTACTG GTGGGGTCTT
GCTATGAAGA AGGGGGTTAT TTCTAGAATT CGTTCATGAC CACCCCAGAA

2247
CGTGGTGTGA TCTTAGATCT TATGCATATG AATAATAATG TTATTGCACA
GCACCACACT AGAATCTAGA ATACGTATAC TTATTATTAC AATAACGTGT

2297
AGACTTTTGC TTTTGTAGAC ACAAGTGGCT ATAGCTGTAA TAGCCTTCAA
TCTGAAAACG AAAACATCTG TGTTCACCGA TATCGACATT ATCGGAAGTT

2347
CATCTCTCTT CTGTTTCAGG ATTTGTTTGT GCCTATTGTA ATTGCTTATA
GTAGAGAGAA GACAAAGTCC TAAACAAACA CGGATAACAT TAACGAATAT

2397
TATGTATGGT TTGTATAATG TGTGAAATGT TAACATCGAC CATGTCTCAT
ATACATACCA AACATATTAC ACACTTTACA ATTGTAGCTG GTACAGAGTA

CTGGTGAAGA TCTTATCCTG TCTATGCATG ATACCAAAA
```

Fig. 2e

GACCACTTCT AGAATAGGAC AGATACGTAC TATGGTTTT

Fig. 2f

```
Sequence Range: 1 to 14940
                                            50
    TAAAATCTGG AAGTTTCCAG CCCTGATAAT GTTGCAGAAT AAATTAGTGC GCAGTAAGTC
    ATTTTAGACC TTCAAAGGTC GGGACTATTA CAACGTCTTA TTTAATCACG CGTCATTCAG 100
    TCCAAAAAGA GAGAAACTAC AAATAAATAA ACCAAGTCAA ATTCATTAAC AAGGAGAACA
    AGGTTTTTCT CTCTTTGATG TTTATTTATT TGGTTCAGTT TAAGTAATTG TTCCTCTTGT 150
    GCATGAAATG TTTCCCAAAC ACACAAAATC TTGACTAGCC AACAGCGCTT CAAATGAGGA
    CGTACTTTAC AAAGGGTTTG TGTGTTTTAG AACTGATCGG TTGTCGCGAA GTTTACTCCT 200
    AGTAACTAAT TTCAGTAGCT TGGGTATGGT GAAGTATAAT TACCTTCCAC CACACATATC
    TCATTGATTA AAGTCATCGA ACCCATACCA CTTCATATTA ATGGAAGGTG GTGTGTATAG 250                                          300
    CGTAGCCTAT CACCCCAACG ATAATGATCA AACCATAGTT TCTACCACCT GTACATTGAA
    GCATCGGATA GTGGGGTTGC TATTACTAGT TTGGTATCAA AGATGGTGGA CATGTAACTT 350
    GGAAAGTGTT AACTGTTTTC TTCCGAATTT AGATCAACAG TAAACAAAGA ATGGTGTTAC
    CCTTTCACAA TTGACAAAAG AAGGCTTAAA TCTAGTTGTC ATTTGTTTCT TACCACAATG 400
    TCTAAGTCTC TAATGTAATG CCTTCCTAAA TGCTACAAAG AAAAGCCACT TATCAGAACA
    AGATTCAGAG ATTACATTAC GGAAGGATTT ACGATGTTTC TTTTCGGTGA ATAGTCTTGT 450
    AAGTATGTCT TGTTTGATGC GAGAAAAGTA GCAAAAGAGA ATAAAACCTG AAATATAATT
    TTCATACAGA ACAAACTACG CTCTTTTCAT CGTTTTCTCT TATTTTGGAC TTTATATTAA 500
    TCAAAATACA ATGTCTAGAA ATCTAAGTGT GCAAATCCTT TATTCAAGTT TCATATCAAA
    AGTTTTATGT TACAGATCTT TAGATTCACA CGTTTAGGAA ATAAGTTCAA AGTATAGTTT 550                                          600
    CCAATTTTGA CATTTCTAGT GCAGAACAGA AAACAAAACT TCAATATAAA AAAATATAAA
    GGTTAAAACT GTAAAGATCA CGTCTTGTCT TTTGTTTTGA AGTTATATTT TTTTATATTT 650
    AACTCCAGAG GACCTGATCC TGAAGGTGAA ACAATGGTGA TAGGTCTGTT TGACCCCAGC
    TTGAGGTCTC CTGGACTAGG ACTTCCACTT TGTTACCACT ATCCAGACAA ACTGGGGTCG 700
    AACTGTATCT CATGCCTAAG ACTGTTAACC TACAAAAATA AATAGAGCTC AGGCAAGAAA
    TTGACATAGA GTACGGATTC TGACAATTGG ATGTTTTTAT TTATCTCGAG TCCGTTCTTT 750
    CTATTGATTC ACGATAAATC TATGTCCTCA GCAAGTCTAT ATTATCCAGC TCCATCCGAT
    GATAACTAAG TGCTATTTAG ATACAGGAGT CGTTCAGATA TAATAGGTCG AGGTAGGCTA 800
    AGCTTATCAT CGCCAATAGA TTAATGTGAA ACTTACCTGG GCCACAAGTA CATCATCGTG
    TCGAATAGTA GCGGTTATCT AATTACACTT TGAATGGACC CGGTGTTCAT GTAGTAGCAC 850                                          900
    GGGTTTGCTA GCTGATTTGC TAGGTTCGTC TTGTTTCAGT TGCCTGAATA CCATCTGTCC
    CCCAAACGAT CGACTAAACG ATCCAAGCAG AACAAAGTCA ACGGACTTAT GGTAGACAGG
```

Fig. 3a

```
                                                         950
ACATAAACAA AACCCATTGC CTCATTTTGC CAAACCGCAT CATACACATG TGAAGTCGCC
TGTATTTGTT TTGGGTAACG GAGTAAAACG GTTTGGCGTA GTATGTGTAC ACTTCAGCGG

1000
AAAGCTTTTG CACAATATAG AAATTAGAAT ACCTTAAAAG CACCAGAAAC CAAATTGGAG
TTTCGAAAAC GTGTTATATC TTTAATCTTA TGGAATTTTC GTGGTCTTTG GTTTAACCTC

1050
ACATCTGGTA AGCCCCCTTC TTTAGAAAAT GCTGATCCAA TAAGACCTTA AAGTAACATT
TGTAGACCAT TCGGGGGAAG AAATCTTTTA CGACTAGGTT ATTCTGGAAT TTCATTGTAA

1100
TGCAAAAATC ACAGTATAGT TAGTAATTGC AGTAACTTGG ACGAACATTA AGCATGTACA
ACGTTTTTAG TGTCATATCA ATCATTAACG TCATTGAACC TGCTTGTAAT TCGTACATGT 1150                                        1200
CGAAATCAAT CGACTCAGCA AGTTCACAAT AATTGTACTA GTAGGTGCAT TCACAGAGAA
GCTTTAGTTA GCTGAGTCGT TCAAGTGTTA TTAACATGAT CATCCACGTA AGTGTCTCTT

1250
ACTAAACATA AACTTCTCCT CAGATGTATT CAGAGAATAG CTATACTCCA ATAAAGTCTT
TGATTTGTAT TTGAAGAGGA GTCTACATAA GTCTCTTATC GATATGAGGT TATTTCAGAA

1300
AAACTTTGAG CCAGTCAAGT ACACTGATCA AAGGGTTTAT GAAAAACACT AACTTCTTAT
TTTGAAACTC GGTCAGTTCA TGTGACTAGT TTCCCAAATA CTTTTTGTGA TTGAAGAATA

1350
CCTCTAATTG CGATTACCCA TAGACGAAAC CAATAAAAAA GCAATGGAGA ACTAGAGCAC
GGAGATTAAC GCTAATGGGT ATCTGCTTTG GTTATTTTTT CGTTACCTCT TGATCTCGTG

1400
AGTCACTACA AGAAATACCC TATAAAAGTA CCGACCTGCA CCGATGAGGA TGGTGAGCTT
TCAGTGATGT TCTTTATGGG ATATTTTCAT GGCTGGACGT GGCTACTCCT ACCACTCGAA 1450                                        1500
CCCGAGCGGA AGAGCCATGG CTAGAGACGA GCTTATACGG CGAAGAACTA AGATGGCAAA
GGGCTCGCCT TCTCGGTACC GATCTCTGCT CGAATATGCC GCTTCTTGAT TCTACCGTTT

1550
CGAATCCGCG TGAGAATATC TAAGAGAGTA TTGGTAAGAG AGAGCTGCAG GAACGTACCG
GCTTAGGCGC ACTCTTATAG ATTCTCTCAT AACCATTCTC TCTCGACGTC CTTGCATGGC

1600
GTGAAACAGA GGCGTTTTTT GGGACGATGA AGTGAGGCAG CGAGAGAGAT ACGACGTGCG
CACTTTGTCT CCGCAAAAAA CCCTGCTACT TCACTCCGTC GCTCTCTCTA TGCTGCACGC

1650
ACTATATTGT TCGCTTGTTG AGGCAACAAA ACAGAGTTGC TTCTAAAACC CGAACCGAAA
TGATATAACA AGCGAACAAC TCCGTTGTTT TGTCTCAACG AAGATTTTGG GCTTGGCTTT

1700
TGTCCGGTCT GATTCGGTCT AAATCACGAT TAGGTTCGTT TTAAAACCTA GGAGGCAATA
ACAGGCCAGA CTAAGCCAGA TTTAGTGCTA ATCCAAGCAA AATTTTGGAT CCTCCGTTAT 1750                                        1800
ACCGGACGGA TCATAAATTC ATAATAGAGA CAGACAAATT GGTCCATTAT TAAAATCACT
TGGCCTGCCT AGTATTTAAG TATTATCTCT GTCTGTTTAA CCAGGTAATA ATTTTAGTGA

1850
TGGGCATTTG GGGATGATTC AAATGCCCAA GTTTTCTCAA ATTTGGACGA TTCATTCACC
```

Fig. 3b

```
           ACCCGTAAAC CCCTACTAAG TTTACGGGTT CAAAAGAGTT TAAACCTGCT AAGTAAGTGG

1900
TAAGACATAC TTGAGCAACA ACAAAGTGAA GTCCACTGTC ATATCTTATG TCTCAAAAAG
ATTCTGTATG AACTCGTTGT TGTTTCACTT CAGGTGACAG TATAGAATAC AGAGTTTTTC

1950
TATTGAAATG TGTCAATTGA TATTGGAGAG GCACACTAGC TAAGGGATTA TTCAATCAAT
ATAACTTTAC ACAGTTAACT ATAACCTCTC CGTGTGATCG ATTCCCTAAT AAGTTAGTTA

2000
TTCCAGCAAT TTAATTAAAC TTATTTGTAG TGAAAGTGGG AAGATAAAAG ATCTCACCCT
AAGGTCGTTA AATTAATTTG AATAAACATC ACTTTCACCC TTCTATTTTC TAGAGTGGGA 2050                                                           2100
CACATGTTCA AAAAAAAAAG TTGAAAATGG AAGTAATTCA ACATGTAGCA TAGAGCCCAA
GTGTACAAGT TTTTTTTTTC AACTTTTACC TTCATTAAGT TGTACATCGT ATCTCGGGTT

2150
ATATGTCTCA TTTTTTTAAT CCATATAATC TCAAATCCTC TTACTTACTT CTAAACATAT
TATACAGAGT AAAAAAATTA GGTATATTAG AGTTTAGGAG AATGAATGAA GATTTGTATA

2200
GGTTCCCATA ATCATAACAA TGCTATGTTA ACATGGCCGG TTCTAAAGGA AGCCAAGTGC
CCAAGGGTAT TAGTATTGTT ACGATACAAT TGTACCGGCC AAGATTTCCT TCGGTTCACG

2250
AGCAACTGCC TTACGCCTCT ACGTGTTAAA ATGAAAATGA AGACCACTGA CCACTTCTAT
TCGTTGACGG AATGCGGAGA TGCACAATTT TACTTTTACT TCTGGTGACT GGTGAAGATA

2300
TAAAGCTTCA TTCACTAGTG TATAATTACA CATTTTTTTA AGGATTTATG AGTAGTGATT
ATTTCGAAGT AAGTGATCAC ATATTAATGT GTAAAAAAAT TCCTAAATAC TCATCACTAA 2350                                      2400
GAGGCCCATA TGTTTGTATG TTTGTTTTTC TTACTATATC ATTACTTGAC TATAAGAGTT
CTCCGGGTAT ACAAACATAC AAACAAAAAG AATGATATAG TAATGAACTG ATATTCTCAA

2450
GGTTTCCTAT TCCATTCTCT TTTCTAACAG CCTATATATG TAAAAATCTA AGCAAAATTT
CCAAAGGATA AGGTAAGAGA AAAGATTGTC GGATATATAC ATTTTTAGAT TCGTTTTAAA

2500
CTTGTCAAGA GGATGATTGT ACATTTGTAC TTGGTTATCT CGCCCCGGCC CAAAACATAC
GAACAGTTCT CCTACTAACA TGTAAACATG AACCAATAGA GCGGGGCCGG GTTTTGTATG

2550
CTAAGGCCAG GTGCTATATC CTCAACCTGC TTTGGCATTC ATCAATCTAC GAACTTTGGC
GATTCCGGTC CACGATATAG GAGTTGGACG AAACCGTAAG TAGTTAGATG CTTGAAACCG

2600
GTGAAACGGT GACAAGATTA ACAAGATTCA CTCTCAACTA CGATGTTCTA CTATCTCAAA
CACTTTGCCA CTGTTCTAAT TGTTCTAAGT GAGAGTTGAT GCTACAAGAT GATAGAGTTT 2650                                      2700
TCTTTAAAAA AGTGGATCAA ACTGTCAAAA GTCTAGTTCG ATGGACTAGC TTCAACACTC
AGAAATTTTT TCACCTAGTT TGACAGTTTT CAGATCAAGC TACCTGATCG AAGTTGTGAG

2750
CTCCAAATCT AGTTCGATGG ACTATATATT CTCTTCTGAT GCTATCCTTA TCTTGGATTA
GAGGTTTAGA TCAAGCTACC TGATATATAA GAGAAGACTA CGATAGGAAT AGAACCTAAT
```

Fig 3c

```
                                              2800
GGCATCTAAA CTATGGTTTT AATGGTGTCA TGAGGTTTTA CAACTTACAA GGATGAAAGT
CCGTAGATTT GATACCAAAA TTACCACAGT ACTCCAAAAT GTTGAATGTT CCTACTTTCA

2850
TATTTACTCC CAGTCACTAT CTTAATCAAA TGACAAAATG TTAACTAGTT TGAGTGCTTA
ATAAATGAGG GTCAGTGATA GAATTAGTTT ACTGTTTTAC AATTGATCAA ACTCACGAAT

2900
TATATTAGTT ATGAATCTGA AATTTATTAG TGTGTACATA AGTGATACAA CACTTAAATA
ATATAATCAA TACTTAGACT TTAAATAATC ACACATGTAT TCACTATGTT GTGAATTTAT 2950                                               3000
ACATCTACAT GAGTTTTTAA ATAACATAAT AATCCATTAT AGTAGTTTAC GGCATAAGGT
TGTAGATGTA CTCAAAAATT TATTGTATTA TTAGGTAATA TCATCAAATG CCGTATTCCA

3050
ATGAACCAAA TTTTTCATTG CACGCTGAAA AGTGAAAACC TTTAAAATGC ATAATGACTA
TACTTGGTTT AAAAAGTAAC GTGCGACTTT TCACTTTTGG AAATTTTACG TATTACTGAT

3100
AGAGTCTATG ACAACAGTAA CTTACTATAT ATTAGAGGAG GGGTGAAAAA AAAAGTAGAG
TCTCAGATAC TGTTGTCATT GAATGATATA TAATCTCCTC CCCACTTTTT TTTTCATCTC

3150
AGACTGGTCC AAAAACTTAA CCCCACTCAA TAAACCCAGA CGTGACTTGT TGACGATAA
TCTGACCAGG TTTTTGAATT GGGGTGAGTT ATTTGGGTCT GCACTGAACA AACTGCTATT

3200
CTCCATCTTT CTATTTTGGG TAACGAGGTC CCCTTCCCAT TACGTCTTGA CGTGGACCCT
GAGGTAGAAA GATAAAACCC ATTGCTCCAG GGGAAGGGTA ATGCAGAACT GCACCTGGGA 3250                                          3300
GTCCGTCTAT TTTTAGCAGA TTAATCCAAC GGTTCTTATT CTTTCTTCGA CCCTTCACGA
CAGGCAGATA AAAATCGTCT AATTAGGTTG CCAAGAATAA GAAAGAAGCT GGGAAGTGCT

3350
CATTGCCTCA AAGCCGTCCG ATTCTCATCT CACGCCCAAT GGACCACATA TATCACCAGT
GTAACGGAGT TTCGGCAGGC TAAGAGTAGA GTGCGGGTTA CCTGGTGTAT ATAGTGGTCA

3400
ACTCCGCAAC TTAGCTGTCG TGTAGGATTT CACGTGGCAT TTATTTGTTC TAGTTTGTAG
TGAGGCGTTG AATCGACAGC ACATCCTAAA GTGCACCGTA AATAAACAAG ATCAAACATC

3450
TGCAAACATT GCAAGTTGAT ATGGTCCCCT ATCGATCACC GTCGTCTCTT TAGCTTCACA
ACGTTTGTAA CGTTCAACTA TACCAGGGGA TAGCTAGTGG CAGCAGAGAA ATCGAAGTGT

3500
TCGAGATTCT TCTTTCTTTC CTACGTGTAA TAGCATTTTT GATTTTGAGA ATTTCTTTAG
AGCTCTAAGA AGAAAGAAAG GATGCACATT ATCGTAAAAA CTAAAACTCT TAAAGAAATC 3550                                                    3600
AACCGTTGGA TCTCTCATCG TTGGTTGATC CATCCATCCA AATGGGACCT GTGTGTGCTC
TTGGCAACCT AGAGAGTAGC AACCAACTAG GTAGGTAGGT TTACCCTGGA CACACACGAG

3650
CATCCAGGGC ATATGATCCC AAAGCCAAAA GAGTATTTCC AAGTGCTTTC TTTCTTTCTT
GTAGGTCCCG TATACTAGGG TTTCGGTTTT CTCATAAAGG TTCACGAAAG AAAGAAAGAA

3700
TCTTTCTTTC TTACTAACCT TTTTTTTTCT TATGCTTTAG ACTAAGAAAT TTATTCGGCC
```

Fig. 3d

```
AGAAAGAAAG AATGATTGGA AAAAAAAAGA ATACGAAATC TGATTCTTTA AATAAGCCGG
           3750
ATATCCACTT TTACGAATAT ACTTCTTACA AGATCTAGAT TTTTTTGAGT TAATTCGGTG
TATAGGTGAA AATGCTTATA TGAAGAATGT TCTAGATCTA AAAAAACTCA ATTAAGCCAC
           3800
TATATAACAT TGGCATGGAC TGCAATTAAG TAATGGTAAT GTGATCATGA TGCGATGTGT
ATATATTGTA ACCGTACCTG ACGTTAATTC ATTACCATTA CACTAGTACT ACGCTACACA
  3850                                                      3900
CGTTATCAGT AGTATAATAT TGATGGGCTA CCCTGGAAAA CAAAATTACG TGTTATATGT
GCAATAGTCA TCATATTATA ACTACCCGAT GGGACCTTTT GTTTTAATGC ACAATATACA
                                 3950
ACACAATTTG GTAGAACCGT AGAAATTAAA CTGAATAAAA CCTTCTATAA TGTTCAAAAT
TGTGTTAAAC CATCTTGGCA TCTTTAATTT GACTTATTTT GGAAGATATT ACAAGTTTTA
                      4000
TATATGGTAC AGATTAATAC GGAAAAACAT TCACGCTTTA CGTAACAATT AAGTGGAAAG
ATATACCATG TCTAATTATG CCTTTTTGTA AGTGCGAAAT GCATTGTTAA TTCACCTTTC
           4050
TAAAATTATC CCAAAAATAT TTATATCACA TCATTGTTAT ATTTCTAAGT TTTTTTATAT
ATTTTAATAG GGTTTTTATA AATATAGTGT AGTAACAATA TAAAGATTCA AAAAAATATA
  4100
CTCTAATGGT ATATGTTTTA CAGATTGTTT TTTGGGAAAA TTCTTAAAGA GACTTGAAGA
GAGATTACCA TATACAAAAT GTCTAACAAA AAACCCTTTT AAGAATTTCT CTGAACTTCT
  4150                                                      4200
ATGTTTTTTT TTTATTTTCT TGAAATGTTT GACACTTGAA ACCGTTTAAA AACTCAAATA
TACAAAAAAA AAATAAAAGA ACTTTACAAA CTGTGAACTT TGGCAAATTT TTGAGTTTAT
                                 4250
TAGTATATAT CATTGTTGGT CTCATACCTT GTAATTCACC ACATATATTA TCAATGGGGA
ATCATATATA GTAACAACCA GAGTATGGAA CATTAAGTGG TGTATATAAT AGTTACCCCT
                      4300
AGATTTGAAA ATTTTTGGGG GATCACAAAA CGAAGGAAAG AGTACAAAAA GAGAAGGAAA
TCTAAACTTT TAAAAACCCC CTAGTGTTTT GCTTCCTTTC TCATGTTTTT CTCTTCCTTT
           4350
AGATAGAAGA TATATGTTTT TAACTTCATT GGTATGACAT CAATAAATAA ATAGTTGAAT
TCTATCTTCT ATATACAAAA ATTGAAGTAA CCATACTGTA GTTATTTATT TATCAACTTA
           4400
GTACTTTAGT TTCTCTTTTG GTTTAATGCA CATCATCTCG ATCAATTGTC ATCATCTTAC
CATGAAATCA AAGAGAAAAC CAAATTACGT GTAGTAGAGC TAGTTAACAG TAGTAGAATG
  4450                                                      4500
ATTGAATTAT ACGACCAGAT CTGATAACAA GTGAATTCGT ACTTGCCCTT CCCTTTCTTC
TAACTTAATA TGCTGGTCTA GACTATTGTT CACTTAAGCA TGAACGGGAA GGGAAAGAAG
                                 4550
TCATACGTCC TTCTAACTAA TTTTGATTGT AACTTATAAT TATATAACCA TATTTAATTT
AGTATGCAGG AAGATTGATT AAAACTAACA TTGAATATTA ATATATTGGT ATAAATTAAA
                      4600
TATTTTATCT AAAACCAATT GAAGCAAATT AAAATATCAT AAATCTTGAG TCCCACATGA
ATAAAATAGA TTTTGGTTAA CTTCGTTTAA TTTTATAGTA TTTAGAACTC AGGGTGTACT
```

Fig. 3e

```
                              4650
AGACAATATA TAAAACTCGT GCAAATTTGC TTAAAATGCT TCTATGAGAC CATGACCAAG
TCTGTTATAT ATTTTGAGCA CGTTTAAACG AATTTTACGA AGATACTCTG GTACTGGTTC

4700
TGAGATTAAT AAGCGATTCA ATGTGCAAAT CAAAAGAGAA AAGAAGCTAA TGGGTTTAAA
ACTCTAATTA TTCGCTAAGT TACACGTTTA GTTTTCTCTT TTCTTCGATT ACCCAAATTT 4750                                              4800
TATAACCAAA CAGAATAATA ATGCTATGTT TAGTTTTTCT AATTGAATCA TACCTTTGTG
ATATTGGTTT GTCTTATTAT TACGATACAA ATCAAAAAGA TTAACTTAGT ATGGAAACAC

4850
TCCATCACCT ACTTACCGGT CAGAATAAAG CAATTACGTC TGCAACCAAA AAGCACTAAG
AGGTAGTGGA TGAATGGCCA GTCTTATTTC GTTAATGCAG ACGTTGGTTT TTCGTGATTC

4900
ACTTTCGGTC AGACATGATC TCTAACATCG GACGAACCCT AAGATAACCA AAATAAACTA
TGAAAGCCAG TCTGTACTAG AGATTGTAGC CTGCTTGGGA TTCTATTGGT TTTATTTGAT

4950
TATCTTATAT TCAAATCTCT GTTTATTTTA TCCATTTATG TTTTCTTTCT TTCCCATAAT
ATAGAATATA AGTTTAGAGA CAAATAAAAT AGGTAAATAC AAAAGAAAGA AAGGGTATTA

5000
TTTTTTTGTG TCTCATCAGA CTCTCTTACC AAACTGAATT TATCAACATG GTTTTTTTTT
AAAAAAACAC AGAGTAGTCT GAGAGAATGG TTTGACTTAA ATAGTTGTAC CAAAAAAAAA 5050                                              5100
TGGCCACATC AAAATGGTGG TTTATAAAGT AGACTAATAC AAAAGACATT TCTGTTAATT
ACCGGTGTAG TTTTACCACC AAATATTTCA TCTGATTATG TTTTCTGTAA AGACAATTAA

5150
TCACTAACAA AAATAATCTT AGCAGTACTA TAGATTGGAA AAGGAAAAGC AAATCTAGCA
AGTGATTGTT TTTATTAGAA TCGTCATGAT ATCTAACCTT TTCCTTTTCG TTTAGATCGT

5200
GTAAGATTTA TCAAAACTAG CAGTAAGAGT TTTAGATATC ATGAAAACAT CACAAACGAG
CATTCTAAAT AGTTTTGATC GTCATTCTCA AAATCTATAG TACTTTTGTA GTGTTTGCTC

5250
TAGTGTTTTA CTTTACATTT TTAACCAATC ACAAGGGTAG TTCCGTAAGT TGGGAAAATC
ATCACAAAAT GAAATGTAAA AATTGGTTAG TGTTCCCATC AAGGCATTCA ACCCTTTTAG

5300
GTACGAGGCT TCACCTAGTT AAGGTTAGGT CACATGATTC CCTGAACTCG ATTTTATAAG
CATGCTCCGA AGTGGATCAA TTCCAATCCA GTGTACTAAG GGACTTGAGC TAAAATATTC 5350                                              5400
TAAAAAAGAA AAATTTATAA AATCAAAATT TTTTATATAA AAAAATCAGG TGGATTTATC
ATTTTTTCTT TTTAAATATT TTAGTTTTAA AAAATATATT TTTTAGTCC ACCTAAATAG

5450
AGACCCTACC ATCGAGATGT CGACACGTGT CCAAACTCAT TCATTGCCCT ACTATTTCT
TCTGGGATGG TAGCTCTACA GCTGTGCACA GGTTTGAGTA AGTAACGGGA TGATAAAGA

5500
GTTTAGGGTT GCAATCACTC ATCGCACACG CGCCATCTCC ACCTTCCATT ATTAATCTCT
CAAATCCCAA CGTTAGTGAG TAGCGTGTGC GCGGTAGAGG TGGAAGGTAA TAATTAGAGA

5550
CATTTTCAAC ATCACACTCT TACGAATCAT ACGATTTTAA TATCTCTGTC TCTCTCAACG
```

Fig. 3f

```
GTAAAAGTTG TAGTGTGAGA ATGCTTAGTA TGCTAAAATT ATAGAGACAG AGAGAGTTGC
           5600
TATTAAATAA AAATGGTTTT AAATGTTAGG GTTTTTTGTA GGATTTTCAA TTATTAATCT
ATAATTTATT TTTACCAAAA TTTACAATCC CAAAAAACAT CCTAAAAGTT AATAATTAGA
           5650                                              5700
CTATAATTCG ATGAACTAAG TAAAAAAGCA TCAAACTTTC TTGGCAGAAT CACATTTTTC
GATATTAAGC TACTTGATTC ATTTTTTCGT AGTTTGAAAG AACCGTCTTA GTGTAAAAAG
                                          5750
TCTAAACTAA ATATGGACTG AAATTGAAAA ATTAAACCAC TAGCTAGAAT AAAGTGTTGG
AGATTTGATT TATACCTGAC TTTAACTTTT TAATTTGGTG ATCGATCTTA TTTCACAACC
                               5800
TGAGAGTGGA ACTCTAATTT CTCTCCTTTA CTAATTATGT ATAAACACAA AAATGCACCA
ACTCTCACCT TGAGATTAAA GAGAGGAAAT GATTAATACA TATTTGTGTT TTTACGTGGT
                    5850
AATTTTTAGG TTTGAAAATA TCTAAGCATG GATAGGGTAA TTAACATTTT TTCTTTCAAT
TTAAAAATCC AAACTTTTAT AGATTCGTAC CTATCCCATT AATTGTAAAA AAGAAAGTTA
           5900
TTTGCAATAT TTGAATAAAT CCTATGAGGG TCTTTGGTAC ACAATAATTG GAGGGTATAT
AAACGTTATA AACTTATTTA GGATACTCCC AGAAACCATG TGTTATTAAC CTCCCATATA
      5950                                    6000
AGTTGAGTCT GAGAGTATAT TAGAAAGAGA ATATTTCAAG TAATGAAGCT GACATGTTTA
TCAACTCAGA CTCTCATATA ATCTTTCTCT TATAAAGTTC ATTACTTCGA CTGTACAAAT
                                     6050
TATGTACTTT GAGAGAAGTG TTGTGAGATT TGTACAAATG TATATGTACA CTTTAAAAAG
ATACATGAAA CTCTCTTCAC AACACTCTAA ACATGTTTAC ATATACATGT GAAATTTTTC
                          6100
CAATATAAGA TAGATAAAAA AAATATAAAG AAAAAAAGAA AGAAAGAAAG AAAGAAAGAG
GTTATATTCT ATCTATTTTT TTTATATTTC TTTTTTTCTT TCTTTCTTTC TTTCTTTCTC
                6150
AGAGGCTCAT ATATATATAG AATTGCTTGC AAGGAAAGAG AGAGAGAGAG ATTGAGATAT
TCTCCGAGTA TATATATATC TTAACGAACG TTCCTTTCTC TCTCTCTCTC TAACTCTATA
           6200
CTTTTGGGAG AGGAGAAAGA AAAAGAAAAT GGGAAGAGGG AGAGTAGAAT TGAAGAGGAT
GAAAACCCTC TCCTCTTTCT TTTTCTTTTA CCCTTCTCCC TCTCATCTTA ACTTCTCCTA
      6250                                          6300
AGAGAACAAG ATCAATAGGC AAGTGACGTT TGCAAAGAGA AGGAATGGTC TTTTGAAGAA
TCTCTTGTTC TAGTTATCCG TTCACTGCAA ACGTTTCTCT TCCTTACCAG AAAACTTCTT
                                6350
AGCATACGAG CTTTCAGTTC TATGTGATGC AGAAGTTGCT CTCATCATCT TCTCAAATAG
TCGTATGCTC GAAAGTCAAG ATACACTACG TCTTAACGA GAGTAGTAGA AGAGTTTATC
                    6400
AGGAAAGCTG TACGAGTTTT GCAGTAGTTC GAGGTATATA TCTACTTTTG TATATATATT
TCCTTTCGAC ATGCTCAAAA CGTCATCAAG CTCCATATAT AGATGAAAAC ATATATATAA
      6450
ACTTATAACA TAAACATTTT ATATACATAT TAAGTAACAC AAAAATGTCT TGTATGTATG
TGAATATTGT ATTTGTAAAA TATATGTATA ATTCATTGTG TTTTTACAGA ACATACATAC
```

Fig. 3g

```
                    6500
GGTCTCTCTG TGATGTGTTG TTGTGTCGTA CGTACGTGTT CTATCATATC CTTTTAAAAG
CCAGAGAGAC ACTACACAAC AACACAGCAT GCATGCACAA GATAGTATAG GAAAATTTTC 6550                                                6600
AAGCAAAGAG GAAAAAAAAT TTGGGATACC CCAAATCTGT ATCATTTTAT AACAAGTTTG
TTCGTTTCTC CTTTTTTTTA AACCCTATGG GGTTTAGACA TAGTAAAATA TTGTTCAAAC

6650
CTTTTTTGAT GTTCTTTTGT GTTTCTCTTT GATTTCCATT TTTGTTTTTG ATTTTTTTTC
GAAAAAACTA CAAGAAAACA CAAAGAGAAA CTAAAGGTAA AAACAAAAAC TAAAAAAAAG

6700
TATTTCTCTT TACATCTATC AAAGTTTTTT TTCTTATATT TTATTGCTTA TTTGTTTGTC
ATAAAGAGAA ATGTAGATAG TTTCAAAAAA AAGAATATAA AATAACGAAT AAACAAACAG

6750
TACTTAATTC ACATTATCTG AGAGAAGAAC AATCTATCTG ATATGAAATT AGGGTTAATT
ATGAATTAAG TGTAATAGAC TCTCTTCTTG TTAGATAGAC TATACTTTAA TCCCAATTAA

6800
TCTCTTGTGA GTACTCTTTA ATTCACATAA GCTTAAAGTT TCCACCTTTT GATTCTGGGG
AGAGAACACT CATGAGAAAT TAAGTGTATT CGAATTTCAA AGGTGGAAAA CTAAGACCCC 6850                                             6900
GTCGTCCAAT TCGATCAAAT CACTCAATTT TGTTGTCAGA TTGATATAAG TTCATAGGGG
CAGCAGGTTA AGCTAGTTTA GTGAGTTAAA ACAACAGTCT AACTATATTC AAGTATCCCC

6950
GATATTGTTT CCACGACAAT CCATTTTAGT AACCCTTAGG GGTTTCCAAT TTTGGGTTTT
CTATAACAAA GGTGCTGTTA GGTAAAATCA TTGGGAATCC CCAAAGGTTA AAACCCAAAA

7000
GAATTGACGC TAATGTCAAA TTCATCTAAA GTCCGTTGGA TATGTATACT TGGGGATGGG
CTTAACTGCG ATTACAGTTT AAGTAGATTT CAGGCAACCT ATACATATGA ACCCCTACCC

7050
ATTCATCCTT TTTTCTGGGT TCTTTAGATC TTCTCTTAAA AGACTAACAG ATTTTGTTGT
TAAGTAGGAA AAAAGACCCA AGAAATCTAG AAGAGAATTT TCTGATTGTC TAAAACAACA

7100
AAACCCTAGG AAACAGTTAA AAATCCCATT TTTAAAAACA TGTTTTGAAC TTGATGAGTA
TTTGGGATCC TTTGTCAATT TTTAGGGTAA AAATTTTTGT ACAAAACTTG AACTACTCAT 7150                                             7200
AGATTAATGG AAGAAATGAT GTTTTTGTGT GGTGTGAAGC ATGCTTCGGA CACTGGAGAG
TCTAATTACC TTCTTTACTA CAAAAACACA CCACACTTCG TACGAAGCCT GTGACCTCTC

7250
GTACCAAAAG TGTAACTATG GAGCACCAGA ACCCAATGTG CCTTCAAGAG AGGCCTTAGC
CATGGTTTTC ACATTGATAC CTCGTGGTCT TGGGTTACAC GGAAGTTCTC TCCGGAATCG

7300
AGTTGTACCC AATTCTCTTC TCTTTCTTCT AATTACCTTA ATTAATTACT CTCAATTTTT
TCAACATGGG TTAAGAGAAG AGAAAGAAGA TTAATGGAAT TAATTAATGA GAGTTAAAAA

7350
ACTTTGATTT TTAGAGTCAA ATGATTAATG TTATAATTTG TCATATACTT CAGGAACTTA
TGAAACTAAA AATCTCAGTT TACTAATTAC AATATTAAAC AGTATATGAA GTCCTTGAAT

7400
GTAGCCAGCA GGAGTATCTC AAGCTTAAGG AGCGTTATGA CGCCTTACAG AGAACCCAAA
```

Fig. 3h

```
CATCGGTCGT CCTCATAGAG TTCGAATTCC TCGCAATACT GCGGAATGTC TCTTGGGTTT 7450                                                    7500
GGTAAACTAA TTAGCTTCTT CAGCTACCTT CAGAGAGTGT TTGTTTTTTT AGTAGATTTT
CCATTTGATT AATCGAAGAA GTCGATGGAA GTCTCTCACA AACAAAAAAA TCATCTAAAA

7550
TTTGATGGTT TTGATGTTGA AATAGGAATC TGTTGGGAGA AGATCTTGGA CCTCTAAGTA
AAACTACCAA AACTACAACT TTATCCTTAG ACAACCCTCT TCTAGAACCT GGAGATTCAT

7600
CAAAGGAGCT TGAGTCACTT GAGAGACAGC TTGATTCTTC CTTGAAGCAG ATCAGAGCTC
GTTTCCTCGA ACTCAGTGAA CTCTCTGTCG AACTAAGAAG GAACTTCGTC TAGTCTCGAG

7650
TCAGGGTACT ACTTTGTTCA TCAATATCTT TATACACTGA TCTATTTCCA TAGTAAGATT
AGTCCCATGA TGAAACAAGT AGTTATAGAA ATATGTGACT AGATAAAGGT ATCATTCTAA

7700
AAATTTGGTG TTTAATTCTG CAGACACAGT TTATGCTTGA CCAGCTCAAC GATCTTCAGA
TTTAAACCAC AAATTAAGAC GTCTGTGTCA AATACGAACT GGTCGAGTTG CTAGAAGTCT 7750                                                    7800
GTAAGGTAAA TAAAGAAACA CTCATTCTCC TCTCTAAATT CCTCATCTAA AAGTAATGTA
CATTCCATTT ATTTCTTTGT GAGTAAGAGG AGAGATTTAA GGAGTAGATT TTCATTACAT

7850
ACCAAGAAAA CACAAATATT TGGAGCAGGA ACGCATGCTG ACTGAGACAA ATAAAACTCT
TGGTTCTTTT GTGTTTATAA ACCTCGTCCT TGCGTACGAC TGACTCTGTT TATTTTGAGA

7900
AAGACTAAGG GTAATTAATA TACATTCTCA TATCACCAAA TTAATGCATC ACTAAATTTG
TTCTGATTCC CATTAATTAT ATGTAAGAGT ATAGTGGTTT AATTACGTAG TGATTTAAAC

7950
GTTATAATGT GTGTGTGTAT ATACATATGT GACAGTTAGC TGATGGGTAT CAGATGCCAC
CAATATTACA CACACACATA TATGTATACA CTGTCAATCG ACTACCCATA GTCTACGGTG

8000
TCCAGCTGAA CCCTAACCAA GAAGAGGTTG ATCACTACGG TCGTCATCAT CATCAACAAC
AGGTCGACTT GGGATTGGTT CTTCTCCAAC TAGTGATGCC AGCAGTAGTA GTAGTTGTTG 8050                                                    8100
AACAACACTC CCAAGCTTTC TTCCAGCCTT TGGAATGTGA ACCCATTCTT CAGATCGGGT
TTGTTGTGAG GGTTCGAAAG AAGGTCGGAA ACCTTACACT TGGGTAAGAA GTCTAGCCCA

8150
AACTTTAGAC TAGTATAACC AATTTGATTT GAGTTCTATT ATAAGCTTTT CTTAAGAAAG
TTGAAATCTG ATCATATTGG TTAAACTAAA CTCAAGATAA TATTCGAAAA GAATTCTTTC

8200
TATCTCAAAC TACTAAATTT TATGGAGCAG GTATCAGGGG CAACAAGATG GAATGGGAGC
ATAGAGTTTG ATGATTTAAA ATACCTCGTC CATAGTCCCC GTTGTTCTAC CTTACCCTCG

8250
AGGACCAAGT GTGAATAATT ACATGTTGGG TTGGTTACCT TATGACACCA ACTCTATTTG
TCCTGGTTCA CACTTATTAA TGTACAACCC AACCAATGGA ATACTGTGGT TGAGATAAAC

8300
AATCTTTCTC ACTTAATCAA TCCCTCTCTT TTTTTTTTGA CATTTTTAAG ATGATGTTTC
TTAGAAAGAG TGAATTAGTT AGGGAGAGAA AAAAAAAACT GTAAAAATTC TACTACAAAG
```

Fig. 3i

```
                8350                                                                    8400
       TATTTTATTA CCTCTCTCAT GTTTTCTGTC TTGTGTGCAT GTGTGTGTGT AATGTTTATG
       ATAAAATAAT GGAGAGAGTA CAAAAGACAG AACACACGTA CACACACACA TTACAAATAC

8450
       CCCTTCTATT ATTCAATAAT TTTTTCGACA ATTTTGCTTC CTATTTTTAC CCATTACTCC
       GGGAAGATAA TAAGTTATTA AAAAAGCTGT TAAAACGAAG GATAAAAATG GGTAATGAGG

8500
       TAAACTTCCT GATCCAGTTT CTTTTAAAAT AACTCCCATT TTATGCATGT TATCTAACCA
       ATTTGAAGGA CTAGGTCAAA GAAAATTTTA TTGAGGGTAA AATACGTACA ATAGATTGGT

8550
       ATTCTCTTAA CTATGATTTA TGGTACGATA TAACTCACAG TCTCACACTA TCTATTTGGT
       TAAGAGAATT GATACTAAAT ACCATGCTAT ATTGAGTGTC AGAGTGTGAT AGATAAACCA

8600
       GTTTTTTTGT TTGAGTCTTG AGAAGGGACC GCTTGTTTAT CTCTCTTGTT AAAGAGCAAC
       CAAAAAAACA AACTCAGAAC TCTTCCCTGG CGAACAAATA GAGAGAACAA TTTCTCGTTG 8650                                                        8700
       TCACTGGCCA CTGCTTATGT ATCTGTAGGC CCCACCTATA TCATTTTGGC TATATCTATA
       AGTGACCGGT GACGAATACA TAGACATCCG GGGTGGATAT AGTAAAACCG ATATAGATAT

8750
       CTTTTGTAGA GGGAGTATTA CTATAGAGAA GAAGATAAAT TTGGTTCTAA TATATCTTGC
       GAAAACATCT CCCTCATAAT GATATCTCTT CTTCTATTTA AACCAAGATT ATATAGAACG

8800
       AGGTAGTTGA TATTCTCAAT TATCATGAAG ATTTGATAGA CAAGTTTATC AGATACCTTA
       TCCATCAACT ATAAGAGTTA ATAGTACTTC TAAACTATCT GTTCAAATAG TCTATGGAAT

8850
       AACATAGGTT TAAGATCTCA ATTGAAATGT GAATTCACCC GACGATTAGA GTTACGATCT
       TTGTATCCAA ATTCTAGAGT TAACTTTACA CTTAAGTGGG CTGCTAATCT CAATGCTAGA

8900
       AAGGAAGCGT TTCTTGAATT TTGAGTTTGT TTGATCAAGA GTAGAATGCT TTTCTATTAC
       TTCCTTCGCA AAGAACTTAA AACTCAAACA AACTAGTTCT CATCTTACGA AAAGATAATG 8950                                                    9000
       TAAGGTTGTT AATGCTTATA TTCCATGACC AAGGCCAAGA GAACAAACAA AAACATGGTG
       ATTCCAACAA TTACGAATAT AAGGTACTGG TTCCGGTTCT CTTGTTTGTT TTTGTACCAC

9050
       CCTCTTGATG TATAGTAATG GCTCTTAATG GTCATATACA GAGAAAAAAA GATTAATGTC
       GGAGAACTAC ATATCATTAC CGAGAATTAC CAGTATATGT CTCTTTTTTT CTAATTACAG

9100
       GTTGCACAAG CTTGAAGTTA CTTACTCCTC GTCTTCCTCA TTAGTGTCTT CGTCTTCCTC
       CAACGTGTTC GAACTTCAAT GAATGAGGAG CAGAAGGAGT AATCACAGAA GCAGAAGGAG

9150
       ATCCTCATCG CTCCCAATAT AGGGCTTCAT CTACTTGAAA ACCAAATGCT CATGCAGTGG
       TAGGAGTAGC GAGGGTTATA TCCCGAAGTA GATGAACTTT TGGTTTACGA GTACGTCACC

9200
       AAAAAGATAA CAGAGGTTCA AATTAAGGCA AACAAAACTA CAAGTGAGAA AGGGAAACTA
       TTTTTCTATT GTCTCCAAGT TTAATTCCGT TTGTTTTGAT GTTCACTCTT TCCCTTTGAT 9250                                                   9300
       CAAGTGGTAA GATGTAATGT TTTGACTCAA AACCAGATCA GACAATGAAA AAAAGTATTG
```

Fig. 3j

```
              GTTCACCATT CTACATTACA AAACTGAGTT TTGGTCTAGT CTGTTACTTT TTTTCATAAC
                                                  9350
              ATACAAAAAG TCCATCCGGA AGCATAATTA CCGCTTGCAG GATGTCATCA GAGATGTCTG
              TATGTTTTTC AGGTAGGCCT TCGTATTAAT GGCGAACGTC CTACAGTAGT CTCTACAGAC
                                      9400
              TTAGTCGGCC AATGGCATAG ATGGTGAGCG GACCAGAGTA GCGTAAATCC TCTAAATACT
              AATCAGCCGG TTACCGTATC TACCACTCGC CTGGTCTCAT CGCATTTAGG AGATTTATGA
                                 9450
              GTCTAAAAGC CGGACCGACC CGACAAGGAT CACAGTCAAG GGGAATAGGA CACCTATTGA
              CAGATTTTCG GCCTGGCTGG GCTGTTCCTA GTGTCAGTTC CCCTTATCCT GTGGATAACT
                     9500
              TATCCCAAAA GACTGTTGTT ACAGCCACAT CATCCTTGTC CAACTGGGTA GCCCAAAGGG
              ATAGGGTTTT CTGACAACAA TGTCGGTGTA GTAGGAACAG GTTGACCCAT CGGGTTTCCC 9550                                                 9600
              AAACTAGTTG TGGTAAGAGC TTGTTTGACT CAAAAAATGG CTAACTAGGA TGATGCTGAA
              TTTGATCAAC ACCATTCTCG AACAAACTGA GTTTTTTACC GATTGATCCT ACTACGACTT
                                                  9650
              TTACCATCTG TTCATGTTTT TGACTAGAGA GATGGGTAGT GAAATTTTCA AAGCCTTTGC
              AATGGTAGAC AAGTACAAAA ACTGATCTCT CTACCCATCA CTTTAAAAGT TTCGGAAACG
                                      9700
              AAAACGCCTG TGGGACCTGT TTCAGAAAAA GACTTAAAAG ACTTGAGACT CAAGGAAAAT
              TTTTGCGGAC ACCCTGGACA AAGTCTTTTT CTGAATTTTC TGAACTCTGA GTTCCTTTTA
                                 9750
              AATATCCATT ATATAAAGAT GACAACAAAT ATTAACGGAA GTAGGAGTGA TTGAGAACGA
              TTATAGGTAA TATATTTCTA CTGTTGTTTA TAATTGCCTT CATCCTCACT AACTCTTGCT
                     9800
              TTCTAGTAGA AGAGACGGCT CGCAGGACGT CGTTTATAAT AGGCCAATGG CAGAGATAGT
              AAGATCATCT TCTCTGCCGA GCGTCCTGCA GCAAATATTA TCCGGTTACC GTCTCTATCA 9850                                                    9900
              GAGAGGACCG GAGTAGCCTA AATTCTTTAA ATGTCGTTTG ATACACGGAC CAACTAGACG
              CTCTCCTGGC CTCATCGGAT TTAAGAAATT TACAGCAAAC TATGTGCCTG GTTGATCTGC
                                                  9950
              AGCATCATAC TCAGAGGGAA CCGGACACGT CTTGATATCC CAGAAGACCG ATGTTACGGC
              TCGTAGTATG AGTCTCCCTT GGCCTGTGCA GAACTATAGG GTCTTCTGGC TACAATGCCG
                                           10000
              CTTAGCTTGC TGCCGCGTTG CCTTCATCAT CATCTTCTCC TTTTAATCTA TAACGGAAAT
              GAATCGAACG ACGGCGCAAC GGAAGTAGTA GTAGAAGAGG AAAATTAGAT ATTGCCTTTA
                                 10050
              CAAACATCAG ATAAAGCATT CGAAAAGATA GATTGACACA GGTTAAATCA TCCACTTCAG
              GTTTGTAGTC TATTTCGTAA GCTTTTCTAT CTAACTGTGT CCAATTTAGT AGGTGAAGTC
                            10100
              AGAAAAAGAG AGGGACATGG CCGTAAACAA TGAGATAAGG ATCGGCCTAA TGTTTATAAT
              TCTTTTTCTC TCCCTGTACC GGCATTTGTT ACTCTATTCC TAGCCGGATT ACAAATATTA
                  10150                                              10200
              GGGCTTGCGT TTAATGGGCC TACAGTTTCT TGAATCAGCC TTATGCATGA GTCCTAGTAT
              CCCGAACGCA AATTACCCGG ATGTCAAAGA ACTTAGTCGG AATACGTACT CAGGATCATA
```

Fig. 3k

```
                                                      10250
TTTATCAACT TTTTTTTTTC ATCTTTCTTT AGTTACAATA GATTTAAAGT GTTTTTTGTT
AAATAGTTGA AAAAAAAAAG TAGAAAGAAA TCAATGTTAT CTAAATTTCA CAAAAAACAA

10300
AATGCCATTG CAAAATTTGG TAACTGTTTA TAACATTGTT CCTCACTTCA AAATTTAAAG
TTACGGTAAC GTTTTAAACC ATTGACAAAT ATTGTAACAA GGAGTGAAGT TTTAAATTTC

10350
CACCATTAAT AAAAGCTATA CATATAATTA TAACTTGGGT TTTGTGCAAA AAAAACAAAC
GTGGTAATTA TTTTCGATAT GTATATTAAT ATTGAACCCA AAACACGTTT TTTTTGTTTG

10400
AAATTAACCT TTCATTTTAA ATAAATGCAA TTCAATACCG CAATATCAAA AGTAACCCGT
TTTAATTGGA AAGTAAAATT TATTTACGTT AAGTTATGGC GTTATAGTTT TCATTGGGCA 10450                                                10500
ATAACCTTTA TTCGTGTATA GATTTTAGAA ACAGTATAAG TCAAATTATC AAAACTATGT
TATTGGAAAT AAGCACATAT CTAAAATCTT TGTCATATTC AGTTTAATAG TTTTGATACA

10550
TGTTTTAAGC ATTTTAAAAA TAAGAATAAT AATAATGTTG AAGGGTGGAT TTGAACCCAT
ACAAAATTCG TAAAATTTTT ATTCTTATTA TTATTACAAC TTCCCACCTA AACTTGGGTA

10600
GAACTATAGA ACAAACCAAA GCATGCATAA CCACATGCGC CGAACAAACC AAAAACTCAT
CTTGATATCT TGTTTGGTTT CGTACGTATT GGTGTACGCG GCTTGTTTGG TTTTTGAGTA

10650
GGCTTTGTTA AACATATAAA AATATTCGAA TAAAAATGT GGGGAACTTG TTACCAGTTT
CCGAAACAAT TTGTATATTT TTATAAGCTT ATTTTTTACA CCCCTTGAAC AATGGTCAAA

10700
TGGTTCTTTT TGGAGCCATT TTTTTCAACA CAGATATTGT TAAGGAGTTT CAGGTAAAAC
ACCAAGAAAA ACCTCGGTAA AAAAAGTTGT GTCTATAACA ATTCCTCAAA GTCCATTTTG 10750                                                   10800
TGTATATTAT GCAGGGAACC ACAGTAGGCT ATAATGAAAG TCACACTGTG AAGTTAGCAG
ACATATAATA CGTCCCTTGG TGTCATCCGA TATTACTTTC AGTGTGACAC TTCAATCGTC

10850
ACAAGTTTTT ACTTAAAGAT GTGAGTTGTG ATCTTTTTGA TGTAAGTCTT GATGTATATG
TGTTCAAAAA TGAATTTCTA CACTCAACAC TAGAAAAACT ACATTCAGAA CTACATATAC

10900
TTGACAAATT ATATAAGTTT GTATTGCATA TTCTATGACT TACGAAGTTT CTATGCAAGA
AACTGTTTAA TATATTCAAA CATAACGTAT AAGATACTGA ATGCTTCAAA GATACGTTCT

10950
AAAGCCGGGA GAAAATTTCC GTCAAGTAAC TAAGAGATCG TAATTCTTGT CTGAAGAACA
TTTCGGCCCT CTTTTAAAGG CAGTTCATTG ATTCTCTAGC ATTAAGAACA GACTTCTTGT

11000
ACCCTTTTTT ATTATTTGAG TTTAGGTTGC CAACAGTGAA CAAAGGGACG AGATACCATA
TGGGAAAAAA TAATAAACTC AAATCCAACG GTTGTCACTT GTTTCCCTGC TCTATGGTAT 11050                                                11100
TGACAAATAT CCTCTAACGC CATTTCAACA GTTAATCAAC AGTGTCGGCT ATATGCATGT
ACTGTTTATA GGAGATTGCG GTAAAGTTGT CAATTAGTTG TCACAGCCGA TATACGTACA

11150
           GCTAACAATG CACAAGAACA TTGTCACCAT CCCGTGAATA TGAATATTAA TGATTATGAA
```

Fig. 31

```
CGATTGTTAC GTGTTCTTGT AACAGTGGTA GGGCACTTAT ACTTATAATT ACTAATACTT
                                  11200
CGAGTTTGTA GAGTTCCAAG AGGAAGGTAC TACCTTCTCA TACTCATTGA TCATATATTT
GCTCAAACAT CTCAAGGTTC TCCTTCCATG ATGAAGAGT  ATGAGTAACT AGTATATAAA
                       11250
TGTTTCTTGT TTGTTTTAGT AACTAGGGTT ATTCGGATTG TTTTTCAAAA TAATAGTAAT
ACAAAGAACA AACAAAATCA TTGATCCCAA TAAGCCTAAC AAAAAGTTTT ATTATCATTA
            11300
ATGTCAACTA TATTTATAAA AAAAAAAACT AAATAACTTT TGTACAATTG ATCATTTTTT
TACAGTTGAT ATAAATATTT TTTTTTTTGA TTTATTGAAA ACATGTTAAC TAGTAAAAAA
   11350                                                 11400
AAATATATCA TAAAGATTCA TCAATATATG AACATATATT TTTAACAATT ACACTAATTG
TTTATATAGT ATTTCTAAGT AGTTATATAC TTGTATATAA AAATTGTTAA TGTGATTAAC
                                       11450
GCTATATAGT GTATAGTTCC TTTTGTGGAG AGGTTTAAGT TCAGTTCAGA GATTATTGTA
CGATATATCA CATATCAAGG AAAACACCTC TCCAAATTCA AGTCAAGTCT CTAATAACAT
                               11500
CTTGGTAAAA TATTTGTCCT TGTTAATTAG TTCATCTTCT AGAATACAGA TTTGGGCCAT
GAACCATTTT ATAAACAGGA ACAATTAATC AAGTAGAAGA TCTTATGTCT AAACCCGGTA
                  11550
GTAGTTTCCC AGAAAACACC GGAAAAAAAA TTCACACTTC ACACCAGAAA CAATAAACGA
CATCAAAGGG TCTTTTGTGG CCTTTTTTTT AAGTGTGAAG TGTGGTCTTT GTTATTTGCT
        11600
GGAACAGAGC CCAAACTCAT CCCTATAATT GGGCCCAAAA AAAGCAGAGC AAACCAAACC
CCTTGTCTCG GGTTTGAGTA GGGATATTAA CCCGGGTTTT TTTCGTCTCG TTTGGTTTGG
   11650                                                 11700
AAAATCAAGT AAATCCATTT ACAAATATGC TTTATAATTA TTATTTTTCT CAACCACAAA
TTTTAGTTCA TTTAGGTAAA TGTTTATACG AAATATTAAT AATAAAAAGA GTTGGTGTTT
                                       11750
TATGCTTTAT AATTTATGTA AATGTTATAT GAATTATTTA CGATTTATTT TAATTACTTT
ATACGAAATA TTAAATACAT TTACAATATA CTTAATAAAT GCTAAATAAA ATTAATGAAA
                            11800
ATCTTGGAAT TATCTTACGA AGTTAATGAA AATATTTTAA ATATCTAATT TATATATGTC
TAGAACCTTA ATAGAATGCT TCAATTACTT TTATAAAATT TATAGATTAA ATATATACAG
                 11850
TGGACTAAAA TAAATAGAAA TATCTGTATT CCAATCATCA CAAAAAAAAA ATTCTCATCA
ACCTGATTTT ATTTATCTTT ATAGACATAA GGTTAGTAGT GTTTTTTTTT TAAGAGTAGT
           11900
TCTTTGATAT ATAGAAAGTT TTTAAAATTT CAGTTTCACA GATTTACCA  ATTATAGTTT
AGAAACTATA TATCTTTCAA AAATTTTAAA GTCAAAGTGT CTAAAATGGT TAATATCAAA
    11950                                                12000
TATAAGCTTA TGCTAATTAT GTGATCAATG CAAACAAAAG TTGACAATAA TAAAATGAAG
ATATTCGAAT ACGATTAATA CACTAGTTAC GTTTGTTTTC AACTGTTATT ATTTTACTTC
                                         12050
TCAAATATGA TAGATTCCTA CTATAAATAT AGACTCGTGA ATAATACTCG AATCAGTCTC
AGTTTATACT ATCTAAGGAT GATATTTATA TCTGAGCACT TATTATGAGC TTAGTCAGAG
```

Fig. 3m

```
                              12100
TGAGGTTTTG CTGGAAAAGA AAAACCGAAG AGCTCAAAAC AGAGTGCGTT TGTTTCTGGG
ACTCCAAAAC GACCTTTTCT TTTTGGCTTC TCGAGTTTTG TCTCACGCAA ACAAAGACCC

12150
AATCTTCAAG CCTCTCACTT GCGAAGACGA AGCTTACTCG TAAGGTGATT ATCTTCTTCT
TTAGAAGTTC GGAGAGTGAA CGCTTCTGCT TCGAATGAGC ATTCCACTAA TAGAAGAAGA

12200
TCTTCTTCTT TTCAATTCCT TTTTCGTTCA TCTGAAATGT GAAATCATGT GACGTGACGA
AGAAGAAGAA AAGTTAAGGA AAAAGCAAGT AGACTTTACA CTTTAGTACA CTGCACTGCT 12250                                                    12300
TTAGGTTAAC GATCGAATTT CTTAATTTCG TATATGATTA TCTTCTAGTT TCTTGATCAG
AATCCAATTG CTAGCTTAAA GAATTAAAGC ATATACTAAT AGAAGATCAA AGAACTAGTC

12350
CACATCTTGT TGTTTTCTTT CAATCGAGAC TGATTCTAGA TGTTCTTAAG GATCTTGTTC
GTGTAGAACA ACAAAAGAAA GTTAGCTCTG ACTAAGATCT ACAAGAATTC CTAGAACAAG

12400
GATGAACTTT GCATGAATCA TCCATATCGA CGAACTGGTC TGATCTTCTT GTTGTTATGG
CTACTTGAAA CGTACTTAGT AGGTATAGCT GCTTGACCAG ACTAGAAGAA CAACAATACC

12450
ATTAAGTTTC TTGAGATACA AGAAAGGCTT CAATGATCAA TCTGATCTGT TTTGATGAAC
TAATTCAAAG AACTCTATGT TCTTTCCGAA GTTACTAGTT AGACTAGACA AAACTACTTG

12500
ACAAATCTTT ATCTTTGAAC CATGGATAAG GTCAATTTCA CACCATGGCT GGAGGAAGTT
TGTTTAGAAA TAGAAACTTG GTACCTATTC CAGTTAAAGT GTGGTACCGA CCTCCTTCAA 12550                                                    12600
TATCACCGGC GTCATCTTTG GAAGATGTAA AGGCATACGT CAATGCTGTG GAGGTCGCAT
ATAGTGGCCG CAGTAGAAAC CTTCTACATT TCCGTATGCA GTTACGACAC CTCCAGCGTA

12650
TGCAGGAAAT GGAACCTGCA AGATTTGGAA TGTTTGTAAG ACTCTTTCGT GGTTTTACAG
ACGTCCTTTA CCTTGGACGT TCTAAACCTT ACAAACATTC TGAGAAAGCA CCAAAATGTC

12700
CTCCTAGGTG TGTTTGGTTT GCTCTTAAAC AGTCTAAAGA ACAATGACAC ATGTGAGAAT
GAGGATCCAC ACAAACCAAA CGAGAATTTG TCAGATTTCT TGTTACTGTG TACACTCTTA

12750
TGATTCTGAT GTTATTTTTC TCTTTGTAGG ATCGGTATGC CTACTTTCAG TGCACGCATG
ACTAAGACTA CAATAAAAAG AGAAACATCC TAGCCATACG GATGAAAGTC ACGTGCGTAC

12800
CAGGACCTCT TGAAAGATCA CCCGAGTCTG TGTCTTGGTT TAAATGTCTT ACTTCCACCT
GTCCTGGAGA ACTTTCTAGT GGGCTCAGAC ACAGAACCAA ATTTACAGAA TGAAGGTGGA 12850                                          12900
GAGTATCAGT TAACCATACC TCCCGAGGCT AGCGAAGAGT TCATAAGGT GGTTGGAAGA
CTCATAGTCA ATTGGTATGG AGGGCTCCGA TCGCTTCTCA AGTATTCCA CCAACCTTCT

12950
AGCGTACCAG TACCACCAAA GGTGGTTGGA AGAAGTCTAC CACGTCCGGA GCCTACCATA
TCGCATGGTC ATGGTGGTTT CCACCAACCT TCTTCAGATG GTGCAGGCCT CGGATGGTAT

13000
GATGATGCGA CTTCATACCT TATTGCTGTG AAGGAAGCCT TTCATGATGA ACCTGCAAAA
```

Fig. 3n

```
CTACTACGCT GAAGTATGGA ATAACGACAC TTCCTTCGGA AAGTACTACT TGGACGTTTT
                      13050
TATGGGGAAA TGCTTAAGCT CTTGAAAGAT TTTAAAGCTC GCAGGTATGT ATTAGTTCTT
ATACCCCTTT ACGAATTCGA GAACTTTCTA AAATTTCGAG CGTCCATACA TAATCAAGAA
           13100
TTCTCCATGT TATGTTTGAT TTTTTCAGTC TACAGAACAA ACACATTATG TGAATTGATT
AAGAGGTACA ATACAAACTA AAAAAGTCAG ATGTCTTGTT TGTGTAATAC ACTTAACTAA
      13150                                                  13200
CTGATGTTAC TAAGTCTCTT TGTAGAGTCG ATGCCGCTTG TGTCATTGCT AGGGTGGAGG
GACTACAATG ATTCAGAGAA ACATCTCAGC TACGGCGAAC ACAGTAACGA TCCCACCTCC

AACTCATGAA AGATCACTTG AATCTGCTTT TTGGTTTCTG TGTCTTCCTT TCAGCTACAA
TTGAGTACTT TCTAGTGAAC TTAGACGAAA AACCAAAGAC ACAGAAGGAA AGTCGATGTT
                      13300
CGAGTTTTAC CACGAAGCTT AAGGTATAGA GTGCTTATAG TTACCATTTG ATGTTTCCTA
GCTCAAAATG GTGCTTCGAA TTCCATATCT CACGAATATC AATGGTAAAC TACAAAGGAT
                      13350
TATGTTAACT TGTGGTTTAA GTAACAAAAT TGTCCATGTG CAGGCAAGGT TTCAGGGCGA
ATACAATTGA ACACCAAATT CATTGTTTTA ACAGGTACAC GTCCGTTCCA AAGTCCCGCT
           13400
TGGTAGTCAA GTAGTTGACT CAGTTCTTCA GATAATGAGA ATGTACGGTG AGGGAAACAA
ACCATCAGTT CATCAACTGA GTCAAGAAGT CTATTACTCT TACATGCCAC TCCCTTTGTT
      13450                                                  13500
GTCCAAACAT GATGCGTATC AGGAGGTAGG CTTCTTGGTA GGATACTTTG TGTTGTGTGT
CAGGTTTGTA CTACGCATAG TCCTCCATCC GAAGAACCAT CCTATGAAAC ACAACACACA
                           13550
TGCACTTTCT TAGTTCTTTG GTTTGATTTG CTTTGTTATC TTTTGCAGGT CGTTGCACTT
ACGTGAAAGA ATCAAGAAAC CAAACTAAAC GAAACAATAG AAAACGTCCA GCAACGTGAA
                 13600
GTTCAGGGTC ATGACGATTT AGTCATGGAG CTTTCACAAA TTTTGACTGA TCCACCTACT
CAAGTCCCAG TACTGCTAAA TCAGTACCTC GAAAGTGTTT AAAACTGACT AGGTGGATGA
                 13650
GGAGTCTAGA GATAGCCAGA TAGCTAAGGA GAGTACTGGA AGACTGTAAT ATACCATAAG
CCTCAGATCT CTATCGGTCT ATCGATTCCT CTCATGACCT TCTGACATTA TATGGTATTC
           13700
AGACGAAAAA GAAAGTAGAG CTTCTCACGA AAAGAGAGTG TTTTTAGTTT TCTTTTGCAA
TCTGCTTTTT CTTTCATCTC GAAGAGTGCT TTTCTCTCAC AAAAATCAAA AGAAAACGTT
      13750                                                  13800
ACATTAGAGT TTTGTTTGAT TAACATGACA TTCAAAAATA TGCTATGCTT CTATGTTGAG
TGTAATCTCA AAACAAACTA ATTGTACTGT AAGTTTTTAT ACGATACGAA GATACAACTC
                                13850
GTGTACAATG AATTGGTGTA TAAGAGACTA AAAGAGAGTG TATAGTTTCT TTGTTGAGGT
CACATGTTAC TTAACCACAT ATTCTCTGAT TTTCTCTCAC ATATCAAAGA AACAACTCCA

13900
TTCTTTTATG TTGAGGTGTT CAATATGCTA TTTTCAGGGT AATCTTTTTA TAAGAAACTG
AAGAAAATAC AACTCCACAA GTTATACGAT AAAAGTCCCA TTAGAAAAAT ATTCTTTGAC
```

Fig. 3o

```
                              13950
AGAAGGGAAA  CACTCAAAAA  ACAGAGTTCA  ACGTAGAAAC  AAAAACAGAG  AGGTGAACTC
TCTTCCCTTT  GTGAGTTTTT  TGTCTCAAGT  TGCATCTTTG  TTTTTGTCTC  TCCACTTGAG

14000
ATGAAAGATC  AATTTAACCT  GCTTGTGATG  ATTGGCTTAT  CAAGAGAATT  GAAGAGATTC
TACTTTCTAG  TTAAATTGGA  CGAACACTAC  TAACCGAATA  GTTCTCTTAA  CTTCTCTAAG 14050                                                  14100
ACGATTACAC  AAATTCAATT  CTTAAAGACA  AGAGTAGACT  GCTAATTCTT  ATTAAGGCTG
TGCTAATGTG  TTTAAGTTAA  GAATTTCTGT  TCTCATCTGA  CGATTAAGAA  TAATTCCGAC

14150
TTAATGCTTC  TTGAGAGCAT  TGACCTTTTC  CCTGAGGTAA  TAAAGCTTGG  CTCTTCTTAC
AATTACGAAG  AACTCTCGTA  ACTGGAAAAG  GGACTCCATT  ATTTCGAACC  GAGAAGAATG

14200
TTTCTTCTTG  TCCACCACCT  TAATCACCCT  CAGGTTTGGG  GAATACCTGT  CACCAAAACA
AAAGAAGAAC  AGGTGGTGGA  ATTAGTGGGA  GTCCAAACCC  CTTATGGACA  GTGGTTTTGT

14250
CCTCCACTTA  CATCAGTATT  TTCCATGACC  AAGGCAAACA  AAGAGAACAT  ACAAAACATG
GGAGGTGAAT  GTAGTCATAA  AAGGTACTGG  TTCCGTTTGT  TTCTCTTGTA  TGTTTTGTAC

14300
GTGGCTCTTG  ATTATAATAA  TGGCTCTTAA  TGGTCATATA  CAAAAGTCTG  AGAGAAAAAG
CACCGAGAAC  TAATATTATT  ACCGAGAATT  ACCAGTATAT  GTTTTCAGAC  TCTCTTTTTC 14350                                                  14400
ATTAAAGTGG  CTGCACAAGC  TTGAAGCTTG  AAGTTACTTA  CAAGGGGAAC  ATGGATTCGA
TAATTTCACC  GACGTGTTCG  AACTTCGAAC  TTCAATGAAT  GTTCCCCTTG  TACCTAAGCT

14450
CGCCCACTCC  AGCAACAAGC  CTTCTAATTC  TAAATGTTGA  GTTGAGACCA  GCATTACGCC
GCGGGTGAGG  TCGTTGTTCG  GAAGATTAAG  ATTTACAACT  CAACTCTGGT  CGTAATGCGG

14500
TTGCTATGAC  GACGCCTTTT  ACGATTGATA  CACGCCTCTT  GTTCTCAGGC  ACTTCCTGTT
AACGATACTG  CTGCGGAAAA  TGCTAACTAT  GTGCGGAGAA  CAAGAGTCCG  TGAAGGACAA

14550
CAAACAAAGT  AAATGAAAGG  TTTCACTTAG  AAGATGAAAG  ATAGTTTGAT  CTTACTCACC
GTTTGTTTCA  TTTACTTTCC  AAAGTGAATC  TTCTACTTTC  TATCAAACTA  GAATGAGTGG

14600
CAAGAAAAAG  AAATTACAAC  CTAGGCCAAC  AGTAGTTACC  ACTTTTAGCT  GCACAATGTA
GTTCTTTTTC  TTTAATGTTG  GATCCGGTTG  TCATCAATGG  TGAAAATCGA  CGTGTTACAT 14650                                                  14700
ACCAGGCTTT  ATCTCTGGAA  TCTCTCTAAG  AGTTCTCACT  TCCTCAACTG  CTTCCTTGTC
TGGTCCGAAA  TAGAGACCTT  AGAGAGATTC  TCAAGAGTGA  AGGAGTTGAC  GAAGGAACAG

14750
TACAATCTGC  AGAGGATTGT  GACATCGGTG  CTTCCTTGTC  TACATGATAT  ATCTAAATAC
ATGTTAGACG  TCTCCTAACA  CTGTAGCCAC  GAAGGAACAG  ATGTACTATA  TAGATTTATG

14800
AAGTGTCAAG  TTCGAGTTGT  AGTACCTGCA  TAATATGCTT  AGCGGTTTTA  TCAAGCCGCT
TTCACAGTTC  AAGCTCAACA  TCATGGACGT  ATTATACGAA  TCGCCAAAAT  AGTTCGGCGA

14850
TAAACTTGAT  TCTCTGAGGC  ACAACACAAT  CTGACTCAGG  GGATCCTTGA  ACAGAATCTC
```

Fig. 3p

```
ATTTGAACTA AGAGACTCCG TGTTGTGTTA GACTGAGTCC CCTAGGAACT TGTCTTAGAG
           14900
CAGTGGTGGA AAAACACCTC GACGAAAAGT TTTGTTTCTG CCAAAAAAAT ATTCCCAAGA
GTCACCACCT TTTTGTGGAG CTGCTTTTCA AAACAAAGAC GGTTTTTTTA TAAGGGTTCT
```

Sequence Range: -12 to 815

```
                                                      38
       CCCGGATCCA AAATGGGAAG AGGGAGAGTA GAATTGAAGA GGATAGAGAA CAAGATCAAT
                   K  M  G  R  G  R  V  E  L  K  R  I  E  N  K  I  N>

88
       AGGCAAGTGA CGTTTGCAAA GAGAAGGAAT GGTCTTTTGA AGAAAGCATA CGAGCTTTCA
       R  Q  V  T  F  A  K  R  R  N  G  L  L  K  K  A  Y  E  L  S>

138
       GTTCTATGTG ATGCGGAAGT TGCTCTCATC ATCTTCTCAA ATAGAGGAAA GCTGTACGAG
       V  L  C  D  A  E  V  A  L  I  I  F  S  N  R  G  K  L  Y  E>

188
       TTTTGCAGTA GTTCGAGCAT GCTTCGGACA CTGGAGAGGT ACCAAAAGTG TAACTATGGA
       F  C  S  S  S  M  L  R  T  L  E  R  Y  Q  K  C  N  Y  G>

238                                         288
       GCACCAGAAC CCAATGTGCC TTCAAGAGAG GCCTTAGCAG AACTTAGTAG CCAGCAGGAG
       A  P  E  P  N  V  P  S  R  E  A  L  A  E  L  S  S  Q  Q  E>

338
       TATCTCAAGC TTAAGGAGCG TTATGACGCC TTACAGAGAA CCCAAAGGAA TCTGTTGGGA
       Y  L  K  L  K  E  R  Y  D  A  L  Q  R  T  Q  R  N  L  L  G>

388
       GAAGATCTTG GACCTCTAAG TACAAAGGAG CTTGAGTCAC TTGAGAGACA GCTTGATTCT
       E  D  L  G  P  L  S  T  K  E  L  E  S  L  E  R  Q  L  D  S>

438
       TCCTTGAAGC AGATCAGAGC TCTCAGGACA CAGTTTATGC TTGACCAGCT CAACGATCTT
       S  L  K  Q  I  R  A  L  R  T  Q  F  M  L  D  Q  L  N  D  L>

488
       CAGAGTAAGG AACGCATGCT GACTGAGACA AATAAAACTC TAAGACTAAG GTTAGCTGAT
       Q  S  K  E  R  M  L  T  E  T  N  K  T  L  R  L  R  L  A  D>

538                                     588
       GGGTATCAGA TGCCACTCCA GCTGAACCCT AACCAAGAAG AGGTTGATCA CTACGGTCGT
       G  Y  Q  M  P  L  Q  L  N  P  N  Q  E  E  V  D  H  Y  G  R>

CATCATCATC AACAACAACA ACACTCCCAA GCTTTCTTCC AGCCTTTGGA ATGTGAACCC
       H  H  H  Q  Q  Q  Q  H  S  Q  A  F  F  Q  P  L  E  C  E  P>

688
       ATTCTTCAGA TCGGGTATCA GGGGCAACAA GATGGAATGG GAGCAGGACC AAGTGTGAAT
       I  L  Q  I  G  Y  Q  G  Q  Q  D  G  M  G  A  G  P  S  V  N>

738
       AATTACATGT TGGGTTGGTT ACCTTATGAC ACCAACTCTA TTTGAATCTT TCTCACTTAA
       N  Y  M  L  G  W  L  P  Y  D  T  N  S  I  *  I  F  L  T  *>

788
       TCAATCCCTC TCTTTTTTTT TTTGACATTT TTAAGATGAT GTTTCTA
       S  I  P  L  F  F  F  L  T  F  L  R  *  C  F  X>
```

Fig. 5

Sequence Range: -1699 to 3669

```
                                                                  -1650
         GAATTCCCCG GATCTCCATA TACATATCAT ACATATATAT AGTATACTAT CTTTAGACTG
         CTTAAGGGGC CTAGAGGTAT ATGTATAGTA TGTATATATA TCATATGATA GAAATCTGAC

-1600
         ATTTCTCTAT ACACTATCTT TTAACTTATG TATCGTTTCA AAACTCAGGA CGTACATGTT
         TAAAGAGATA TGTGATAGAA AATTGAATAC ATAGCAAAGT TTTGAGTCCT GCATGTACAA

-1550
         TTAAATTTGG TTATATAACC ACGACCATTT CAAGTATATA TGTCATACCA TACCAGATTT
         AATTTAAACC AATATATTGG TGCTGGTAAA GTTCATATAT ACAGTATGGT ATGGTCTAAA

-1500
         AATATAACTT CTATGAAGAA AATACATAAA GTTGGATTAA AATGCAAGTG ACATCTTTTT
         TTATATTGAA GATACTTCTT TTATGTATTT CAACCTAATT TTACGTTCAC TGTAGAAAAA

-1450                                              -1400
         AGCATAGGTT CATTTGGCAT AGAAGAAATA TATAACTAAA AATGAACTTT AACTTAAATA
         TCGTATCCAA GTAAACCGTA TCTTCTTTAT ATATTGATTT TTACTTGAAA TTGAATTTAT

-1350
         GATTTTACTA TATTACAATT TTTTCTTTTT ACATGGTCTA ATTTATTTTT CTAAAATTAG
         CTAAAATGAT ATAATGTTAA AAAAGAAAAA TGTACCAGAT TAAATAAAAA GATTTTAATC

-1300
         TATGATTGTT GTTTTGATGA AACAATAATA CCGTAAGCAA TAGTTGCTAA AAGATGTCCA
         ATACTAACAA CAAAACTACT TTGTTATTAT GGCATTCGTT ATCAACGATT TTCTACAGGT

-1250
         AATATTTATA AATTACAAAG TAAATCAAAT AAGGAAGAAG ACACGTGGAA AACACCAAAT
         TTATAAATAT TTAATGTTTC ATTTAGTTTA TTCCTTCTTC TGTGCACCTT TTGTGGTTTA

-1200
         AAGAGAAGAA ATGGAAAAAA CAGAAAGAAA TTTTTTAACA AGAAAAATCA ATTAGTCCTC
         TTCTCTTCTT TACCTTTTTT GTCTTTCTTT AAAAAATTGT TCTTTTTAGT TAATCAGGAG

-1150                                         -1100
         AAACCTGAGA TATTTAAAGT AATCAACTAA AACAGGAACA CTTGACTAAC AAAGAAATTT
         TTTGGACTCT ATAAATTTCA TTAGTTGATT TTGTCCTTGT GAACTGATTG TTTCTTTAAA

-1050
         GAAATGTGGT CCAACTTTCA CTTAATTATA TTGTTTTCTC TAAGGCTTAT GCAATATATG
         CTTTACACCA GGTTGAAAGT GAATTAATAT AACAAAGAG ATTCCGAATA CGTTATATAC

-1000
         CCTTAAGCAA ATGCCGAATC TGTTTTTTTT TTTTGTTATT GGATATTGAC TGAAAATAAG
         GGAATTCGTT TACGGCTTAG ACAAAAAAAA AAAACAATAA CCTATAACTG ACTTTTATTC

-950
         GGGTTTTTTC ACACTTGAAG ATCTCAAAAG AGAAAACTAT TACAACGGAA ATTCATTGTA
         CCCAAAAAAG TGTGAACTTC TAGAGTTTTC TCTTTTGATA ATGTTGCCTT TAAGTAACAT

-900
         AAAGAAGTGA TTAAGCAAAT TGAGCAAAGG TTTTTATGTG GTTTATTTCA TTATATGATT
         TTTCTTCACT AATTCGTTTA ACTCGTTTCC AAAAATACAC CAAATAAAGT AATATACTAA

-850                                            -800
         GACATCAAAT TGTATATATA TGGTTGTTTT ATTTAACAAT ATATATGGAT ATAACGTACA
         CTGTAGTTTA ACATATATAT ACCAACAAAA TAAATTGTTA TATATACCTA TATTGCATGT
```

Fig. 6a

```
                                                       -750
AACTAAATAT GTTTGATTGA CGAAAAAAAA TATATGTATG TTTGATTAAC AACATAGCAC
TTGATTTATA CAAACTAACT GCTTTTTTTT ATATACATAC AAACTAATTG TTGTATCGTG

-700
ATATTCAACT GATTTTTGTC CTGATCATCT ACAACTTAAT AAGAACACAC AACATTGAAA
TATAAGTTGA CTAAAAACAG GACTAGTAGA TGTTGAATTA TTCTTGTGTG TTGTAACTTT

-650
AAATCTTTGA CAAAATACTA TTTTTGGGTT TGAAATTTTG AATACTTACA ATTATTCTTC
TTTAGAAACT GTTTTATGAT AAAAACCCAA ACTTTAAAAC TTATGAATGT TAATAAGAAG

-600
TCGATCTTCC TCTCTTTCCT TAAATCCTGC GTACAAATCC GTCGACGCAA TACATTACAC
AGCTAGAAGG AGAGAAAGGA ATTTAGGACG CATGTTTAGG CAGCTGCGTT ATGTAATGTG

-550                                                        -500
AGTTGTCAAT TGGTTCTCAG CTCTACCAAA AACATCTATT GCCAAAAGAA AGGTCTATTT
TCAACAGTTA ACCAAGAGTC GAGATGGTTT TTGTAGATAA CGGTTTTCTT TCCAGATAAA

-450
GTACTTCACT GTTACAGCTG AGAACATTAA ATATAATAAG CAAATTTGAT AAAACAAAGG
CATGAAGTGA CAATGTCGAC TCTTGTAATT TATATTATTC GTTTAAACTA TTTTGTTTCC

-400
GTTCTCACCT TATTCCAAAA GAATAGTGTA AAATAGGGTA ATAGAGAAAT GTTAATAAAA
CAAGAGTGGA ATAAGGTTTT CTTATCACAT TTTATCCCAT TATCTCTTTA CAATTATTTT

-350
GGAAATTAAA AATAGATATT TTGGTTGGTT CAGATTTTGT TTCGTAGATC TACAGGGAAA
CCTTTAATTT TTATCTATAA AACCAACCAA GTCTAAAACA AAGCATCTAG ATGTCCCTTT

-300
TCTCCGCCGT CAATGCAAAG CGAAGGTGAC ACTTGGGGAA GGACCAGTGG TCCGTACAAT
AGAGGCGGCA GTTACGTTTC GCTTCCACTG TGAACCCCTT CCTGGTCACC AGGCATGTTA

-250                                              -200
GTTACTTACC CATTTCTCTT CACGAGACGT CGATAATCAA ATTGTTTATT TTCATATTTT
CAATGAATGG GTAAAGAGAA GTGCTCTGCA GCTATTAGTT TAACAAATAA AAGTATAAAA

-150
TAAGTCCGCA GTTTTATTAA AAAATCATGG ACCCGACATT AGTACGAGAT ATACCAATGA
ATTCAGGCGT CAAAATAATT TTTTAGTACC TGGGCTGTAA TCATGCTCTA TATGGTTACT

-100
GAAGTCGACA CGCAAATCCT AAAGAAACCA CTGTGGTTTT TGCAAACAAG AGAAACCAGC
CTTCAGCTGT GCGTTTAGGA TTTCTTTGGT GACACCAAAA ACGTTTGTTC TCTTTGGTCG

-50
TTTAGCTTTT CCCTAAAACC ACTCTTACCC AAATCTCTCC ATAAATAAAG ATCCCGAGAC
AAATCGAAAA GGGATTTTGG TGAGAATGGG TTTAGAGAGG TATTTATTTC TAGGGCTCTG

1
TCAAACACAA GTCTTTTTAT AAAGGAAAGA AAGAAAAACT TTCCTAATTG GTTCATACCA
AGTTTGTGTT CAGAAAAATA TTTCCTTTCT TTCTTTTTGA AAGGATTAAC CAAGTATGGT 51                                      101
AAGTCTGAGC TCTTCTTTAT ATCTCTCTTG TAGTTTCTTA TTGGGGGTCT TTGTTTTGTT
TTCAGACTCG AGAAGAAATA TAGAGAGAAC ATCAAAGAAT AACCCCCAGA AACAAAACAA

151
TGGTTCTTTT AGAGTAAGAA GTTTCTTAAA AAAGGATCAA AAATGGGAAG GGGTAGGGTT
```

Fig. 6b

```
                ACCAAGAAAA TCTCATTCTT CAAAGAATTT TTTCCTAGTT TTTACCCTTC CCCATCCCAA
                                          201
                CAATTGAAGA GGATAGAGAA CAAGATCAAT AGACAAGTGA CATTCTCGAA AAGAAGAGCT
                GTTAACTTCT CCTATCTCTT GTTCTAGTTA TCTGTTCACT GTAAGAGCTT TTCTTCTCGA
                                          251
                GGTCTTTTGA AGAAAGCTCA TGAGATCTCT GTTCTCTGTG ATGCTGAAGT TGCTCTTGTT
                CCAGAAAACT TCTTTCGAGT ACTCTAGAGA CAAGAGACAC TACGACTTCA ACGAGAACAA
                                          301
                GTCTTCTCCC ATAAGGGGAA ACTCTTCGAA TACTCCACTG ATTCTTGGTA ACTTCAACTA
                CAGAAGAGGG TATTCCCCTT TGAGAAGCTT ATGAGGTGAC TAAGAACCAT TGAAGTTGAT
                           351                                                   401
                ATTCTTTACT TTTAAAAAAA TCTTTTAATC TGCTACTTTA TATAGTTTTT TTCCCCCTTA
                TAAGAAATGA AAATTTTTTT AGAAAATTAG ACGATGAAAT ATATCAAAAA AAGGGGGAAT
                                                              451
                AGTTGACTAC TTGATTTGCC CTAATTATTC ACTACTGCTT TTGTTATATA TTTTCTAGGG
                TCAACTGATG AACTAAACGG GATTAATAAG TGATGACGAA AACAATATAT AAAAGATCCC
                                          501
                CTTCCATTTT TGGATTTTTT GATTAGCCAG AAAAATGTTT AATACAAATT TGTATAATTT
                GAAGGTAAAA ACCTAAAAAA CTAATCGGTC TTTTTACAAA TTATGTTTAA ACATATTAAA
                                          551
                AAAAATCAAA ACTTTAGGGC CGTAGTGAAG TGAACCCTAG AACACACAGA TTATACCATA
                TTTTTAGTTT TGAAATCCCG GCATCACTTC ACTTGGGATC TTGTGTGTCT AATATGGTAT
                           601
                GTAATTACCT TGATATATTG TGCAATATTT ATCAGCATCA TATCTTCAAA CTCAAGAGAT
                CATTAATGGA ACTATATAAC ACGTTATAAA TAGTCGTAGT ATAGAAGTTT GAGTTCTCTA
                           651                                                   701
                ATAGAAGGGT ATGTTAATCT TTGAACTAGG GTTTTGATCC CTAACTCATA ATGAATCCTT
                TATCTTCCCA TACAATTAGA AACTTGATCC CAAAACTAGG GATTGAGTAT TACTTAGGAA
                                                              751
                TTGTTCTCCA ATAGCCATGT CTTTCGAATT TGCAGATCTA AGCTCTAATT GATGCCATAG
                AACAAGAGGT TATCGGTACA GAAAGCTTAA ACGTCTAGAT TCGAGATTAA CTACGGTATC
                                          801
                TAAGAAAATA AGATCTGTAG TTTTCACTCG CTCACTGAGT TCGAGTTTTA AATGAAGTGT
                ATTCTTTTAT TCTAGACATC AAAAGTGAGC GAGTGACTCA AGCTCAAAAT TTACTTCACA
                                          851
                CGTTTCTTTT TTCATATATA GTTGCAACTG GATTATAATT AAAAAATATT ATGGGACGAG
                GCAAAGAAAA AAGTATATAT CAACGTTGAC CTAATATTAA TTTTTTATAA TACCCTGCTC
                                          901
                AAAATAATTT AAAATAGATA TAGATAACAA TGTCAAATTG AGAATTTTTT ATTAGAAAGA
                TTTTATTAAA TTTTATCTAT ATCTATTGTT ACAGTTTAAC TCTTAAAAAA TAATCTTTCT
                           951                                                   1001
                ATATTTAACT TACGAGTTGT TTTTTTTCAG CTGTAAAAGA ATATCTAATT TGTTCTCACG
                TATAAATTGA ATGCTCAACA AAAAAAAGTC GACATTTTCT TATAGATTAA ACAAGAGTGC
                                                              1051
                ACTGTGTCTT CATGTTTTGC AAATCTAAGC AAAGAAAATG TTTAAACTCG GATCTTAAGA
                TGACACAGAA GTACAAAACG TTTAGATTCG TTTCTTTTAC AAATTTGAGC CTAGAATTCT
```

Fig. 6c

```
                                        1101
TTATGAACTC GTAATATAAA ACACTATATA GTATTAAATT TGAACTAGTG TTGCTTCTTT
AATACTTGAG CATTATATTT TGTGATATAT CATAATTTAA ACTTGATCAC AACGAAGAAA

1151
TGCTACTTTG ACTTTAGAAA TTAAAACTGA AACAAAGATG TCAAATCTGA GTAGGGAGTC
ACGATGAAAC TGAAATCTTT AATTTTGACT TTGTTTCTAC AGTTTAGACT CATCCCTCAG

1201
TTTGACCTCT GGGGATCCAT AAAAAGAACT AACTCCATCC TAAAATCGGC TTCTTACCGA
AAACTGGAGA CCCCTAGGTA TTTTTCTTGA TTGAGGTAGG ATTTTAGCCG AAGAATGGCT 1251                                              1301
TGGTCAAACT TAGCTCCAAC AAGCAACAGC TGTTCTTCTT TTTTTTTTTT TTTTTTTTTT
ACCAGTTTGA ATCGAGGTTG TTCGTTGTCG ACAAGAAGAA AAAAAAAAAA AAAAAAAAAA

1351
TTTAAGCATT GTCCTTGTTC TGAAAAAAAA TAAGATTGGT AAATTGGCAA GATTATAATA
AAATTCGTAA CAGGAACAAG ACTTTTTTTT ATTCTAACCA TTTAACCGTT CTAATATTAT

1401
ATTTATTATA ATGTGTCGCA CTAAGAAGAT TTTCTGTACC TAATTGTAGC AAAATTAAAG
TAAATAATAT TACACAGCGT GATTCTTCTA AAAGACATGG ATTAACATCG TTTTAATTTC

1451
AAACCGCAGT TAGAACTCGA AGCTAAGAGC ATAGGGTCTA TGATTCATAC TGTTTTGTTA
TTTGGCGTCA ATCTTGAGCT TCGATTCTCG TATCCCAGAT ACTAAGTATG ACAAAACAAT

1501
TTATAAAGGT ATCATAGAGA TCGGTACTTG ATTTGTTATA GGAAATCTTG GTTTAATTGC
AATATTTCCA TAGTATCTCT AGCCATGAAC TAAACAATAT CCTTTAGAAC CAAATTAACG 1551                                        1601
ATAAAACCAT CATTAGATTT ATCCTAAAAT GTGATGATAT TTTGGTCACA TCTCCATATT
TATTTTGGTA GTAATCTAAA TAGGATTTTA CACTACTATA AAACCAGTGT AGAGGTATAA

1651
ATTTATATAA TAAAATGATA ATTGGTTGAT GATAAAGCTA ACCCTAATTC TGTGAAATGA
TAAATATATT ATTTTACTAT TAACCAACTA CTATTTCGAT TGGGATTAAG ACACTTTACT

1701
TCAGTATGGA GAAGATACTT GAACGCTATG AGAGGTACTC TTACGCCGAA AGACAGCTTA
AGTCATACCT CTTCTATGAA CTTGCGATAC TCTCCATGAG AATGCGGCTT TCTGTCGAAT

1751
TTGCACCTGA GTCCGACGTC AATGTATTTC AATAAATATT TCTCCTTTTA ATCCACATAT
AACGTGGACT CAGGCTGCAG TTACATAAAG TTATTTATAA AGAGGAAAAT TAGGTGTATA

1801
ATATTATATC AATCTATTTG TAGTATTGAT GAATTTTATT TGTATAAAAC TTCTGGTACA
TATAATATAG TTAGATAAAC ATCATAACTA CTTAAAATAA ACATATTTTG AAGACCATGT 1851                                        1901
CAGACAAACT GGTCGATGGA GTATAACAGG CTTAAGGCTA AGATTGAGCT TTTGGAGAGA
GTCTGTTTGA CCAGCTACCT CATATTGTCC GAATTCCGAT TCTAACTCGA AAACCTCTCT

1951
AACCAGAGGT ACACATTTAC ACTCATCACA TTTCTATCTA GAAAATCGAT CGGGTTCCAT
TTGGTCTCCA TGTGTAAATG TGAGTAGTGT AAAGATAGAT CTTTTAGCTA GCCCAAGGTA

2001
TTTAAAGTAA GTTAAAATTC ATTGATGCTA TTGAAATTCA GGCATTATCT TGGGGAAGAC
```

Fig. 6d

```
           AAATTTCATT CAATTTTAAG TAACTACGAT AACTTTAAGT CCGTAATAGA ACCCCTTCTG

2051
           TTGCAAGCAA TGAGCCCTAA AGAGCTTCAG AATCTGGAGC AGCAGCTTGA CACTGCTCTT
           AACGTTCGTT ACTCGGGATT TCTCGAAGTC TTAGACCTCG TCGTCGAACT GTGACGAGAA

2101
           AAGCACATCC GCACTAGAAA AGTATTGCCT TCTGCTATTT CGTTGAACAT ATCTATATAA
           TTCGTGTAGG CGTGATCTTT TCATAACGGA AGACGATAAA GCAACTTGTA TAGATATATT 2151                                          2201
           CTTAAACGTT TACAAGTGTT ATTATAATGT GAACATTGAA ATACATATGT GTATGTATCA
           GAATTTGCAA ATGTTCACAA TAATATTACA CTTGTAACTT TATGTATACA CATACATAGT

2251
           ATATATATAT CAGTAATCAA TATCAATTTG ATATGTCTAT AGGTTGGTTC GAATGTATGA
           TATATATATA GTCATTAGTT ATAGTTAAAC TATACAGATA TCCAACCAAG CTTACATACT

2301
           GTTATGTTGT GTATTTTAAG ACTCCATATT ACTTAAAGTA ATGGGTTGTT AATGTTGATG
           CAATACAACA CATAAAATTC TGAGGTATAA TGAATTTCAT TACCCAACAA TTACAACTAC

2351
           TGTGTGTATG CAGAACCAAC TTATGTACGA GTCCATCAAT GAGCTCCAAA AAAAGGTATG
           ACACACATAC GTCTTGGTTG AATACATGCT CAGGTAGTTA CTCGAGGTTT TTTTCCATAC

2401
           TAAAACCCCT ATCAAATGTA TGTCTTATAG AGAAACGTAT AGGAAAGCTA ATTAACAATC
           ATTTTGGGGA TAGTTTACAT ACAGAATATC TCTTTGCATA TCCTTTCGAT TAATTGTTAG 2451                                          2501
           GTGCCGTTTC GGAAATGACA GGAGAAGGCC ATACAGGAGC AAAACAGCAT GCTTTCTAAA
           CACGGCAAAG CCTTTACTGT CCTCTTCCGG TATGTCCTCG TTTTGTCGTA CGAAAGATTT

2551
           CAGGTAACAC ATGTCATCAT TTCTCTTTCA TCAACATGTT GTCCATTGCA TTACTGTTAC
           GTCCATTGTG TACAGTAGTA AAGAGAAAGT AGTTGTACAA CAGGTAACGT AATGACAATG

2601
           CTTCCACTGT TCTGCTCCAC ACTTCCAGCC AAGCTATACC TACGATATCT TCATATCTCC
           GAAGGTGACA AGACGAGGTG TGAAGGTCGG TTCGATATGG ATGCTATAGA AGTATAGAGG

2651
           ACTTAACTTC GGCACCATTA AATAAAAATA GAAATCTTT GCAAATTTGT TTGAAATAGC
           TGAATTGAAG CCGTGGTAAT TTATTTTTAT CTTTTAGAAA CGTTTAAACA AACTTTATCG

2701
           ATAGATGTTG TCTATTGATT GATATAATCA CCAGCCTGTA CGTAGATATG GTTTGTCCGT
           TATCTACAAC AGATAACTAA CTATATTAGT GGTCGGACAT GCATCTATAC CAAACAGGCA 2751                                          2801
           TTAGTTTTAA GGTGTCTCTC GGATTGAAAA TATTTTGAAA TCTTTTGAAA TGTTTGTCCC
           AATCAAAATT CCACAGAGAG CCTAACTTTT ATAAAACTTT AGAAAACTTT ACAAACAGGG

2851
           ATCATTCTTA CTTAGCTCAT ATCTATGTAT ATGAATATAG ACACTACTCC TAATTATAAA
           TAGTAAGAAT GAATCGAGTA TAGATACATA TACTTATATC TGTGATGAGG ATTAATATTT

2901
           ATGTTATAAT AGTTCATTGC ATGAGTGCAA CTGTGAAAAT AACTATTTGT AACCATTGCA
           TACAATATTA TCAAGTAACG TACTCACGTT GACACTTTTA TTGATAAACA TTGGTAACGT
```

Fig. 6e

```
                          2951
TATATATAGT TTCTTCACTT TGAAAATTGA TGATGATAAT ATGGTTTGAA ATAAATTTGC
ATATATATCA AAGAAGTGAA ACTTTTAACT ACTACTATTA TACCAAACTT TATTTAAACG

3001
TGGCAGATCA AGGAGAGGGA AAAAATTCTT AGGGCTCAAC AGGAGCAGTG GGATCAGCAG
ACCGTCTAGT TCCTCTCCCT TTTTTAAGAA TCCCGAGTTG TCCTCGTCAC CCTAGTCGTC 3051                                                  3101
AACCAAGGCC ACAATATGCC TCCCCCTCTG CCACCGCAGC AGCACCAAAT CCAGCATCCT
TTGGTTCCGG TGTTATACGG AGGGGGAGAC GGTGGCGTCG TCGTGGTTTA GGTCGTAGGA

3151
TACATGCTCT CTCATCAGCC ATCTCCTTTT CTCAACATGG GGTAACAAAA AATTACTAAT
ATGTACGAGA GAGTAGTCGG TAGAGGAAAA GAGTTGTACC CCATTGTTTT TTAATGATTA

3201
CAGTCTTAAT TTAAAGCACA TATGTTATGC AAGCTAGTTA CGTTAGGTGT TGTAATTTCA
GTCAGAATTA AATTTCGTGT ATACAATACG TTCGATCAAT GCAATCCACA ACATTAAAGT

3251
TTGAAGTTAT AGCTGTTAGT GATGGTTACA TGATGCTAGA TTTTGAAACT AGAAAACTTT
AACTTCAATA TCGACAATCA CTACCAATGT ACTACGATCT AAAACTTTGA TCTTTTGAAA

3301
ATTTTAAAAC ATTATTTTAT TAACGTAGGT TAATGCAATG GTCGCCAAAC GAACAAACTT
TAAAATTTTG TAATAAAATA ATTGCATCCA ATTACGTTAC CAGCGGTTTG CTTGTTTGAA 3351                                      3401
ATTAGTGTGG AAAAATGTAC ATGGAATGGT TGCGAAAAGC CTAAGTCGAC TTTTGTTGTT
TAATCACACC TTTTTACATG TACCTTACCA ACGCTTTTCG GATTCAGCTG AAAACAACAA

3451
GTTGGTCTAT GTGTTTAAGT ACAATTTTAG TTTGTTAGAT AAATGAAATT AATATATCTT
CAACCAGATA CACAAATTCA TGTTAAAATC AAACAATCTA TTTACTTTAA TTATATAGAA

3501
TGACATTTCA CAATGGACTG ATATTTGATT TTCCTTTGTT GTACGGTGAA ACATATGATT
ACTGTAAAGT GTTACCTGAC TATAAACTAA AAGGAAACAA CATGCCACTT TGTATACTAA

3551
ACATATGCAC TTTCATATAT ATCCTATGTA TGATTGTGAA TGCAGTGGTC TGTATCAAGA
TGTATACGTG AAAGTATATA TAGGATACAT ACTAACACTT ACGTCACCAG ACATAGTTCT

3601
AGATGATCCA ATGGCAATGA GGAGGAATGA TCTCGAACTG ACTCTTGAAC CCGTTTACAA
TCTACTAGGT TACCGTTACT CCTCCTTACT AGAGCTTGAC TGAGAACTTG GGCAAATGTT

3651
CTGCAACCTT GGCTGCTTCG CCGCATGA
GACGTTGGAA CCGACGAAGC GGCGTACT
```

Fig. 6f

```
Sequence Range: -140 to 1080
                                                                       -91
           GAATTCGGCA CGAGAACTTT CCTAATTGGT TCATACCAAA GTCTGAGCTC TTCTTTATAT

-41
           CTCTCTTGTA GTTTCTTATT GGGGGTCTTT GTTTTGTTTG GTTCTTTTAG AGTAAGAAGT

10
           TTCTTAAAAA AGGATCAAAA ATGGGAAGGG GTAGGGTTCA ATTGAAGAGG ATAGAGAACA
                                     M  G  R   G  R  V  Q   L  K  R   I  E  N>

60
           AGATCAATAG ACAAGTGACA TTCTCGAAAA GAAGAGCTGG TCTTTTGAAG AAAGCTCATG
            K  I  N  R   Q  V  T   F  S  K   R  R  A  G   L  L  K   K  A  H>

110                                                    160
           AGATCTCTGT TCTCTGTGAT GCTGAAGTTG CTCTTGTTGT CTTCTCCCAT AAGGGGAAAC
            E  I  S  V   L  C  D   A  E  V   A  L  V  V   F  S  H   K  G  K>

210
           TCTTCGAATA CTCCACTGAT TCTTGTATGG AGAAGATACT TGAACGCTAT GAGAGGTACT
            L  F  E  Y   S  T  D   S  C  M   E  K  I  L   E  R  Y   E  R  Y>

260
           CTTACGCCGA AAGACAGCTT ATTGCACCTG AGTCCGACGT CAATACAAAC TGGTCGATGG
            S  Y  A  E   R  Q  L   I  A  P   E  S  D  V   N  T  N   W  S  M>

310
           AGTATAACAG GCTTAAGGCT AAGATTGAGC TTTTGGAGAG AAACCAGAGG CATTATCTTG
            E  Y  N  R   L  K  A   K  I  E   L  L  E  R   N  Q  R   H  Y  L>

360
           GGGAAGACTT GCAAGCAATG AGCCCTAAAG AGCTTCAGAA TCTGGAGCAG CAGCTTGACA
            G  E  D  L   Q  A  M   S  P  K   E  L  Q  N   L  E  Q   Q  L  D>

410                                                    460
           CTGCTCTTAA GCACATCCGC ACTAGAAAAA ACCAACTTAT GTACGAGTCC ATCAATGAGC
            T  A  L  K   H  I  R   T  R  K   N  Q  L  M   Y  E  S   I  N  E>

510
           TCCAAAAAAA GGAGAAGGCC ATACAGGAGC AAAACAGCAT GCTTTCTAAA CAGATCAAGG
            L  Q  K  K   E  K  A   I  Q  E   Q  N  S  M   L  S  K   Q  I  K>

560
           AGAGGGAAAA AATTCTTAGG GCTCAACAGG AGCAGTGGGA TCAGCAGAAC CAAGGCCACA
            E  R  E  K   I  L  R   A  Q  Q   E  Q  W  D   Q  Q  N   Q  G  H>

610
           ATATGCCTCC CCCTCTGCCA CCGCAGCAGC ACCAAATCCA GCATCCTTAC ATGCTCTCTC
            N  M  P  P   P  L  P   P  Q  Q   H  Q  I  Q   H  P  Y   M  L  S>

660
           ATCAGCCATC TCCTTTTCTC AACATGGGTG GTCTGTATCA AGAAGATGAT CCAATGGCAA
            H  Q  P  S   P  F  L   N  M  G   G  L  Y  Q   E  D  D   P  M  A>

710                                                    760
           TGAGGAGGAA TGATCTCGAA CTGACTCTTG AACCCGTTTA CAACTGCAAC CTTGGCTGCT
            M  R  R  N   D  L  E   L  T  L   E  P  V  Y   N  C  N   L  G  C>

810
           TCGCCGCATG AAGCATTTCC ATATATATAT ATTTGTAATC GTCAACAATA AAAACAGTTT
            F  A  A  *
                                                   860
           GCCACATACA TATAAATAGT GGCTAGGCTC TTTTCATCCA ATTAATATAT TTTGGCAAAT
                                         910
           GTTCGATGTT CTTATATCAT CATATATAAA TTAGCAGGCT CCTTTCTTCT TTTGTAATTT
```

Fig. 8a

```
                     960
GATAAGTTTA TTTGCTTCAA TATGGAGCAA AATTGTAATA TATTTGAAGG TCAGAGAGAA
    1010                                                     1060
TGAACGTGAA CTTAATAGAA AAAAAAAAAA AAAAAAAAAA AAAAAAAAAA AAAAAAAACC
CGACGTAGCT CGAGGAATTC
```

Fig. 8b

```
Sequence Range: -346 to 1028
                                                    -297
         GAATTCCGGA TTCACAAAAA CTTTTCTTCA GATTCACAAT CTCATCACAA CCCTTCAAAA

-247
         AGAGAAAAGA TCTAAAGAAT AAACAAGAGC CCTAATATCA AATCACAACC AAAAAAACCA

-197
         AAGAAAGCTA ATTAAAGTTT TCTCTCTAGC TATTCCTCTT CTTTTCTTGT TCTTGAAAAC

-147
         TAGGGTTTAC TTCACCAAAA GATAAGATCT TTCCCCAGAA AAAGCAATAC CCAAGTCATG

-97                                                          -47
         TTTCTGTGTG TCTGTATATA GATAAAACAT TACATACCCT AATAAGGTTA CACAAATAGC

4
         TATAAAAGAG GGAAAATAAG ATAGGGATTT TTTGGGGTGA GGAAAGATGG GAAGAGGAAG
                                                             M   G  R  G  R>

54
         AGTAGAGCTC AAGAGGATAG AGAACAAAAT CAACAGACAA GTGACGTTTG CTAAACGTAG
          V  E  L   K  R  I    E  N  K  I   N  R  Q    V  T  F    A  K  R  R>

104
         AAATGGTTTG CTGAAAAAAG CTTATGAGCT TTCTGTTCTC TGCGATGCTG AAGTCTCTCT
          N  G  L    L  K  K    A  Y  E  L   S  V  L    C  D  A    E  V  S  L>

154
         CATCGTCTTC TCCAACCGTG GCAAGCTCTA CGAGTTCTGC AGCACCTCCA ACATGCTCAA
          I  V  F     S  N  R   G  K  L  Y   E  F  C    S  T  S    N  M  L  K>

204                                              254
         GACACTGGAA AGGTATCAGA AGTGTAGCTA TGGCTCCATT GAAGTCAACA ACAAACCTGC
          T  L  E    R  Y  Q    K  C  S  Y   G  S  I    E  V  N    N  K  P  A>

304
         TAAAGAGCTT GAGAACAGCT ACAGAGAGTA CTTGAAGCTG AAAGGTAGAT ATGAAAATCT
          K  E  L    E  N  S    Y  R  E  Y   L  K  L    K  G  R    Y  E  N  L>

354
         GCAACGTCAG CAGAGAAATC TTCTTGGAGA GGATCTTGGA CCTCTGAATT CAAAGGAGCT
          Q  R  Q    Q  R  N    L  L  G  E   D  L  G    P  L  N    S  K  E  L>

404
         AGAGCAGCTT GAGCGTCAAC TAGACGGCTC TCTGAAGCAA GTTCGCTGCA TCAAGACACA
          E  Q  L    E  R  Q    L  D  G  S   L  K  Q    V  R  C    I  K  T  Q>

454
         GTATATGCTT GACCAGCTCT CTGATCTTCA AGGTAAGGAG CATATCTTGC TTGATGCCAA
          Y  M  L    D  Q  L    S  D  L  Q   G  K  E    H  I  L    L  D  A  N>

504                                             554
         CAGAGCTTTG TCAATGAAGC TGGAAGATAT GATCGGCGTG AGACATCACC ATATAGGAGG
          R  A  L    S  M  K    L  E  D  M   I  G  V    R  H  H    H  I  G  G>

604
         AGGATGGGAA GGTGGTGATC AACAGAATAT TGCCTATGGA CATCCTCAGG CTCATTCTCA
          G  W  E    G  G  D    Q  Q  N  I   A  Y  G    H  P  Q    A  H  S  Q>

654
         GGGACTATAC CAATCTCTTG AATGTGATCC CACTTTGCAA ATTGGATATA GCCATCCAGT
          G  L  Y    Q  S  L    E  C  D  P   T  L  Q    I  G  Y    S  H  P  V>

704
         GTGCTCAGAG CAAATGGCTG TGACGGTGCA AGGTCAGTCC CAACAAGGAA ACGGCTACAT
          C  S  E    Q  M  A    V  T  V  Q   G  Q  S    Q  Q  G    N  G  Y  I>
```

Fig. 10a

```
                754
CCCTGGCTGG ATGCTGTGAG CGATACTTCT TCCCCCAATA AAGATCTTAA GCAAGTACTG
  P   G   W    M   L   *
    804                                                         854
GTGGGGTCTT CGTGGTGTGA TCTTAGATCT TATGCATATG AATAATAATG TTATTGCACA

904
AGACTTTTGC TTTTGTAGAC ACAAGTGGCT ATAGCTGTAA TAGCCTTCAA CATCTCTCTT

954
CTGTTTCAGG ATTTGTTTGT GCCTATTGTA ATTGCTTATA TATGTATGGT TTGTATAATG

1004
TGTGAAATGT TAACATCGAC CATGTCTCAT CTGGTGAAAA AAAAAAAAAA AAAA
```

Fig. 10b

Sequence Range: -395 to 908

```
                                                              -346
          GAATTCCGGC CCTCACACAT TTCTTATCTT TTGCTCTCAA TAGATTCCAT TGATTCAAAA

-296
          CAAAATTTTC ATTAAGATTT CACAACCTCC ACACACTTCC AAACACAATT AAAGAGAGGA

-246
          AAAAGAATCA ATAACCCTAT AAATAAAAAA TCAGACAAAC AGAAGTTTCC TCTTCTTCTT

-196
          CCTTAAGCTA GTACCTTTTG TTCTTGAAAT TAGGGTTAAT TTCTTTTTTC CAAATACCAT

-146                                                    -96
          CAATTCTCCA GACCATAAAA ACTCAAAAAG ATCAGATCTT CCTCTGAAA AAGAGATACC

-46
          CAACTTATGT TTTTGTGTGT CTGTATATAG ATAAACATTA CATACCCATA TTTGTGTATA

5
          GACATAAAAA GTGGAAATTA AGGTAACAAA AAGAAATGGG AAGAGGAAGA GTAGAGCTGA
                                                 M   G    R  G   R   V   E   L>

55
          AGAGGATAGA GAACAAAATC AACAGACAAG TAACGTTTGC AAAGCGTAGG AACGGTTTGT
           K  R  I  E   N  K  I   N  R  Q    V  T  F  A   K  R  R   N  G  L>

105
          TGAAGAAAGC TTATGAATTG TCTGTTCTCT GTGATGCTGA AGTTGCTCTC ATCATCTTCT
           L  K  K  A   Y  E  L   S  V  L    C  D  A  E   V  A  L   I  I  F>

155                                                205
          CCAACCGTGG AAAGCTCTAT GAGTTTTGCA GCTCCTCAAA CATGCTCAAG ACACTTGATC
           S  N  R  G   K  L  Y   E  F  C    S  S  S  N   M  L  K   T  L  D>

255
          GGTACCAGAA ATGCAGCTAT GGATCCATTG AAGTCAACAA CAAACCTGCC AAAGAACTTG
           R  Y  Q  K   C  S  Y   G  S  I    E  V  N  N   K  P  A   K  E  L>

305
          AGAACAGCTA CAGAGAATAT CTGAAGCTTA AGGGTAGATA TGAGAACCTT CAACGTCAAC
           E  N  S  Y   R  E  Y   L  K  L    K  G  R  Y   E  N  L   Q  R  Q>

355
          AGAGAAATCT TCTTGGGGAG GATTTAGGAC CTTTGAATTC AAAGGAGTTA GAGCAGCTTG
           Q  R  N  L   L  G  E   D  L  G    P  L  N  S   K  E  L   E  Q  L>

405
          AGCGTCAACT GGACGGCTCT CTCAAGCAAG TTCGGTCCAT CAAGACACAG TACATGCTTG
           E  R  Q  L   D  G  S   L  K  Q    V  R  S  I   K  T  Q   Y  M  L>

455                                      505
          ACCAGCTCTC GGATCTTCAA AATAAAGAGC AAATGTTGCT TGAAACCAAT AGAGCTTTGG
           D  Q  L  S   D  L  Q   N  K  E    Q  M  L  L   E  T  N   R  A  L>

555
          CAATGAAGCT GGATGATATG ATTGGTGTGA GAAGTCATCA TATGGGAGGA TGGGAAGGCG
           A  M  K  L   D  D  M   I  G  V    R  S  H  H   M  G  G   W  E  G>

605
          GTGAACAGAA TGTTACCTAC GCGCATCATC AAGCTCAGTC TCAGGGACTA TACCAGCCTC
           G  E  Q  N   V  T  Y   A  H  H    Q  A  Q  S   Q  G  L   Y  Q  P>

655
          TTGAATGCAA TCCAACTCTG CAAATGGGGT ATGATAATCC AGTATGCTCT GAGCAAATCA
           L  E  C  N   P  T  L   Q  M  G    Y  D  N  P   V  C  S   E  Q  I>
```

Fig. 11a

```
                      705
CTGCGACAAC ACAAGCTCAG GCGCAGCCGG GAAACGGTTA CATTCCAGGA TGGATGCTCT
 T  A  T  T   Q  A  Q   A  Q  P   G  N  G  Y   I  P  G   W  M  L>

755                                                    805
GAGAATCATG TACTGTGATG AAGCTCACCC ACAAAAGACC TTATATATAT ATAAAGTATA
 *

GATACAAGAC TTGGATTTGT AGACATAAGT GGCTAATATA ATGGTCCTGA GGATCTTCTA

905
GACATTTGTA TCTTTTGGGA ATCCTTGCTT ATATTAAGAA TTC
```

Fig. 11b

METHODS OF SUPPRESSING FLOWERING IN TRANSGENIC PLANTS

CROSS REFERENCE TO RELATED PATENT APPLICATIONS

The present application is a divisional of U.S. patent application Ser. No. 09/869,582, filed Feb. 28, 2002, now U.S. Pat. No. 6,987,214, issued Jan. 17, 2006, which claims priority to PCT/US99/24407, which claims priority to U.S. Provisional Patent Application No. 60/104,604, filed Oct. 16, 1998.

This invention was made with Government support under IBN9418436 awarded by the National Science Foundation. The U.S. Government has certain rights in the invention.

FIELD OF THE INVENTION

The present invention relates generally to plant molecular biology and genetic engineering and more specifically to the production of genetically modified plants in which the natural process of flowering is suppressed.

BACKGROUND INFORMATION

The ecological and economic importance of wood is difficult to overstate, with the total amount of wood in the world's forests estimated at about 1.5 Gt. Thus, wood is by far the most abundant component of the terrestrial biomass. The carbon stored in wood and humus (partially degraded wood) is important in the planetary carbon cycle, which has a significant influence on global climate. In addition, wood is a leading industrial component of the global economy. About 4% of the US gross national product has been attributed to the wood products industry in past decades.

Unfortunately, a growing population is reducing the arable land area in the United States and around the world, while the demand for wood products increases. This growing demand and limited resources have resulted in a need for greater productivity of the remaining forest lands.

The flowering process consumes 25 to 35% of the energy of a typical plant, thereby limiting wood production. Thus, for trees used for lumber or pulp production, for example, it can be advantageous to suppress flowering in order increase the yield of wood. Suppression of flowering also can be desired to eliminate the production of allergic pollen, or to prevent pollen dissemination. Unfortunately, methods of producing genetically modified plants in which flowering is suppressed without effecting other desirable traits are not currently available.

Thus, a need exists for developing genetically modified plant varieties in which the natural process of flowering is suppressed. The present invention satisfies this need and provides related advantages as well.

SUMMARY OF THE INVENTION

The present invention provides a transgenic plant characterized by suppressed flowering. The transgenic plant contains a nucleic acid molecule including a floral organ selective regulatory element operatively linked to a nucleotide sequence encoding a cytotoxic gene product, wherein the nucleic acid molecule is heritable by progeny thereof.

The transgenic plant contains a nucleic acid molecule including a floral organ selective regulatory element operatively linked to a nucleotide sequence encoding a cytotoxic gene product, where the floral organ selective regulatory element is an AGL2 regulatory element, an AGL4 regulatory element or an AGL9 regulatory element, or a AP1 regulatory element, and wherein the nucleic acid molecule is heritable by progeny thereof.

In a transgenic plant of the invention, the floral organ selective regulatory element can be, for example, an AGL2 regulatory element having substantially the nucleotide sequence of *Arabidopsis* AGL2 promoter SEQ ID NO:1, or an active fragment thereof. A floral organ selective regulatory element useful in a transgenic plant of the invention also can be, for example, an AGL4 regulatory element such as an AGL4 regulatory element having substantially the nucleotide sequence of *Arabidopsis* AGL4 promoter SEQ ID NO:2, or an active fragment thereof. A floral organ selective regulatory element also can be an AGL9 regulatory element such as an AGL9 regulatory element having substantially the nucleotide sequence of *Arabidopsis* AGL9 promoter SEQ ID NO:3, or an active fragment thereof. A floral organ selective regulatory element also can be an AP1 regulatory element such as an AP1 regulatory element having substantially the nucleotide sequence of *Arabidopsis* AP1 promoter SEQ ID NO:10, or an active fragment thereof.

DNA sequences encoding a variety of encoded cytotoxic gene products can be used to produce a transgenic plant of the invention, including DNA encoding toxic peptides such as the diphtheria toxin A chain, RNase T1, Barnase RNase, ricin toxin A chain or the herpes simplex virus thymidine kinase (tk) gene product.

The invention further relates to regenerated fertile seedlings and mature plants obtained from transgenic seed or from the vegetative reproduction of transgenic plants, and R1 and subsequent generations, produced by sexual propagation or vegetative reproduction.

The description of the invention hereafter refers to *Arabidopsis thaliana*, when necessary for the sake of example. However, it should be noted that the invention is not limited to genetic transformation of plants such as *Arabidopsis*. The method of the present invention is capable of being practiced for other plant species, including for example, other angiosperm, and other gymnosperm forest plant species, legumes, grasses, other forage crops and the like. Particularly useful transgenic plants can be perennial woody plants such as *Eucalyptus*, cottonwood, birch, alder, Douglas fir, hemlock, pine and spruce.

The present invention also provides a tissue derived from a transgenic plant characterized by suppressed flowering and containing a nucleic acid molecule including a floral organ selective regulatory element operatively linked to a nucleotide sequence encoding a cytotoxic gene product, wherein the nucleic acid molecule is heritable by progeny thereof.

The present invention further provides tissue derived from a transgenic plant characterized by suppressed flowering and containing a nucleic acid molecule including a floral organ selective regulatory element operatively linked to a nucleotide sequence encoding a cytotoxic gene product, where the floral organ selective regulatory element is an AGL2 regulatory element, an AGL4 regulatory element or an AGL9 regulatory element, or an AP1 regulatory element, wherein the nucleic acid molecule is heritable by progeny thereof. A tissue derived from a transgenic plant of the invention can be, for example, a tissue that is capable of vegetative or non-vegetative propagation, or plant cells, plant parts and seed.

The invention additionally is directed to all products derived from transgenic plants, plant cells, plant parts and seeds, which contain a nucleic acid molecule including a floral organ selective regulatory element operatively linked to a nucleotide sequence encoding a cytotoxic gene product, wherein the nucleic acid molecule is heritable by progeny thereof.

The invention also is directed to all products derived from transgenic plants, plant cells, plant parts and seeds, which contain a nucleic a nucleic acid molecule including a floral organ selective regulatory element operatively linked to a nucleotide sequence encoding a cytotoxic gene product, where the floral organ selective regulatory element is an AGL2 regulatory element, an AGL4 regulatory element or an AGL9 regulatory element, or an AP1 regulatory element, wherein the nucleic acid molecule is heritable by progeny thereof.

Also provided by the present invention is a method of producing a fertile, transgenic plant characterized by suppressed flowering. The method is based upon transformation of plant material, selection, plant regeneration, and conventional or propagation breeding techniques.

The method includes the step of introducing into a plant an exogenous nucleic acid molecule containing a floral organ selective regulatory element operatively linked to a nucleotide sequence encoding a cytotoxic gene product (a peptide), wherein the nucleic acid molecule is heritable by asexual or sexually obtained progeny thereof. The method includes the step of introducing into a plant an exogenous nucleic acid molecule containing a floral organ selective regulatory element operatively linked to a nucleotide sequence encoding a cytotoxic gene product, where flowering is suppressed due to selective expression of the exogenous nucleic acid molecule and where the floral organ selective regulatory element is preferably an AGL2 regulatory element, an AGL4 regulatory element or an AGL9 regulatory element, or the AP1 regulatory element.

The present invention also provides an isolated nucleic acid molecule including an AGL2, AGL4 or AGL9 or AP1 regulatory element, which confers selective expression upon an operatively linked nucleotide sequence (structural gene) in one or more floral organs of a plant.

The isolated nucleic acid molecule can further include, if desired, an operatively linked nucleotide sequence encoding a cytotoxic gene product. The encoded cytotoxic gene product can be one of a variety of cytotoxic gene products such as the peptides diphtheria toxin A chain, RNase T1, Barnase RNase, ricin toxin A chain or herpes simplex virus thymidine kinase gene product.

The present invention also provides a kit for producing a transgenic plant characterized by suppressed flowering. A kit of the invention comprises packaging containing a plant expression vector comprising a floral organ selective regulatory element operatively linked to a nucleotide sequence encoding a cytotoxic gene product, and instructions for transforming a susceptible plant with said vector.

BRIEF DESCRIPTION OF THE DRAWINGS

FIG. 1a through 1e shows the *Arabidopsis* AGL2 promoter SEQ ID NO:1.

FIG. 2a through 2f shows the *Arabidopsis* AGL4 promoter SEQ ID NO:2.

FIG. 3a through 3q shows the *Arabidopsis* AGL9 promoter SEQ ID NO:3.

FIG. 4 shows the nucleotide (SEQ ID NO:4) and amino acid sequence (SEQ ID NO:5) of the AGL2 cDNA and the nucleotide (SEQ ID NO:6) and amino acid sequence (SEQ ID NO:7) of the AGL4 cDNA. The AGL2 sequences are shown above the AGL4 sequences.

FIG. 5 shows the nucleotide (SEQ ID NO:8) and deduced amino acid sequence (SEQ ID NOS:9-11) of the AGL9 cDNA.

FIG. 6a through 6f shows the *Arabidopsis* AP1 promoter SEQ ID NO:12.

FIG. 8a through 8b shows the nucleotide (SEQ ID NO:13) and deduced amino acid sequence (SEQ ID NO:14) of the AP1 cDNA.

FIG. 10a through 10b shows the nucleotide (SEQ ID NO:15) and amino acid sequence (SEQ ID NO:7) of the AGL4 cDNA.

FIG. 11a through 11b shows the nucleotide (SEQ ID NO:16) and amino acid sequence (SEQ ID NO:5) of the AGL2 cDNA.

DETAILED DESCRIPTION OF THE INVENTION

Figure 9:
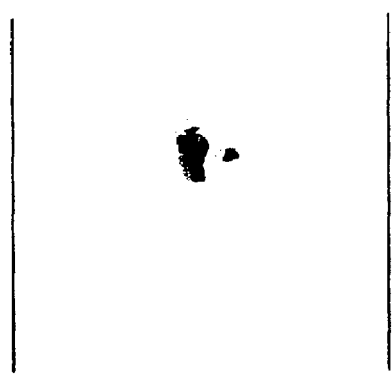
FIG. 9 shows GUS expression in 2 representative AP1 reporter lines. GUS activity is flower specific and GUS staining pattern largely mimics AP1 RNA accumulation pattern.

Flowering is often desirable and is the natural mechanism by which flowering plants propagate. Yet for some applications, it can be desirable to suppress flower and seed production. For example, in trees grown for lumber or pulp, wood yield can be increased by suppressing flower and seed production, which normally consumes 25 to 35% of the energy of a typical plant. Where allergic pollens are a concern, non-flowering varieties are desirable to avoid pollen dissemination. Furthermore, flowering can hasten senescence; thus, non-flowering transgenic plants can have improved longevity.

The present invention provides transgenic plants characterized by suppressed flowering. In a transgenic plant of the invention, a regulatory element that directs selective expression in one or more floral organs is used to control expression of an inhibitory or cytotoxic peptide such as diphtheria toxin or ricin. The selectively expressed cytotoxic gene product destroys floral tissue, thereby suppressing flowering, but is not expressed significantly in vegetative or other tissues and so has no deleterious effect outside the floral tissue.

A fertile transgenic plant of the invention contains a nucleic acid molecule including a floral organ selective regulatory element operatively linked to a nucleotide sequence encoding a cytotoxic gene product, wherein the nucleic acid molecule is heritable by progeny thereof. A fertile transgenic plant of the invention contains a nucleic acid molecule including a floral organ selective regulatory element operatively linked to a nucleotide sequence encoding a cytotoxic gene product, the floral organ selective regulatory element is an AGL2 regulatory element, an AGL4 regulatory element or an AGL9 regulatory element or an AP1 regulatory element, wherein the nucleic acid molecule is heritable by progeny thereof.

"Transgenic" is used herein to include any cell, cell line, callus, tissue, plant part or plant, the genotype of which has been altered beneficially by the presence of heterologous DNA that was introduced into the genotype by a process of genetic engineering, or which was initially introduced into the genotype of a parent plant by such a process and is subsequently transferred to later generations by sexual or asexual cell crosses or cell divisions. As used herein, "genotype" refers to the sum total of genetic material within a cell, either chromosomally, or extrachromosomally borne. Therefore, the term "transgenic" as used herein does not encompass the alteration of the genotype of any plant by conventional plant breeding methods or by naturally occurring events such as random cross-fertilization or spontaneous mutation.

The term "transgenic" may be used herein to describe a plant that contains an exogenous nucleic acid molecule or chimeric nucleic acid construct, which can be derived from an orthologous or heterologous plant or can originate from an animal or virus.

The term "exogenous," as used herein in reference to a nucleic acid molecule and a transgenic plant, means a nucleic acid molecule that is not native to the plant or that is present in the genome in other than its native association. An exogenous nucleic acid molecule can have a naturally occurring or non-naturally occurring nucleotide sequence and can be orthologous or heterologous to the plant species into which it is introduced.

The term "heritable" refers to the fact that the nucleic acid molecule is capable of transmission through a complete sexual cycle of a plant, i.e., it is passed from one plant through its gametes to progeny plants in the same manner as occurs in normal plants, or the nucleic acid can be transmitted via asexual propagation of cuttings or shoots.

The term "operatively linked," as used in reference to a regulatory element and a nucleotide sequence encoding a cytotoxic gene product, means that the regulatory element is linked so that it confers regulated expression upon the operatively linked nucleotide sequence. Thus, the term "operatively linked," as used in reference to a floral organ selective regulatory element and a nucleotide sequence encoding a cytotoxic gene product, means that the floral organ selective regulatory element is linked to the nucleotide sequence encoding the cytotoxic gene product so that the expression pattern of the floral organ selective regulatory element is conferred upon the nucleotide sequence encoding the cytotoxic gene product. It is recognized that a regulatory element and a nucleotide sequence that are operatively linked have, at a minimum, all elements essential for transcription, including, for example, a TATA box.

The term "suppressed," as used herein in reference to the flowering of a transgenic plant of the invention, means a significantly diminished extent of flowering as compared to the extent of flowering in a corresponding plant lacking a nucleic acid molecule containing a floral organ selective regulatory element operatively linked to a nucleotide sequence encoding a cytotoxic gene product. Thus, the term "suppressed" is used broadly to encompass both flowering that is significantly reduced as compared to the flowering in a corresponding non-transgenic plant, and to flowering that is completely precluded. In view of the above, one skilled in the art recognizes that a transgenic plant of the invention can be completely sterile or can be characterized by reduced fertility although generally flowering is suppressed to the extent that the transgenic plant is completely sterile.

Two amino acid sequences are homologous if there is a partial or complete identity between their sequences. For example, 85% homology means that 85% of the amino acids are identical when the two sequences are aligned for maximum matching. Gaps (in either of the two sequences being matched) are allowed in maximizing matching; gap lengths of 5 or less are preferred with 2 or less being more preferred. Alternatively and preferably, two protein sequences (or polypeptide sequences derived from them of at least 30 amino acids in length) are homologous, as this term is used herein, if they have an alignment score of at more than 5 (in standard deviation units) using the program ALIGN with the mutation data matrix and a gap penalty of 6 or greater. See Dayhoff, M. O., in Atlas of Protein Sequence and Structure, 1972, volume 5, National Biomedical Research Foundation, pp. 101-110, and Supplement 2 to this volume, pp. 1-10. The two sequences or parts thereof are more preferably homologous if their amino acids are greater than or equal to 50% identical when optimally aligned using the ALIGN program.

As used herein, the term "sequence identity" means that two polynucleotide sequences are identical (i.e., on a nucleotide-by-nucleotide basis) over the window of comparison. The term "percentage of sequence identity" means that two polynucleotide sequences are identical (i.e., on a nucleotide-by-nucleotide basis) over the window of comparison. The term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity. The terms "substantial identity" as used herein denote a characteristic of a polynucleotide sequence, wherein the polynucleotide comprises a sequence that has at least 85 percent sequence identity, preferably at least 90 to 95 percent sequence identity, more usually at least 99 percent sequence identity as compared to a reference sequence over a comparison window of at least 20 nucleotide positions, frequently over a window of at least 20-50 nucleotides, wherein the percentage of sequence identity is calculated by comparing the reference sequence to the polynucleotide sequence which may include deletions or additions which total 20 percent or less of the reference sequence over the window of comparison. The reference sequence may be a subset of a larger sequence, for example, as a segment of human MCP-1.

As used herein, the term "flowering" is used broadly to refer not only to the traditional flowering of angiosperms but also to the normal reproductive development of other plants such as conifers.

It is recognized that there can be natural variation in the extent of flowering within a plant species or variety. However, a "suppression" in flowering in a transgenic plant of the invention readily can be identified by sampling a population of the corresponding plants, such as wild type plants, and determining that the normal distribution of flowering is significant diminished, on average, as compared to the normal distribution of flowering in a population of the corresponding plant species or variety that does not have a nucleic acid molecule containing a floral organ selective regulatory element operatively linked to a nucleotide sequence encoding a cytotoxic gene product. Thus, production of transgenic plants of the invention provides a means to skew the extent of normal flowering, such that flowering is diminished, on average, at least about 1%, 2%, 5%, 10%, 30%, 50% or 100% as compared to flowering in the corresponding plant species that does not have a nucleic acid molecule containing a floral organ selective regulatory element operatively linked to a nucleotide sequence encoding a cytotoxic gene product.

As used herein, the term "cytotoxic gene product" means a gene product, usually a peptide, that inhibits the growth of, or causes the death of, the cell in which it is expressed. Preferably, a cytotoxic gene product does not result in the death of cells other than the cell in which it is expressed. Thus, expression of a cytotoxic gene product from a floral organ selective regulatory element can be used to ablate cells within one or more floral organs without disturbing neighboring cells. A variety of cytotoxic gene products useful in plants are known in the art including toxins and enzymes, for example, diphtheria toxin A chain polypeptides; RNase T1; Barnase RNase; ricin toxin A chain polypeptides; and herpes simplex virus thymidine kinase (tk) gene products. While the diphtheria toxin A chain, RNase T1 and Barnase RNase are preferred cytotoxic gene products, or multiple nucleotide sequences encoding other cytotoxic gene products, can be used with a floral organ selective regulatory element to generate a transgenic plant of the invention characterized by suppressed flowering.

Diphtheria toxin is the naturally occurring toxin of *Cornebacterium diphtheriae*, which catalyzes the ADP-ribosylation of elongation factor 2, resulting in inhibition of protein synthesis and consequent cell death (Collier, *Bacteriol. Rev.* 39:54-85 (1975)). A single molecule of the fully active toxin is sufficient to kill a cell (Yamaizumi et al., *Cell* 15:245-250 (1978)). Diphtheria toxin has two subunits: the diphtheria toxin B chain directs internalization to most eukaryotic cells through a specific membrane receptor, whereas the A chain encodes the toxic catalytic domain. The catalytic DT-A chain does not include a signal peptide and is not secreted. Further, any DT-A released from dead cells in the absence of the diphtheria toxin B chain is precluded from cell attachment. Thus, DT-A is cell autonomous and directs killing only of the cells in which it is expressed without apparent damage to neighboring cells. The DT-A expression cassette of Palmiter et al., which contains the 193 residues of the A chain engineered with a synthetic ATG and lacking the native leader sequence, is particularly useful in the transgenic plants of the invention (Palmiter et al., *Cell* 50:435-443 (1987); Greenfield et al., *Proc. Natl. Acad. Sci., USA* 80:6853-6857 (1983), each of which is incorporated herein by reference).

RNase T1 of *Aspergillus oryzae* and Barnase RNase of *Bacillus amylolique-faciens* also are cytotoxic gene products useful in the transgenic plants of the invention (Thorsness and Nasrallah, *Methods in Cell Biology* 50:439-448 (1995)). Barnase RNase may be more generally toxic to plants than RNase T1 and, thus, is preferred in the methods of the invention.

Ricin, a ribosome-inactivating protein produced by castor bean seeds, also is a cytotoxic gene product useful in a transgenic plant of the invention. The ricin toxin A chain polypeptide can be used to direct cell-specific ablation as described, for example, in Moffat et al., *Development* 114:681-687 (1992). Plant ribosomes are variably susceptible to the plant-derived ricin toxin. The skilled person understands that the toxicity of ricin depends is variable and should be assessed for toxicity in the plant species of interest (see Olsnes and Pihl, *Molecular Action of Toxins and Viruses*, pages 51-105, Amsterdam: Elsevier Biomedical Press (1982)).

The present invention relates to the use of floral organ selective regulatory elements derived from AGL2, AGL4 or AGL9, which are "AGAMOUS-LIKE" or "AGL" genes.

AGAMOUS (AG) is a floral organ identity gene, one of a related family of transcription factors that, in various combinations, specify the identity of the floral organs: the petals, sepals, stamens and carpels (Bowman et al., *Devel.* 112:1-20 (1991); Weigel and Meyerowitz, *Cell* 78:203-209 (1994); Yanofsky, *Annual Rev. Plant Physiol. Mol. Biol.* 46:167-188 (1995)). The AGAMOUS gene product is essential for specification of carpel and stamen identity (Bowman et al., *The Plant Cell* 1:37-52 (1989); Yanofsky et al., *Nature* 346:35-39 (1990)). Related genes have recently been identified and denoted "AGAMOUS-LIKE" or "AGL" genes (Ma et al., *Genes Devel.* 5:484-495 (1991); Mandel and Yanofsky, *The Plant Cell* 7:1763-1771 (1995), which is incorporated herein by reference).

AGL2, AGL4 and AGL9, like AGAMOUS and other AGL genes, are characterized, in part, in that each is a plant MADS box gene. The plant MADS box genes generally encode proteins of about 260 amino acids including a highly conserved MADS domain of about 56 amino acids (Riechmann and Meyerowitz, *Biol. Chem.* 378:1079-1101 (1997), which is incorporated herein by reference). The MADS domain, which was first identified in the *Arabidopsis* AGAMOUS and *Antirrhimum majus* DEFICIENS genes, is conserved among transcription factors found in humans (serum response factor; SRF) and yeast (MCM1; Norman et al., *Cell* 55:989-1003 (1988); Passmore et al., *J. Mol. Biol.* 204:593-606 (1988), and is the most highly conserved region of the MADS domain proteins. The MADS domain is the major determinant of sequence specific DNA-binding activity and can also perform dimerization and other accessory functions (Huang et al., *The Plant Cell* 8:81-94 (1996)). The MADS domain frequently resides at the amino-terminus, although some proteins contain additional residues amino-terminal to the MADS domain.

The "intervening domain" or "I-domain," located immediately C-terminal to the MADS domain, is a weakly conserved domain having a variable length of approximately 30 amino acids (Purugganan et al., *Genetics* 140:345-356 (1995)). In some proteins, the I-domain plays a role in the formation of DNA-binding dimers. A third domain present in plant MADS domain proteins is a moderately conserved 70 amino acid region denoted the "keratin-like domain" or "K-domain." Named for its similarity to regions of the keratin molecule, the structure of the K-domain appears capable of forming amphipathic helices and may mediate protein-protein interactions (Ma et al., *Genes Devel.* 5:484-495 (1991)). The most variable domain, both in sequence and in length, is the carboxy-terminal or "C-domain" of the MADS domain proteins. Dispensable for DNA binding and protein dimerization in some MADS domain proteins, the function of the C-domain remains unknown.

The amino acid sequence of *Arabidopsis* AGL2, a protein with a calculated molecular mass of about 28.5 kDa, is shown in FIGS. 4 and 11a through 11b. Like other AGAMOUS-LIKE proteins, AGL2 has a highly conserved MADS domain and a K domain (Ma et al., *Genes Devel.* 5:484-495 (1991). RNA dot blot hybridization was used to analyze AGL2 expression in immature seed pods, flowers, stems, and leaves. AGL2 RNA was preferentially expressed in flowers: a strong hybridization signal was seen in flower RNA, with a diminished level seen in RNA from immature seed pods. A faint signal was also detected in leaves. To determine whether AGL2 is expressed in an organ-specific manner, in situ hybridization was performed with wild type *Arabidopsis* inflorescence sections. The results showed that AGL2 was expressed mainly in carpels and was concentrated there in the ovules. In addition, AGL2 was expressed at a lower level in the stamens, with expression restricted to the anthers. Thus, the AGL2 gene is selectively expressed in floral organs, with a high level of expression seen in flowers and young seed pods and a much lower level of expression seen in leaves. These results indicate that an AGL2 regulatory element can confer floral organ selective expression upon a heterologous linked gene.

The amino acid sequence of AGL4 is shown in FIGS. 4 and 10a through 10b. The encoded protein, which has a calculated molecular mass of 28.5 kDa, has the characteristic highly conserved MADS domain. RNA dot blot hybridization was used to assess AGL4 expression in immature seed pods, flowers, stems, and leaves. AGL4 was highly expressed in flowers with the expression continuing at a lower level in immature seed pods. No expression was seen in the vegetative stems and leaves. These results indicate that AGL4 is specifically expressed in flowers and that an AGL4 regulatory element can confer floral organ selective expression upon a heterologous linked gene.

*Arabidopsis* AGL9 is a 251 amino acid protein having a calculated molecular mass of 29 kDa. AGL9 has a highly conserved MADS domain, as well as a K domain (see FIG. 5). The protein encoded by *Arabidopsis* AGL9 has a high degree of similarity to the products of the TM5 gene from tomato (*Lycopersicum esculentum*); the petunia gene FBP2, and the DEFH200 gene from *Antirrhinum majus*, indicating that TM5, FBP2 and DEFH200 are AGL9 orthologs (Pnueli et al., *Plant J.* 1:255-266 (1991); Angenent et al., *Plant Cell* 4:983-993 (1992); and Davies et al., *EMBO J.* 15:4330-4343 (1996), each of which is incorporated herein by reference). Throughout the first 160 amino acids, AGL9 shares approximately 89% amino acid identity with the FBP2, TM5 and DEFH200 gene products.

AGL9 RNA accumulates only in flowers, with RNA blot analysis showing no detectable expression in roots, stems or cauline leaves. In situ hybridization analyses demonstrated that AGL9 RNA begins to accumulate after the onset of expression of the floral meristem identity genes but before the expression of the floral organ identity genes. In particular, floral meristem identity genes such as AP1 and CAL are first expressed during stage 1 flower primordia, followed by AGL2 and AGL4, which are first expressed throughout stage 2 flower primordia. AGL9 is subsequently expressed late in stage 2 in a region that does not include the outer perimeter of the flower primordium. Later in flower development, AGL9 RNA accumulates in the petal, stamen, and carpel organs. Thus, AGL9 is specifically expressed only in floral organs, indicating that an AGL9 regulatory element can confer floral organ selective expression upon a heterologous linked gene.

The amino acid sequence of AP1 is shown in FIG. 8a through 8b (Mandel, 1992 Nature 360:273-277). The encoded protein, which has a calculated molecular mass of 30 kDa, has the characteristic highly conserved MADS domain. The deduced AP1 protein is similar to the snapdragon SQUAMOSA protein, sharing 68% identical amino acid residues (Huijser et al., EMBO J. 33:1239-1249; 1992). RNA blot hybridization was used to assess AP1 expression in roots, stems, leaves, and flowers, where it was shown to be flower specific (Id., FIG. 3). Subsequent RNA tissue in situ hybridizations further defined the AP1 RNA accumulation patter where it was shown to first be expressed in a young flower primordium (a flower meristem) when it first becomes visible on the flanks of the shoot meristem. Additional studies showed that AP1 RNA accumulates in all cells of the young flower, and that in mature flowers, AP1 is expressed in sepals and petals but not in stamens and carpels (Id., FIG. 4). Thus, AP1 is specifically expressed in flowers and that an AP1 regulatory element can confer floral organ selective expression upon a heterologous linked gene. Proof of this concept came from fusing the AP1 regulatory region to the easily assayable "GUS" marker gene and the subsequent generation of transgenic plants that had stably integrated the AP1::GUS transgene into the plant nuclear genome (the POP10 construct and resulting lines)(See FIG. 9).

The AP1 regulatory region includes the 1.7 kb of the AP1 "promoter" (the promoter is defined as the 1700 bp immediately upstream of the AP1 translation initiation codon, ATG), as well as the genomic region containing all AP1 intronic sequences. Both the "full length" AP1 promoter (AP1 promoter plus all genomic regions containing AP1 intronic sequences as shown for the POP10 construct in FIG. 7) and the 1700 bp AP1 promoter fragment are sufficient to express foreign genes that are operably linked to it within flowers, and thus may be suitable for suppressing flowering. Smaller constructs, such as those that do not contain all of the AP1 intronic sequences, may also be flower specific, and thus it is not necessary to include all of the AP1 genomic sequences to achieve complete flower-specific regulation. However, the use of the "full length" AP1 regulatory region may be used for optimal flower specific expression, since these sequences will drive gene expression only in flowers.

As used herein, the term "floral organ selective regulatory element" refers to a regulatory element such as a 5', 3' or intronic regulatory element that, when operatively linked to a nucleotide sequence, confers selective expression upon the operatively linked nucleotide sequence in a limited number of plant tissues, including one or more floral organs or subparts thereof. Thus, a floral organ selective regulatory element, as defined herein, confers selective expression in the petals, sepals, stamens or carpels of a plant or in some cell types within the petals, sepals, stamens or carpels, with expression low or absent in other tissues of the plant.

A floral organ selective regulatory element can confer specific expression exclusively in cells of one or more floral organ, or can confer selective expression in a limited number of plant cell types including cells of one or more floral organ. For example, an AGL9 regulatory element, which confers specific expression in flowers, without conferring expression in vegetative tissues such as roots, stems or cauline leaves, is a floral organ selective regulatory element as defined herein. A floral organ selective regulatory element also can be, for example, an AGL2 regulatory element, which confers high level expression in flowers, with a minimal level of expression in leaves.

As used herein, the term "AGL2 regulatory element" refers to a regulatory element derived from *Arabidopsis* AGL2 (SEQ ID NO:5) or an ortholog of *Arabidopsis* AGL2. An AGL2 ortholog is a MADS box gene product expressed, at least in part, in one or more floral organs of a plant and having homology to the amino acid sequence of *Arabidopsis* AGL2 (SEQ ID NO:5). An AGL2 ortholog can be, for example, a pine or rice ortholog such as PrMADS1 or OsMADS5 (Mouradov et al., *Plant Physiol.* 117:55-62 (1998); Kang and An, *Mol. Cells* 7:45-51 (1997), each of which is incorporated herein by reference) or can be another ortholog such as a *Eucalyptus* or spruce ortholog. An AGL2 ortholog generally has at least about 80% amino acid identity with amino acids 1 to 160 of *Arabidopsis* AGL2 (SEQ ID NO:5) and can have, for example, at least about 85%, 90%, or 95% amino acid identity with amino acids 1 to 160 of *Arabidopsis* AGL2 (SEQ ID NO:5).

As used herein, the term "AGL4 regulatory element" refers to a regulatory element derived from *Arabidopsis* AGL4 (SEQ ID NO:7) or an ortholog of *Arabidopsis* AGL4. An AGL4 ortholog is a MADS box gene product expressed, at least in part, in one or more floral organs of a plant and having homology to the amino acid sequence of *Arabidopsis* AGL4 (SEQ ID NO:7). An AGL4 ortholog can be, for example, a *Eucalyptus*, pine or spruce ortholog. An AGL4 ortholog generally has at least about 80% amino acid identity with amino acids 1 to 160 of *Arabidopsis* AGL4 (SEQ ID NO:7) and can have, for example, at least about 85%, 90%, or 95% amino acid identity with amino acids 1 to 160 of *Arabidopsis* AGL4 (SEQ ID NO:7).

As used herein, the term "AGL9 regulatory element" refers to a regulatory element derived from *Arabidopsis* AGL9 (SEQ ID NO:9) or an ortholog of *Arabidopsis* AGL9. An AGL9 ortholog is a MADS box gene product expressed, at least in part, in one or more floral organs of a plant and having homology to the amino acid sequence of *Arabidopsis* AGL9 (SEQ ID NO:9). An AGL9 ortholog can be, for example, a tomato, petunia or *A. majus* ortholog such as TM5, FBP2 or DEFH200 (Pnueli et al., *The Plant Cell* 6:163-173 (1994); Angenent et al., *Plant Cell* 4:983-993 (1992); and Davies et al., *EMBO J.* 15:4330-4343 (1996)) or can be, for example, a *Eucalyptus*, pine or spruce ortholog. An AGL9 ortholog generally has at least about 80% amino acid identity with amino acids 1 to 160 of *Arabidopsis* AGL9 (SEQ ID NO:9) and can have, for example, at least about 85%, 90%, or 95% amino acid identity with amino acids 1 to 160 of *Arabidopsis* AGL9 (SEQ ID NO:9).

As used herein the term "AP1 regulatory element" refers to a regulatory element derived from *Arabidopsis* AP1 (SEQ ID NO:12) or an ortholog of *Arabidopsis* AP1. An AP1 ortholog is a MADS box gene product expressed, at least in part, in one or more floral organs of a plant and having homology to the amino acid sequence of *Arabidopsis* AP1 (SEQ ID NO:12). An AP1 ortholog can be, for example, a snapdragon ortholog, such as SQUAMOSA. Also, an AP1 ortholog could be, for example, a *Eucalyptus*, pine or spruce ortholog. An AP1 ortholog generally has at least about 75% amino acid identity with amino acids 1 to 160 of *Arabidopsis* AP1 (SEQ ID NO:12) and can have, for example, at least about 85%, 90%, or 95% amino acid identity with amino acids 1 to 160 of *Arabidopsis* AP1 (SEQ ID NO:12).

Preferably, an AGL2, AGL4 or AGL9 or AP1 floral organ selective regulatory element is orthologous to the transgenic plant species into which it is introduced. An AGL2 promoter (SEQ ID NO:1) or active fragment thereof, for example, can be introduced into an *Arabidopsis* plant to produce a transgenic *Arabidopsis* variety characterized by suppressed flowering. Similarly, a *Eucalyptus* AGL2, AGL4 or AGL9 or AP1 floral organ selective regulatory element can be introduced into a *Eucalyptus* plant to produce a transgenic *Eucalyptus* variety characterized by suppressed flowering.

An AGL2, AGL4 or AGL9 or AP1 floral organ selective regulatory element also can be introduced into a heterologous plant to produce a transgenic plant of the invention characterized by suppressed flowering. AGAMOUS-like gene products have been widely conserved throughout the plant kingdom; for example, AGAMOUS has been conserved in tomato (TAG1) and maize (ZAG1), indicating that orthologs of AGAMOUS-like genes are present in most, if not all, angiosperms (Pnueli et al., *The Plant Cell* 6:163-173 (1994); Schmidt et al., *The Plant Cell* 5:729-737 (1993)). Furthermore, it has been shown that MADS-box genes exist in gymnosperms and angiosperms as well as in ferns, the common ancestors of contemporary seed plants (Tandre et al., *Plant Mol. Biol.* 27:69-78 (1995); Liu and Podila, *Plant Phys.* 113: 665 (1997); Münster et al., *Proc. Natl. Acad. Sci., USA* 94:2145-2420 (1997); and Mouradov et al., *Plant Physiol.* 117:55-62 (1998)). AGL2, AGL4 and AGL9 floral organ selective regulatory elements also can be conserved and can function across species boundaries to confer floral organ selective expression in heterologous plant species. Thus, an *Arabidopsis* AGL2, AGL4 or AGL9 or AP1 floral organ selective regulatory element, such as the *Arabidopsis* AGL2, AGL4 or AGL9 or AP1 promoter SEQ ID NO:1, SEQ ID NO:2 or SEQ ID NO:3 or SEQ ID NO:12, or an active fragment thereof, can confer floral organ selective expression upon an operatively linked nucleotide sequence encoding a cytotoxic gene product in a heterologous plant such as *Eucalyptus*, whereby the cytotoxic gene product is selectively expressed in floral tissue and flowering is suppressed.

A transgenic plant of the invention that is characterized by suppressed flowering can be one of a variety of plant species. As used herein, the term "plant" means a higher plant that generally is a vascular plant or seed plant such as an angiosperm or gymnosperm. An angiosperm is a seed-bearing plant whose seeds are borne in a mature ovary (fruit) and are divided into two broad classes based on the number of cotyledons or seed leaves that generally store or absorb food. A gymnosperm is a seed-bearing plant with seeds not enclosed in an ovary. In view of the above, the skilled person understands that the invention can be practiced, for example, with a monocotyledonous or dicotyledonous angiosperm or gymnosperm as desired.

In one embodiment, the invention provides a transgenic woody plant that is characterized by suppressed flowering. A transgenic plant of the invention can be, for example, a perennial woody plant such as a tree or shrub. For example, dicot trees such as alder, ash, basswood, beech, birch, cherry, cottonwood, elm, hickory, locust, maple, red and white oak, persimmon, sycamore, walnut, and poplar can be modified as disclosed herein to produce transgenic varieties in which flowering is suppressed. In addition, conifer woods, for example, cedar; Douglas fir; hemlock; loblolly, ponderosa, slash, sugar and western white pines; redwood; and spruce trees can be modified to produce transgenic varieties in which flowering is suppressed. The skilled person understands that the invention can be practiced with these or other shrubs or trees, especially trees useful for producing lumber, pulp or paper (Whetten and Sederoff, *Forest Ecology and Management* 43:301-316 (1991), which is incorporated herein by reference).

The present invention further provides tissues derived from a transgenic plant of the invention. Such tissues are derived from a transgenic plant that is characterized by suppressed flowering and that contains a nucleic acid molecule including a floral organ selective regulatory element operatively linked to a nucleotide sequence encoding a cytotoxic gene product.

As used herein, the term "tissue" means an aggregate of plant cells and intercellular material organized into a structural and functional unit. A particularly useful tissue of the invention is a tissue that can be vegetatively or non-vegetatively propagated such that the transgenic plant from which the tissue was derived is reproduced. A tissue of the invention can be, for example, a leaf, root, stem or part thereof.

The present invention also provides an isolated nucleic acid molecule including an AGL2, AGL4 or AGL9 or AP1 regulatory element, which confers selective expression upon an operatively linked nucleotide sequence in one or more floral organs of a plant. The isolated nucleic acid molecule can further include, if desired, an operatively linked nucleotide sequence encoding a cytotoxic gene product. The encoded cytotoxic gene product can be, for example, diphtheria toxin A chain, RNase T1, Barnase RNase, ricin toxin A chain, or the herpes simplex virus thymidine kinase gene product.

The *Arabidopsis* AGL2 promoter (SEQ ID NO:1) is shown in FIG. 1. An AGL2 regulatory element, such as a 5' regulatory element or intronic regulatory element, can confer selective expression in one or more floral organs such as carpels and stamens and, thus, is a floral organ selective regulatory element as defined herein. An isolated AGL2 floral organ selective regulatory element can have, for example, at least fifteen contiguous nucleotides of the *Arabidopsis* AGL2 sequence SEQ ID NO:1. Such an isolated AGL2 floral organ selective regulatory element can have, for example, at least 16, 18, 20, 25, 30, 40, 50, 100 or 500 contiguous nucleotides of SEQ ID NO:1 and is characterized, in part, by the ability to confer floral organ selective expression upon an operatively linked nucleotide sequence (see Example I).

The *Arabidopsis* AGL4 promoter (SEQ ID NO:2) is shown in FIG. 2. An AGL4 regulatory element confers selective expression in one or more floral organs without conferring expression in vegetative tissues and, thus, is a floral organ selective regulatory element as defined herein. An isolated AGL4 floral organ selective regulatory element can have, for example, at least fifteen contiguous nucleotides of the *Arabidopsis* AGL4 sequence SEQ ID NO:2. Such an isolated AGL4 floral organ selective regulatory element can have, for example, at least 16, 18, 20, 25, 30, 40, 50, 100 or 500 contiguous nucleotides of SEQ ID NO:2 and is characterized, in part, by the ability to confer floral organ selective expression upon an operatively linked nucleotide sequence (see Example II).

The *Arabidopsis* AGL9 promoter (SEQ ID NO:3) is shown in FIG. 3. An AGL9 regulatory element, such as a 5' regulatory element or intronic regulatory element, can confer selective expression in one or more floral organs, specifically in petals, stamens and carpels, and, thus, is a floral organ selective regulatory element as defined herein. An isolated AGL9 floral organ selective regulatory element can have, for example, at least fifteen contiguous nucleotides of the *Arabidopsis* AGL9 sequence SEQ ID NO:3. Such an isolated AGL9 floral organ selective regulatory element can have, for example, at least 16, 18, 20, 25, 30, 40, 50, 100 or 500 contiguous nucleotides of SEQ ID NO:3 and is characterized, in part, by the ability to confer floral organ selective expression upon an operatively linked nucleotide sequence (see Example III).

The *Arabidopsis* AP1 promoter (SEQ ID NO:12) is shown in FIG. 6. An AP1 regulatory element, such as a 5' regulatory element or intronic regulatory element, can confer selective expression in one or more floral organs, specifically in petals, stamens and carpels, and, thus, is a floral organ selective regulatory element as defined herein. An isolated AP1 floral organ selective regulatory element can have, for example, at least fifteen contiguous nucleotides of the *Arabidopsis* AP1 sequence SEQ ID NO:12. Such an isolated AP1 floral organ selective regulatory element can have, for example, at least 16, 18, 20, 25, 30, 40, 50, 100 or 500 contiguous nucleotides of SEQ ID NO:12 and is characterized, in part, by the ability to confer floral organ selective expression upon an operatively linked nucleotide sequence (see Example IV).

As used herein, the term "substantially the nucleotide sequence," when used in reference to an AGL2, AGL4 or AGL9 or AP1 regulatory element, means a nucleotide sequence having an identical sequence, or a nucleotide sequence having a similar, non-identical sequence that is considered to be a functionally equivalent sequence by those skilled in the art. For example, a floral organ selective regulatory element that is an AGL2 regulatory element can have, for example, a nucleotide sequence identical to the sequence of the *Arabidopsis* AGL2 promoter (SEQ ID NO:1) shown in FIG. 1, or a similar, non-identical sequence that is functionally equivalent. A floral organ selective regulatory element can have, for example, one or more modifications such as nucleotide additions, deletions or substitutions relative to the AGL2 promoter sequence shown in FIG. 1, provided that the modified nucleotide sequence retains substantially the ability to confer selective expression in one or more floral organs upon an operatively linked nucleotide sequence, such as a nucleotide sequence encoding a cytotoxic gene product.

It is understood that limited modifications can be made without destroying the biological function of an AGL2, AGL4 or AGL9 or AP1 regulatory element and that such limited modifications can result in floral organ selective regulatory elements that have substantially equivalent or enhanced function as compared to a wild type AGL2, AGL4 or AGL9 or AP1 regulatory element. These modifications can be deliberate, as through site-directed mutagenesis, or can be accidental such as through mutation in hosts harboring the regulatory element. All such modified nucleotide sequences are included in the definition of a floral organ selective regulatory element as long as the ability to confer selective expression in one or more floral organs is substantially retained.

A floral organ selective regulatory element can be derived from a gene that is an ortholog of *Arabidopsis* AGL2, AGL4 or AGL9 or AP1 and that is selectively expressed in one or more floral organs of the orthologous plant. An AGL2, AGL4 or AGL9 or AP1 floral organ selective regulatory element can be derived, for example, from an AGL2, AGL4 or AGL9 or AP1 ortholog such as a *Eucalyptus*, pine or spruce ortholog.

Floral organ selective regulatory elements also can be derived from a variety of other genes that are selectively expressed in one or more floral organs of a plant and can be identified and isolated using routine methodology. Differential screening strategies using, for example, RNA prepared from a floral organ and RNA prepared from non-floral material such as leaf or root tissue can be used to isolate cDNAs selectively expressed in cells of one or more floral organs; subsequently, the corresponding genes are isolated using the cDNA sequence as a probe.

Enhancer trap or gene trap strategies also can be used to identify and isolate a floral organ selective regulatory element (Sundaresan, et al., *Genes Dev.* 9, 1797-1810 (1995); Koncz et al., *Proc. Natl. Acad. Sci. USA* 86:8467-8471 (1989); Kertbundit et al., *Proc. Natl. Acad. Sci. USA* 88:5212-5216 (1991); Topping et al., *Development* 112:1009-1019 (1991), each of which is incorporated herein by reference). Enhancer trap elements include a reporter gene such as GUS with a weak or minimal promoter, while gene trap elements lack a promoter sequence, relying on transcription from a flanking chromosomal gene for reporter gene expression. Transposable elements included in the constructs mediate fusions to endogenous loci; constructs selectively expressed in one or more floral organs are identified by their pattern of expression. With the inserted element as a tag, the flanking floral organ selective regulatory element is cloned using, for example, inverse polymerase chain reaction methodology (see, for example, Aarts et al., *Nature* 363:715-717 (1993); see, also, Ochman et al., "Amplification of Flanking Sequences by Inverse PCR," in Innis et al. (Ed.), *PCR Protocols*, San Diego: Academic Press, Inc. (1990)). The Ac/Ds transposition system of Sundaresan, et al., *Genes Dev.* 9, 1797-1810 (1995), can be particularly useful in identifying and isolating a floral organ selective regulatory element useful in the invention.

Floral organ selective regulatory elements also can be isolated by inserting a library of random genomic DNA fragments in front of a promoterless reporter gene and screening transgenic plants transformed with the library for floral organ selective reporter gene expression. The promoterless vector pROA97, which contains the npt gene and the GUS gene each under the control of the minimal 35S promoter, can be useful for such screening. The genomic library can be, for example, Sau3A fragments of *Arabidopsis thaliana* genomic DNA or genomic DNA from, for example, *Eucalyptus*, pine or spruce (Ott et al., *Mol. Gen. Genet.* 223:169-179(1990); Claes et al., *The Plant Journal* 1:15-26(1991), each of which is incorporated herein by reference).

An active fragment of an AGL2, AGL4 or AGL9 or AP1 promoter, which contains a floral organ selective regulatory element, can be identified by routine techniques, for example, using a reporter gene and in situ expression analysis. The GUS and firefly luciferase reporter genes are particularly useful for in situ localization of plant gene expression (Jefferson et al., *EMBO J.* 6:3901 (1987); Ow et al., *Science* 334:856 (1986), each of which is incorporated herein by reference), and promoterless vectors containing the GUS expression cassette are commercially available, for example, from Clontech (Palo Alto, Calif.). To identify an active fragment containing a floral organ selective regulatory element such as an AGL2, AGL4 or AGL9 or AP1 regulatory element, one or more nucleotide portions of an AGL2, AGL4 or AGL9 or AP1 gene can be generated using enzymatic or PCR-based methodology (Glick and Thompson (eds.), *Methods in Plant Molecular Biology and Biotechnology*, Boca Raton, Fla.: CRC Press (1993); Innis et al. (Ed.), *PCR Protocols*, San Diego: Academic Press, Inc. (1990)); the resulting segments are fused to a reporter gene such as GUS and analyzed as described above.

The present invention also provides a kit for producing a transgenic plant characterized by suppressed flowering. A kit of the invention comprises packaging containing a plant expression vector having a floral organ selective regulatory element operatively linked to a nucleotide sequence encoding a cytotoxic gene product. The plant expression vector can include, if desired, a nucleotide sequence encoding a selectable marker or reporter gene, along with instructions to employ the vector in accord with the present method.

The term "plant expression vector," as used herein, is a self-replicating nucleic acid molecule that provides a means to transfer an exogenous nucleic acid molecule into a plant host cell and to express the molecule therein. Plant expression vectors encompass vectors suitable for *Agrobacterium*-mediated transformation, including binary and cointegrating vectors, as well as vectors for physical transformation.

Plant expression vectors can be used for transient expression of the exogenous nucleic acid molecule, or can integrate and stably express the exogenous sequence. One skilled in the art understands that a plant expression vector can contain all the functions needed for transfer and expression of an exogenous nucleic acid molecule; alternatively, one or more functions can be supplied in trans as in a binary vector system for *Agrobacterium*-mediated transformation.

In addition to a floral organ selective regulatory element and a nucleotide sequence encoding a cytotoxic gene product, a plant expression vector of the invention can contain, if desired, additional elements. A binary vector for *Agrobacterium*-mediated transformation contains one or both T-DNA border repeats and can also contain, for example, one or more of the following: a broad host range replicon, an ori T for efficient transfer from *E. coli* to *Agrobacterium*, a bacterial selectable marker such as ampicillin and a polylinker containing multiple cloning sites.

A plant expression vector for physical transformation can have, if desired, a plant selectable marker or a reporter gene or both, in addition to a floral organ selective regulatory element in vectors such as pBR322, pUC, pGEM and M13, which are commercially available, for example, from Pharmacia (Piscataway, N.J.) or Promega (Madison, Wis.).

A selectable marker gene or a reporter gene can facilitate the identification and selection of transformed plants, or plant cells. Both selectable marker and reporter genes may be flanked with appropriate regulatory sequences to enable expression in plants. Useful selectable markers are well known in the art and include, for example, antibiotic and herbicide resistance genes. Specific examples of such genes are disclosed in Weising, K., et al., *Ann. Rev. Genet.*, 22, 421-478 (1988). Selectable marker genes includes the hygromycin B phosphotransferase coding sequence, which confers resistance to hygromycin B; the aminoglycoside phosphotransferase gene of transposon Tn5 (AphII), which encodes resistance to the antibiotics kanamycin, neomycin and G418; and genes which code for resistance or tolerance to glyphosate, 1,2-dicholoropropionic acid methotrexate, imidazolinones, sulfonylureas, bromoxynil, phophononthricin and the like.

Reporter genes which encode for easily assayable marker proteins are well known in the art. IN general, a reporter gene is a gene which ins not present in or expressed by the recipient organism or tissue and which encodes a protein whose expression is manifested by some easily detectable property, e.g., phenotypic change or enzymatic activity. Examples of such gene are provided in Weising, et al., *Ann. Rev. Genet.*, 22, 421-478 (1988).

In plant expression vectors for physical transformation of a plant, the T-DNA borders or the ori T region can optionally be included but provide no advantage.

Also provided by the present invention is a method of producing a transgenic plant characterized by suppressed flowering. The method includes the step of introducing into a plant an exogenous nucleic acid molecule containing a floral organ selective regulatory element operatively linked to a nucleotide sequence encoding a cytotoxic gene product, where flowering is suppressed due to selective expression of the exogenous nucleic acid molecule and where the floral organ selective regulatory element is an AGL2 regulatory element, an AGL4 regulatory element or an AGL9 regulatory element or an AP1 regulatory element.

Methods for producing the desired recombinant nucleic acid molecule under control of an AGL2, AGL4 or AGL9 or AP1 floral organ selective regulatory element and for producing a transgenic plant of the invention are well known in the art (see, generally, Sambrook et al. (eds.) *Molecular Cloning: A Laboratory Manual* (Second Edition, Plainview, N.Y.: Cold Spring Harbor Laboratory Press (1989); Glick and Thompson, supra, 1993).

An exogenous nucleic acid molecule can be introduced into a plant using a variety of transformation methodologies including *Agrobacterium*-mediated transformation and direct gene transfer methods such as electroporation and microprojectile-mediated transformation (see, generally, Wang et al. (eds), *Transformation of Plants and Soil Microorganisms*, Cambridge, UK: University Press (1995), which is incorporated herein by reference).

Transformation methods based upon the soil bacterium *Agrobacterium tumefaciens* are particularly useful for introducing an exogenous nucleic acid molecule into a plant. The wild type form of *Agrobacterium* contains a Ti (tumor-inducing) plasmid that directs production of tumorigenic crown gall growth on host plants. Transfer of the tumor-inducing T-DNA region of the Ti plasmid to a plant genome requires the Ti plasmid-encoded virulence genes as well as T-DNA borders, which are a set of direct DNA repeats that delineate the region to be transferred. An *Agrobacterium*-based vector is a modified form of a Ti plasmid, in which the tumor inducing functions are replaced by the nucleic acid sequence of interest to be introduced into the plant host.

*Agrobacterium*-mediated transformation generally employs cointegrate vectors or, preferably, binary vector systems, in which the components of the Ti plasmid are divided between a helper vector, which resides permanently in the *Agrobacterium* host and carries the virulence genes, and a shuttle vector, which contains the gene of interest bounded by T-DNA sequences. A variety of binary vectors are well known in the art and are commercially available, for example, from Clontech (Palo Alto, Calif.). Methods of coculturing *Agrobacterium* with cultured plant cells or wounded tissue such as leaf tissue, root explants, hypocotyledons, stem pieces or tubers, for example, also are well known in the art (Glick and Thompson, supra, 1993). Wounded cells within dicot plant tissue that have been infected by *Agrobacterium* can develop organs de novo when cultured under the appropriate conditions; the resulting transgenic shoots eventually give rise to transgenic plants that ectopically express a nucleic acid molecule containing a floral organ selective regulatory element operatively linked to a nucleotide sequence encoding a cytotoxic gene product. *Agrobacterium* also can be used for transformation of whole plants as described in Bechtold et al., *C.R. Acad. Sci. Paris, Life Sci.* 316:1194-1199 (1993), which is incorporated herein by reference).

Microprojectile-mediated transformation also can be used to produce a transgenic plant containing a nucleic acid molecule including a floral organ selective regulatory element operatively linked to a nucleotide sequence encoding a cytotoxic gene product. This method, as described by Lundquist et al., U.S. Pat. No. 5,554,798, which is incorporated herein by reference), relies on microprojectiles such as gold or tungsten that are coated with the desired nucleic acid molecule by precipitation with calcium chloride, spermidine or PEG. The microprojectile particles are accelerated at high speed into an angiosperm tissue using a device such as the BIOLISTIC PD-1000 (Biorad; Hercules Calif.).

Microprojectile-mediated delivery or "particle bombardment" is especially useful to transform plants that are difficult to transform or regenerate using other methods. Microprojectile-mediated transformation has been used, for example, to generate a variety of transgenic plant species, including cotton, tobacco, corn, hybrid poplar and papaya (see Glick and Thompson, supra, 1993) as well as cereal crops such as wheat, oat, barley, sorghum and rice (Duan et al., *Nature Biotech.* 14:494-498 (1996); Shimamoto, *Curr. Opin. Biotech.* 5:158-162 (1994), each of which is incorporated herein by reference). In view of the above, the skilled artisan will recognize that *Agrobacterium*-mediated or microprojectile-mediated transformation, as disclosed herein, or other methods known in the art can be used to produce a transgenic plant of the invention characterized by suppressed flowering.

Following transformation via any method, it is necessary to identify and select those plants or cells which both contain the heterologous DNA and still retain sufficient regenerative capacity. There are two general approaches which have been found useful for accomplishing this. First, the transformed calli or plants regenerated therefrom can be screened for the presence of the heterologous DNA by various standard methods which could include assays for the expression of reporter genes or assessment of phenotypic effects of the heterologous DNA, if any. Alternatively, and preferably, when a selectable marker gene has been transmitted along with or as part of the heterologous DNA, those cells of the callus or plant which have been transformed can be identified by the use of a selective agent to detect expression of the selectable marker gene.

Selection of the putative transformants is a critical part of the successful transformation process since selection conditions must be chosen so as to allow growth and accumulation of the transformed cells or plants while simultaneously inhibiting the growth of the non-transformed cells or plants.

Selection procedures involve exposure to a toxic agent and may employ sequential changes in the concentration of the agent and multiple rounds of selection. The particular concentrations and cycle lengths are likely to need to be varied for each particular agent. A currently preferred selection procedure entails using an initial selection round at a relatively low toxic agent concentration and then later round(s) at higher concentration(s). This allows the selective agent to exert its toxic effect slowly over a longer period of time. Preferably, the concentration of the agent is initially such that about a 5-40% level of growth inhibition will occur, as determined from a growth inhibition curve. The effect may be to allow the transformed cells or plants to preferentially grow and divide while inhibiting untransformed cells or plants, but not to the extent that growth of the transformed cells or plants is prevented. Once the few individual transformed cells or plants have grown sufficiently, the tissue may be shifted to media containing a higher concentration of the toxic agent to kill essentially all untransformed cells. The shift to the higher concentration also reduces the possibility of non-transformed cells or plants habituating to the agent. The higher level is preferably in the range of about 30 to 100% growth inhibition. The length of the first selection cycle may be from about 1 to 4 weeks, preferably about 2 weeks. Later selection cycles may be from about 1 to about 12 weeks, preferably about 2 to about 10 weeks. Putative transformants can generally be identified as viable plants. In the case of transformation of cells, putative transformants can generally be identified as proliferating sectors of tissue among a background of non-proliferating cells.

Once a putative transformant is identified, transformation can be confirmed by phenotypic and/or genotypic analysis. If a selection agent is used, an example of phenotypic analysis is to visually inspect the plants. The plants which appear to be green, growing, and healthy are compared to a control on various levels of the selective agent. Another example of phenotypic analysis is to measure the increase in fresh weight of the putative transformant as compared to a control on various levels of the selective agent. Other analyses that may be employed will depend on the function of the heterologous DNA. For example, if an enzyme or protein is encoded by the DNA, enzymatic or immunological assays specific for the particular enzyme or protein may be used. Other gene products may be assayed by using a suitable bioassay or chemical assay. Other such techniques are well known in the art and are not repeated here. The presence of the gene can also be confirmed by conventional procedures, i.e., Southern blot or polymerase chain reaction (PCR) or the like.

EXAMPLE I

An AGL2 Regulatory Element Directs Floral Organ Selective Expression

This example shows that a fragment of the *Arabidopsis* AGL2 promoter is sufficient to direct floral organ selective gene expression.

*Agrobacterium tumefaciens* strain C58 was used to transform *Arabidopsis thaliana*, ecotype Columbia. The transformation method of this example was disclosed by Bechtold et al., *C. R. Acad. Sci. Paris,* 316:1194-9 (1993)(incorporated by reference herein).

A BglII fragment of approximately 2.3 kb was isolated from the *Arabidopsis* AGL2 promoter (SEQ ID NO:1) shown in FIG. 1 using the BglII sites indicated at nucleotide 1 and nucleotide 1120. The fragment was subcloned into the BamHI site of pGEM3Z (Promega, Madison, Wis.). The resulting plasmid was restricted with SalI and SmaI and subcloned into the corresponding sites of the GUS expression vector pBI101.2 (CLONTECH, Palo Alto, Calif.) to create pKY18. Analysis of GUS expression in kanamycin resistant *Arabidopsis* lines transformed with pKY18 revealed floral specific GUS expression with no significant expression in tissues other than flowers.

These results indicate that the 2.3 kb *Arabidopsis* AGL2 promoter fragment of SEQ ID NO:1 directs floral organ selective expression of a heterologous linked gene product.

EXAMPLE II

An AGL4 Regulatory Element Directs Floral Organ Selective Expression

This example shows that a fragment of the *Arabidopsis* AGL4 promoter is sufficient to direct floral organ selective gene expression.

*Agrobacterium tumefaciens* strain C58 was used to transform *Arabidopsis thaliana*, ecotype Columbia. The transformation method of this example was disclosed by Bechtold et al., *C. R. Acad. Sci. Paris,* 316:1194-9 (1993)(incorporated by reference herein).

AGL4 promoter fragments were isolated from the promoter sequence shown in FIG. 2 (SEQ ID NO:2). A 560 bp AGL4 fragment of SEQ ID NO:2 was prepared containing the region from nucleotide −862 to nucleotide −303 using the HindIII site indicated at nucleotide −862 and an engineered BamHI site. The 560 bp fragment was subcloned into the HindIII and BamHI sites of pGEM3Z (Promega). A 270 bp AGL4 fragment of SEQ ID NO:2 was prepared similarly using the indicated DraI site at nucleotide −573 and an engineered BamHI site at nucleotide −303 and subcloned into the HincII and BamHI sites of pGEM3Z. The 560 bp and 270 bp fragments were subsequently cloned into the GUS expression vector pBI101.1 (CLONTECH) to produce pSR34 and pSR35, respectively.

Plants were transformed with pSR34 and pSR35. GUS staining was observed in the flowers of pSR34 plants. These results demonstrate that the 560 bp fragment of the *Arabidopsis* AGL4 promoter confers floral organ selective expression upon a linked gene.

EXAMPLE III

An AGL9 Regulatory Element Directs Floral Organ Selective Expression

This example shows that a fragment of the *Arabidopsis* AGL9 promoter is sufficient to direct floral organ selective gene expression.

*Agrobacterium tumefaciens* strain C58 was used to transform *Arabidopsis thaliana*, ecotype Columbia. The transformation method of this example was disclosed by Bechtold et al., *C. R. Acad. Sci. Paris,* 316:1194-9 (1993)(incorporated by reference herein).

The entire 1755 bp AGL9 promoter fragment shown in FIG. 3 (SEQ ID NO:3) was cloned into the GUS expression vector pBI101.3 (CLONTECH) to produce pSP112. Multiple transgenic lines containing pSP112 were analyzed for GUS expression. The results showed that GUS was expressed only in floral organs, with no expression evident in other tissues such as stem.

These results demonstrate that an AGL9 promoter is a floral organ selective regulatory element that can confer floral organ selective expression upon an operatively linked encoded gene such as GUS.

EXAMPLE IV

An AP1 Regulatory Element Directs Floral Organ Selective Expression

This example shows that a fragment of the *Arabidopsis* AP1 promoter is sufficient to direct floral selective gene expression.

*Agrobacterium tumefaciens* strain C58 was used to transform *Arabidopsis thaliana*, ecotype Columbia. The transformation method of this example was disclosed by Bechtold et al., *C. R. Acad. Sci. Paris,* 316:1194-9 (1993)(incorporated by reference herein).

Figure 7:
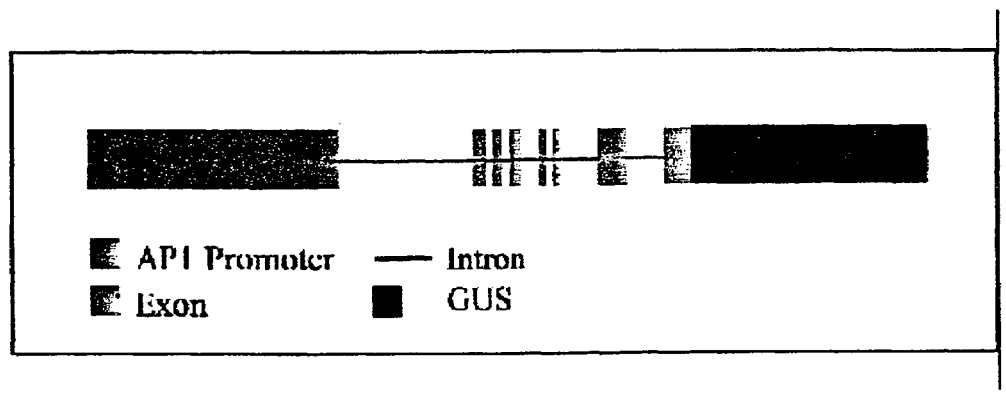
FIG. 7 shows a diagram of reporter construct POP10. The construct has 1.7 kb AP1 promoter plus the entire coding region of AP1 in front of promoterless GUS gene in pBI101.2 plasmid. The construct has 1.7 kb AP1 promoter plus the entire coding region of AP1 in front of promoterless GUS gene in pBI101.2 plasmid. The construct was first made by PCR amplification from intron 3 to the end of AP1 gene in exon 8 (right before stop codon) using KY65 plasmid containing AP1 genomic region as template. The HindIII site was added to the forward primer AP1 HIN [5'-CAAGCTTGTA-CACATTTACACTCATCACAT-3' (SEQ ID NO:17)] and BamHI site was added to reverse primer AP1 BAM, [5'-CGGATCCTGCGCGAAGCAGCCAAGGTTG-3' (SEQ ID NO:18)] to aid cloning (sequence in italic are restriction sites of HindIII and BamHI). The 1.7 kb amplified fragment was cloned into plasmid pBI101.2 using HindIII and BamHI sites giving construct POP9. The 3.6 kb HindIII/XbaI fragment was isolated from KY65 plasmid and cloned into POP9 construct giving POP 10 construct.

The entire 1.7 kb AP1 promoter shown in FIG. 6 (SEQ ID NO:12) plus the entire coding region of AP1 including introns was cloned into the GUS expression vector pBI101.2 to produce the POP10 construct (FIG. 7). The construct was first made by PCR amplification from intron 3 to the end of AP1 gene in exon 8 (right before stop codon) using KY65 plasmid containing AP1 genomic region as template. The HindIII site was added to the forward primer AP1HIN and BamHI site was added to reverse primer AP1BAM to aid cloning. The 1.7 kb amplified fragment was cloned into plasmid pB101.2 using HindIII and BamHI sites giving construct POP9. The 3.6 kb HindIII/XbaI fragment was isolated from KY65 plasmid and cloned into POP9 contruct giving POP 10 contruct.

Multiple transgenic lines containing the POP10 construct were analyzed for GUS expression. The results showed the GUS was expressed specifically in the young flower primordium (See FIG. 9) as soon as it arises on the flanks of the shoot meristem. No GUS staining was seen in the shoot meristem, the stem, leaves, roots, or any part of the plant other than in flowers.

All journal articles, references, and patent citations provided above, in parentheses or otherwise, whether previously stated or not, are incorporated herein by reference.

It should be understood that various modifications can be made without departing from the spirit of the invention. Accordingly, the invention is limited only by the following claims.

REFERENCES CITED

The references listed below are incorporated by reference herein.

Aarts et al., *Nature* 363:715-717 (1993).
Angenent et al., *Plant Cell* 4:983-993 (1992).
Bechtold et al., *C.R. Acad. Sci. Paris, Life Sci.* 316:1194-1199 (1993).
Bowman et al., *Devel.* 112:1-20 (1991).
Bowman et al., *The Plant Cell* 1:37-52 (1989).
Claes et al., *The Plant Journal* 1:15-26 (1991).
Collier, *Bacteriol. Rev.* 39:54-85 (1975).
Davies et al., *EMBO J.* 15:4330-4343 (1996).
Duan et al., *Nature Biotech.* 14:494-498 (1996).

Glick and Thompson (eds.), *Methods in Plant Molecular Biology and Biotechnology*, Boca Raton, Fla.: CRC Press (1993).
Greenfield et al., *Proc. Natl. Acad. Sci., USA* 80:6853-6857 (1983).
Higuchi, "Recombinant PCR" in Innis et al. (Ed.), *PCR Protocols*, San Diego: Academic Press, Inc. (1990).
Huang et al., *The Plant Cell* 8:81-94 (1996).
Huijser et al., *EMBO J.* 33:1239-1249; 1992.
Innis et al. (Ed.), *PCR Protocols*, San Diego: Academic Press, Inc. (1990).
Jefferson et al., *EMBO J.* 6:3901 (1987).
Kang and An, *Mol. Cells* 7:45-51 (1997).
Kertbundit et al., *Proc. Natl. Acad. Sci. USA* 88:5212-5216 (1991).
Koncz et al., *Proc. Natl. Acad. Sci. USA* 86:8467-8471 (1989).
Liu and Podila, *Plant Phys.* 113:665 (1997).
Ma et al., *Genes Devel.* 5:484-495 (1991).
Mandel and Yanofsky, *The Plant Cell* 7:1763-1771 (1995).
Mandel, *Nature* 360:273-277 (1992).
Moffat et al., *Development* 114:681-687 (1992).
Mouradov et al., *Plant Physiol.* 117:55-62 (1998).
Münster et al., *Proc. Natl. Acad. Sci., USA* 94:2145-2420 (1997).
Norman et al., *Cell* 55:989-1003 (1988).
Ochman et al., "Amplification of Flanking Sequences by Inverse PCR," in Innis et al., (Ed.), *PCR Protocols*, San Diego: Academic Press, Inc. (1990).
Olsnes and Pihl, *Molecular Action of Toxins and Viruses*, pages 51-105, Amsterdam: Elsevier Biomedical Press (1982).
Ott et al., *Mol. Gen. Genet.* 223:169-179 (1990).
Ow et al., *Science* 334:856 (1986).
Palmiter et al., *Cell* 50:435-443 (1987).
Passmore et al., *J. Mol. Biol.* 204:593-606 (1988).
Pnueli et al., *Plant J.* 1:255-266 (1991).
Pnueli et al., *The Plant Cell* 6:163-173 (1994).
Purugganan et al., *Genetics* 140:345-356 (1995).
Riechmann and Meyerowitz, *Biol. Chem.* 378:1079-1101 (1997).
Sambrook et al. (eds.) *Molecular Cloning: A Laboratory Manual* (Second Edition, Plainview, N.Y.: Cold Spring Harbor Laboratory Press (1989).
Schmidt et al., *The Plant Cell* 5:729-737 (1993).
Shimamoto, *Curr. Opin. Biotech.* 5:158-162 (1994).
Sundaresan, et al., *Genes Dev.* 9, 1797-1810 (1995).
Tandre et al., *Plant Mol. Biol.* 27:69-78 (1995).
Topping et al., *Development* 112:1009-1019 (1991).
Thorsness and Nasrallah, *Methods in Cell Biology* 50:439-448 (1995).
Wang et al. (eds), *Transformation of Plants and Soil Microorganisms*, Cambridge, UK: University Press (1995).
Weigel and Meyerowitz, *Cell* 78:203-209 (1994).
Weising, K., et al., *Ann. Rev. Genet.*, 22, 421-478 (1988).
Whetten and Sederoff, *Forest Ecology and Management* 43:301-316 (1991).
Yamaizumi et al., *Cell* 15:245-250 (1978).
Yanofsky, *Annual Rev. Plant Physiol. Mol. Biol.* 46:167-188 (1995).
Yanofsky et al., *Nature* 346:35-39 (1990).

SEQUENCE LISTING

```
<160> NUMBER OF SEQ ID NOS: 18

<210> SEQ ID NO 1
<211> LENGTH: 4512
<212> TYPE: DNA
<213> ORGANISM: Arabidopsis thaliana
<220> FEATURE:
<223> OTHER INFORMATION: AGL2 promoter
<220> FEATURE:
<221> NAME/KEY: modified_base
<222> LOCATION: (254)..(260)
<223> OTHER INFORMATION: n = g, a, c or t

<400> SEQUENCE: 1
agatctctat gaaaaatggc aaaatcaaca ataatccctt ggctatatgg tggtatttct      60
gttaaaagtg acttatgggt agattttta gcttcataga ttctttgtcg aaaaaaaatt     120
actttgtaca ttttagtgga gttatttaaa tttcccaatt gaacaaaacc atatattgat     180
gaaattcgca aatgcaatcc aaaaataaat atgttccact cttttggtta gcttttaact     240
aaacatgcgt tttnnnnnnn ttccagctag tacgagtctc tatatataaa ctttcttaat     300
atcgctaaca atttacttca agtttgtaat gtgataagtg aaagaccgta tatacataca     360
catgttaatc aactgataac ctttgtgcct cgtgtgtcta gttactagtc aaccatcaaa     420
cgtgcatgat gctgttttc ttagagtact attgttgtgt tatatataac taaacataaa     480
caatttgcta ttatgatata aacatagaat tttcaagcaa tgatatgttt agatgttttg     540
tataaatatt ccataaatag tagacaccca tatatacaca aacatgaatt ctacctgagg     600
```

```
agaaacacat agatgttcaa attaaataat aaccctataa tgaaaactct aaagtaagta    660
atacgaaata aaaatttatc ctttaaataa catataacat atatatcaac tttaattggt    720
aattgtatca caagagccaa ttatttggtg actgtatcac acgtgcttaa agagagcgtg    780
ggaatgaaag taagaagaa taagaagca gagagatggg ctagaaatga gaaaacacac     840
caaaccctaa cctcaccctc acacatttct tatcttttgc tctcaataga ttccattgat    900
tcaaaacaaa attttcatta agatttcaca acctccacac acttccaaac acaattaaag    960
agaggaaaaa gaatcaataa ccctataaat aaaaaatcag acaaacagaa gtttcctctt   1020
cttcttcctt aagctagtac cttttgttct tgaaattagg gttaatttct tttttccaaa   1080
taccatcaat tctccagacc ataaaaactc aaaaagatca gatctttcct ctgaaaaaga   1140
gatacccaac ttatgttttt gtgtgtctgt atatagataa acattacata cccatatttg   1200
tgtatagaca taaaaagtgg aaattaaggt aacaaaaaga atgggaagaa ggaagagtag   1260
agctgaagag gatagagaac aaaatcaaca gacaagtaac gtttgcaaag cgtaggaacg   1320
gtttgttgaa gaaagcttat gaattgtctg ttctctgtga tgctgaagtt gctctcatca   1380
tcttctccaa ccgtggaaag ctctatgagt tttgcagctc ctcaaagtaa acaactctct   1440
cactctttat cagtttcttg attgagtttt tgctagatct gagcttagat ctttgtctca   1500
aggacttgtt atatatagat cacacgatct tgatttctac gaagttgagt taattagatt   1560
tcttgatttc attttctagg gttttttttcc aattcttgaa atttaagatc tggttttttt   1620
gttgtcaatg atttagaact gtgaattttg taatcgaata gattccaaat cctgatatgc   1680
aatctgaaaa gttttatata attaatatat gtctgtgtga ttggaaactt aaaagttgga   1740
atcacagatt tctatgaaaa ttacaagtat ccaacgtaga attgataata tatggttaca   1800
tgcattaacc atttgttagt tcatcatact ttatggtggt taaaacttca aacgcgtgta   1860
tatctatgaa ggcaaagatt gtttgttttt tcttaaaaac aatgtttaat agattttttaa  1920
ttatatgtta aaatagtttt gcttacatgc attcaagaaa atatagcgat taattccttt   1980
tttcaaatca caatttgtga atcaaacgaa aacgtaagat attgcttgca aatgatagga   2040
ttgaactatt gatatttgta aatataaata cgaaacttta cgtttgaaag ttgaaacaat   2100
caaatccaaa tcaactcgta tataatcaga taaataatgg aaacaatctt caattttgat   2160
ggaagaatac tttaaaactt gaagagcttt ttttttttat ggtgatttat aggtttagat   2220
ctccaaagtc aagtatgatc ttttaataa actcttattc tctcttttg agttattttc    2280
agcatgctca agacacttga tcggtaccag aaatgcagct atggatccat tgaagtcaac   2340
aacaaacctg ccaaagaact tgaggtgttc ttaattcaaa tactattttg agttcctatc   2400
atatcatttc aagaaagatc tttttttttta aaagtttgtt ttcgtgaaat atttcagaac  2460
agctacagag aatatctgaa gcttaagggt agatatgaga accttcaacg tcaacagagg   2520
tacatatcta tctataccctc catatatta ctcaattctg tatccatgta gattcatatt   2580
tgtaggtgtg tgtggctttt gttggtgcag aaatcttctt ggggaggatt taggaccttt   2640
gaattcaaag gagttagagc agcttgagcg tcaactggac ggctctctca agcaagttcg   2700
gtccatcaag gtatctttat gcatggaatc aatgattcaa atgagattaa tttgtgttgt   2760
ttaattatac tactatggtg gtatgatgat tgtttgcaga cacagtacat gcttgaccag   2820
ctctcggatc ttcaaaataa agagcaaatg ttgcttgaaa ccaatagagc tttggcaatg   2880
aaggtataat tacagaataa atgcatttgg tgacttgcga tcaatctctt tcacagagtt   2940
taagtttcta aatatgtttt gaaacatctc tagttttctt gtttctgatt atagtctttt   3000
```

-continued

```
ggtgaaatgt aaatgtttag ctggatgata tgattggtgt gagaagtcat catatgggag    3060
gatgggaagg cggtgaacag aatgttacct acgcgcatca tcaagctcag tctcagggac    3120
tataccagcc tcttgaatgc aatccaactc tgcaaatggg gtaaatctgc cttgaaaaat    3180
catctgcaaa tcagtttgtg tacttaacta ctaagattgt ccttatttaa ggttctttag    3240
ttgcttggtg taaagaggat catcaatgtg tgtgaacctt ctaagttgat gttttggcga    3300
tgatgatgat gatgcaggta tgataatcca gtatgctctg agcaaatcac tgcgacaaca    3360
caagctcagg cgcagccggg aaacggttac attccaggat ggatgctctg agaatcatgt    3420
actgtgatga agctcaccca caaaagacct tatatatata taaagtatag atacaagact    3480
tggatttgta gacataagtg gctaatataa tggtcctgag gatcttctag acatttgtat    3540
cttttgggaa tccttgctta tattaagaat tcaaatgtgt ggaacttgtt ttaacactga    3600
accatgacac tggtttatta tcatgtaatg agagaaacat ttgggttaca atgtgatctc    3660
tccttgaccc aaatacacaa tataaaccct atgccaaaat acaagcatca catatatata    3720
ttcataaaag gtttaagtaa tcatacaaat gatgtaaaaa gtttcatgcc ttgaacaaaa    3780
cactgcgcca aaggcaaatg gtaagaaaca tgtcagattc ctgtgtgcat ctgttttgct    3840
gctgctgctg ttgttatctc tcaagagggt ttcctcagaa ctccataagc caaacgtgca    3900
gagagacgtt tcctcattcc cccatcgtat acaataccat atattgttaa aaaaagata    3960 tcacagatca aatcaatttg cacatctctc tgctgccttg tcaatctcct caggtccggt    4020
caaggcagat caagacagga tcaatggcaa caagttacgg tgtttcgttg aactccatca    4080
cctgcaaatg agacgaattc acagcagaga aaaaatatt ctttagtcaa catgaatgag    4140
aaataattca aatgttctga gtttcaggaa gaatgattag ccatatttgt actagacaag    4200
acaagtaaag attttacgca tgtgcttcta gggttgttgt acatctttca ttctattgat    4260
ctctggatca ctcgtctatt tatgcgtgat ggtgtctgag tctgactctg aaacactagt    4320
aaatgagaag ccgaaaactg gcttggaaga acatgaaaag tgtttaccct tccacaaaca    4380
gggcagtttt cacttctctc catccattca taaatgcaac taaggtggaa atggtgagaa    4440
cactttgtaa caatcttcgg gttctctgat atgtattcta caaaacacac gaaataatct    4500
gatactaagc tt                                                       4512
```

<210> SEQ ID NO 2
<211> LENGTH: 3589
<212> TYPE: DNA
<213> ORGANISM: Arabidopsis thaliana
<220> FEATURE:
<223> OTHER INFORMATION: AGL4 promoter
<220> FEATURE:
<221> NAME/KEY: modified_base
<222> LOCATION: (1532)..(1537)
<223> OTHER INFORMATION: n = a, g, c or t

<400> SEQUENCE: 2

```
tgatagcgct tcgttcatca tgcagaagaa accaatgttt ccccaatctc acgcgcctcc      60
tcctatctac caccacttgg acaaatcccc tttgcagtat tcgttttttt ttccggacat     120
tgtacattca aaagcattcc aagtgtctaa taaacataac taaccactcc aagatgcaaa     180
atctagctac gacgaacaaa ttttaaacta tagagatgaa ctttaaattc gggcattaat     240
tagtggaact tgagctattg atgatcgagt tttctgactt tttgaagctt aagcttaatt     300
gagttttata tacactatat aggcttgtaa taatatggat caaacaagaa aaatacaaac     360
tacaaattgg gaattgggtt ttaaaacgtt atcgttctat tttaattcag gcacgtacct     420
```

-continued

```
ttagaatatc aagatccatg tttcaatatt tctgttgaca aataaataaa gatgtctcaa    480
atataagttg ggcaacgtac gtgtagacct aaaagagtcg aaacattggt atctaagtta    540
tatatctaca tggattatat aacaagacaa cgtttgtttt aaaaacttca ttgattttc     600 ttaattagta gcaactagca actaactact catggcaaat aatggcgtct gcgtggcacg    660
cgacttggga gagaaggtgt gagaatgttt ttactttctg tgtaaaagat ggaagagaga    720
gaaagagtaa agaagtagag agagagatat tgtatcacca accctaatg atctctcacc     780 ctcacaaatt ttcttatctt tatagctttt atagattcac aaaaacttt cttcagattc      840 acaatctcat cacaacccttt caaaaagaga aagatctaa agaataaaca agagccctaa    900
tatcaaatca caaccaaaaa aaccaaagaa agctaattaa agttttctct ctagctattc    960 ctcttcttt cttgttcttg aaaactaggg tttacttcac caaaaagata agatctttcc      1020
ccagaaaaag caatacccaa gtcatgtttc tgtgtgtctg tatatagata aacattaca     1080 taccctaata aggttacaca aatagctata aagagggaa aataagatag ggatttttg      1140 gggtgaggaa agatgggaag aggaagagta gagctcaaga ggatagagaa caaaatcaac    1200
agacaagtga cgtttgctaa acgtagaaat ggtttcgtga aaaaagctta tgagctttct    1260
gttctctgcg atgctgaagt ctctctcatc gtcttctcca accgtggcaa gctctacgag    1320
ttctgcagca cctccaagta cttctctttc tttatacact tattagatct gtgtgtagat    1380 cttcattt ttcagtctt gtgatgagtt ttatctttct tgattgcttt ttaacaaaat        1440
acttgatata ttttcagttt cttaatctga ctctaattag gttttgatta ataggaagga    1500
aataaatcca ggtaccttc aaggtgaatt gnnnnnngag atctgatctt aatttaatca     1560
tcatgtcaaa ttcttaggga tttaattgca atctattttt agatttatcg gagctaggaa    1620
agtatcataa tgatatacta ttattatcat gtaatttcat tgtctctaca cggatatata    1680
tgtgattaga acttggtaaa gtaaactaaa gattcacagt cttcaatgaa attgaaaaga    1740
tccaacgtag aataattagt ggttccatgc attaaccagt ctaattaaag ctcatgcaga    1800
catttaagca ccacatgaat ttaatatctt tttaattaag ggatcttctt tttataaatt    1860
ttcttttgtt agcttttaaa attttagttt gttcattaaa atttatagat cctcctctcc    1920
tgatttgtgt tttccgatcc tttccagcat gctcaagaca ctggaaaggt atcagaagtg    1980
tagctatggc tccattgaag tcaacaacaa acctgctaaa cagcttgagg tttaatctcc    2040
aacatctctt cgatcttaat tatttatcct tttttaattt tatctaaaga aaatgtttga    2100
ttttgagaca aaagcccttc aaagtttctt acatagatat tcaattgtct attatcttcg    2160
caattttcag aacagctaca gagagtactt gaagctgaaa ggtagatatg aaaatctgca    2220
acgtcagcag aggtatatac attaatgtgg atgatgatca tttataaaca gcatatatat    2280
atatatatat atatatatat atatagaaag tattgatcat gaaagtgtgt tgcagcagaa    2340
atcttcttgg agaggatctt ggacctctga attcaaagga gctagagcag cttgagcgtc    2400
aactagacgg ctctctgaag caagttcgct gcatcaaggt gatttacttc tgtacataca    2460
ctgaaagatt cacacaaatc tttctctata tatagactga gacacatgca tgaaatgttt    2520
ttgatgcgtg aggttatctg aaaatgcctc ttctttttg cagacacagt atatgcttga     2580
ccagctctct gatcttcaag gtaaggagca tatcttgctt gatgccaaca gagctttgtc    2640
aatgaaggta tatgatgatg tttctctctc tctcctccag tttctattta tagatggaaa    2700
ctttaaatag tccaatttat atatatgagt ctaaatttca cattcttcaa ctgctacatg    2760
tttcttttgt attatttcta tgatatcttc aggaaagttt gaaaaatatt gtgttttgtt    2820
```

-continued

| | |
|---|---|
| tagctggaag atatgatcgg cgtgagacat caccatatag gaggaggatg ggaaggtggt | 2880 |
| gatcaacaga atattgccta tggacatcct caggctcatt ctcagggact ataccaatct | 2940 |
| cttgaatgtg atcccacttt gcaaattggg taaatcaaac aacttttctt gctttaagac | 3000 |
| atcaacttag gttataaaca gttagcagtt tgctttaagc ccaacattgt ctttgtttca | 3060 |
| tagaggcttt ggttaaaact cgtgttgttt agtctaagga ttcagcactt tgatgtctga | 3120 |
| agtatggaaa atcaatctct cagacttgaa aatgtgggtt tctattgttg acttcgaaac | 3180 |
| tatgttgttg tggtgttgca aacagatata gccatccagt gtgctcagag caaatggctg | 3240 |
| tgacggtgca aggtcagtcc caacaaggaa acggctacac ccctggctgg atgctgtgag | 3300 |
| cgatacttct tcccccaata aagatcttaa gcaagtactg gtggggtctt cgtggtgtga | 3360 |
| tcttagatct tatgcatatg aataataatg ttattgcaca agacttttgc ttttgtagac | 3420 |
| acaagtggct atagctgtaa tagccttcaa catctctctt ctgtttcagg atttgtttgt | 3480 |
| gcctattgta attgcttata tatgtatggt ttgtataatg tgtgaaatgt taacatcgac | 3540 |
| catgtctcat ctggtgaaga tcttatcctg tctatgcatg ataccaaaa | 3589 |

<210> SEQ ID NO 3
<211> LENGTH: 14940
<212> TYPE: DNA
<213> ORGANISM: Arabidopsis thaliana
<220> FEATURE:
<223> OTHER INFORMATION: AGL9 promoter

<400> SEQUENCE: 3

| | |
|---|---|
| taaaatctgg aagtttccag ccctgataat gttgcagaat aaattagtgc gcagtaagtc | 60 |
| tccaaaaaga gagaaactac aaataaataa accaagtcaa attcattaac aaggagaaca | 120 |
| gcatgaaatg tttcccaaac acacaaaatc ttgactagcc aacagcgctt caaatgagga | 180 |
| agtaactaat ttcagtagct tgggtatggt gaagtataat taccttccac cacacatatc | 240 |
| cgtagcctat caccccaacg ataatgatca aaccatagtt tctaccacct gtacattgaa | 300 |
| ggaaagtgtt aactgttttc ttccgaattt agatcaacag taaacaaaga atggtgttac | 360 |
| tctaagtctc taatgtaatg ccttcctaaa tgctacaaag aaaagccact tatcagaaca | 420 |
| aagtatgtct tgtttgatgc gagaaaagta gcaaagaga ataaaacctg aaatataatt | 480 |
| tcaaaataca atgtctagaa atctaagtgt gcaaatcctt tattcaagtt tcatatcaaa | 540 |
| ccaatttga catttctagt gcagaacaga aaacaaaact tcaatataaa aaaatataaa | 600 |
| aactccagag gacctgatcc tgaaggtgaa acaatggtga taggtctgtt tgaccccagc | 660 |
| aactgtatct catgcctaag actgttaacc tacaaaaata aatagagctc aggcaagaaa | 720 |
| ctattgattc acgataaatc tatgtcctca gcaagtctat attatccagc tccatccgat | 780 |
| agcttatcat cgccaataga ttaatgtgaa acttacctgg gccacaagta catcatcgtg | 840 |
| gggtttgcta gctgatttgc taggttcgtc ttgtttcagt tgcctgaata ccatctgtcc | 900 |
| acataaacaa aacccattgc ctcatttttgc caaccgcat catacacatg tgaagtcgcc | 960 |
| aaagctttg cacaatatag aaattagaat accttaaaag caccagaaac caaattggag | 1020 |
| acatctggta agcccccttc tttagaaaat gctgatccaa taagacctta agtaacatt | 1080 |
| tgcaaaaatc acagtatagt tagtaattgc agtaacttgg acgaacatta agcatgtaca | 1140 |
| cgaaatcaat cgactcagca agttcacaat aattgtacta gtaggtgcat tcacagagaa | 1200 |
| actaaacata aacttctcct cagatgtatt cagagaatag ctatactcca ataaagtctt | 1260 |
| aaactttgag ccagtcaagt acactgatca aagggtttat gaaaaacact aacttcttat | 1320 |

```
cctctaattg cgattaccca tagacgaaac caataaaaaa gcaatggaga actagagcac   1380
agtcactaca agaaataccc tataaaagta ccgacctgca ccgatgagga tggtgagctt   1440
cccgagcgga agagccatgg ctagagacga gcttatacgg cgaagaacta agatggcaaa   1500
cgaatccgcg tgagaatatc taagagagta ttggtaagag agagctgcag gaacgtaccg   1560
gtgaaacaga ggcgttttt gggacgatga agtgaggcag cgagagagat acgacgtgcg    1620
actatattgt tcgcttgttg aggcaacaaa acagagttgc ttctaaaacc cgaaccgaaa   1680
tgtccggtct gattcggtct aaatcacgat taggttcgtt ttaaaaccta ggaggcaata   1740 accgacgga tcataaattc ataatagaga cagacaaatt ggtccattat taaaatcact   1800
tgggcatttg gggatgattc aaatgcccaa gttttctcaa atttggacga ttcattcacc   1860
taagacatac ttgagcaaca acaaagtgaa gtccactgtc atatcttatg tctcaaaaag   1920
tattgaaatg tgtcaattga tattggagag gcacactagc taagggatta ttcaatcaat   1980
ttccagcaat ttaattaaac ttatttgtag tgaaagtggg aagataaaag atctcaccct   2040
cacatgttca aaaaaaaag ttgaaaatgg aagtaattca acatgtagca tagagcccaa    2100
atatgtctca ttttttaat ccatataatc tcaaatcctc ttacttactt ctaaacatat    2160
ggttcccata atcataacaa tgctatgtta acatggccgg ttctaaagga agccaagtgc   2220
agcaactgcc ttacgcctct acgtgttaaa atgaaaatga agaccactga ccacttctat   2280
taaagcttca ttcactagtg tataattaca cattttttta aggatttatg agtagtgatt   2340
gaggcccata tgtttgtatg tttgtttttc ttactatatc attacttgac tataagagtt   2400
ggtttcctat tccattctct tttctaacag cctatatatg taaaaatcta agcaaaattt   2460
cttgtcaaga ggatgattgt acatttgtac ttggttatct cgccccggcc caaaacatac   2520
ctaaggccag gtgctatatc ctcaacctgc tttggcattc atcaatctac gaactttggc   2580
gtgaaacggt gacaagatta acaagattca ctctcaacta cgatgttcta ctatctcaaa   2640
tctttaaaaa agtggatcaa actgtcaaaa gtctagttcg atggactagc ttcaacactc   2700
ctccaaatct agttcgatgg actatatatt ctcttctgat gctatcctta tcttggatta   2760
ggcatctaaa ctatggtttt aatggtgtca tgaggtttta caacttacaa ggatgaaagt   2820
tatttactcc cagtcactat cttaatcaaa tgacaaaatg ttaactagtt tgagtgctta   2880
tatattagtt atgaatctga aatttattag tgtgtacata agtgatacaa cacttaaata   2940
acatctacat gagttttaa ataacataat aatccattat agtagtttac ggcataaggt    3000
atgaaccaaa tttttcattg cacgctgaaa agtgaaaacc tttaaaatgc ataatgacta   3060
agagtctatg acaacagtaa cttactatat attagaggag gggtgaaaaa aaaagtagag   3120
agactggtcc aaaaacttaa ccccactcaa taaacccaga cgtgacttgt ttgacgataa   3180
ctccatcttt ctattttggg taacgaggtc cccttcccat tacgtcttga cgtggaccct   3240
gtccgtctat tttagcaga ttaatccaac ggttcttatt cttcttcga cccttcacga    3300 cattgcctca aagccgtccg attctcatct cacgcccaat ggaccacata tatcaccagt   3360
actccgcaac ttagctgtcg tgtaggattt cacgtggcat ttatttgttc tagttttgtag  3420 tgcaaacatt gcaagttgat atggtcccct atcgatcacc gtcgtctctt tagcttcaca   3480
tcgagattct tctttcttc ctacgtgtaa tagcattttt gattttgaga attctttag      3540 aaccgttgga tctctcatcg ttggttgatc catccatcca aatgggacct gtgtgtgctc   3600
catccagggc atatgatccc aaagccaaaa gagtatttcc aagtgctttc tttctttctt   3660
tctttctttc ttactaacct tttttttct tatgctttag actaagaaat ttattcggcc    3720
```

```
atatccactt ttacgaatat acttcttaca agatctagat tttttgagt taattcggtg    3780 tatataacat tggcatggac tgcaattaag taatggtaat gtgatcatga tgcgatgtgt    3840
cgttatcagt agtataatat tgatgggcta ccctggaaaa caaaattacg tgttatatgt    3900
acacaatttg gtagaaccgt agaaattaaa ctgaataaaa ccttctataa tgttcaaaat    3960
tatatggtac agattaatac ggaaaaacat tcacgcttta cgtaacaatt aagtggaaag    4020
taaaattatc ccaaaaatat ttatatcaca tcattgttat atttctaagt ttttttatat    4080
ctctaatggt atatgtttta cagattgttt tttgggaaaa ttcttaaaga gacttgaaga    4140 atgtttttt tttattttct tgaaatgttt gacacttgaa accgtttaaa aactcaaata    4200
tagtatatat cattgttggt ctcataccct gtaattcacc acatatatta tcaatgggga    4260
agatttgaaa atttttgggg gatcacaaaa cgaaggaaag agtacaaaaa gagaaggaaa    4320
agatagaaga tatatgtttt taacttcatt ggtatgacat caataaataa atagttgaat    4380
gtactttagt ttctcttttg gtttaatgca catcatctcg atcaattgtc atcatcttac    4440
attgaattat acgaccagat ctgataacaa gtgaattcgt acttgcccctt ccctttcttc    4500 tcatacgtcc ttctaactaa ttttgattgt aacttataat tatataacca tatttaattt    4560
tattttatct aaaaccaatt gaagcaaatt aaaatatcat aaatcttgag tcccacatga    4620
agacaatata taaaactcgt gcaaatttgc ttaaaatgct tctatgagac catgaccaag    4680
tgagattaat aagcgattca atgtgcaaat caaaagagaa aagaagctaa tgggtttaaa    4740
tataaccaaa cagaataata atgctatgtt tagttttctc aattgaatca tacctttgtg    4800
tccatcacct acttaccggt cagaataaag caattacgtc tgcaaccaaa aagcactaag    4860
actttcggtc agacatgatc tctaacatcg gacgaaccct aagataacca aaataaaacta    4920 tatcttatat tcaaatctct gtttatttta tccatttatg ttttctttct ttcccataat    4980 ttttttgtg tctcatcaga ctctcttacc aaactgaatt tatcaacatg gtttttttt    5040 tggccacatc aaaatggtgg tttataaagt agactaatac aaaagacatt tctgttaatt    5100
tcactaacaa aaataatctt agcagtacta tagattggaa aaggaaaagc aaatctagca    5160
gtaagattta tcaaaactag cagtaagagt tttagatatc atgaaaacat cacaaacgag    5220
tagtgtttta ctttacattt ttaaccaatc acaagggtag ttccgtaagt tgggaaaatc    5280
gtacgaggct tcacctagtt aaggttaggt cacatgattc cctgaactcg attttataag    5340 taaaaagaa aaatttataa aatcaaaatt tttatataa aaaatcagg tggatttatc       5400 agaccctacc atcgagatgt cgacacgtgt ccaaactcat tcattgccct actatttct    5460 gtttagggtt gcaatcactc atcgcacacg cgccatctcc accttccatt attaatctct    5520 catttcaac atcacactct tacgaatcat acgattttaa tatctctgtc tctctcaacg    5580
tattaaataa aaatggtttt aaatgttagg gttttttgta ggattttcaa ttattaatct    5640
ctataattcg atgaactaag taaaaaagca tcaaactttc ttggcagaat cacattttc    5700 tctaaactaa atatggactg aaattgaaaa attaaccac tagctagaat aaagtgttgg    5760
tgagagtgga actctaattt ctctcctta ctaattatgt ataaacacaa aaatgcacca    5820 aattttagg tttgaaaata tctaagcatg gatagggtaa ttaacatttt ttctttcaat    5880
tttgcaatat ttgaataaat cctatgaggg tctttggtac acaataattg gagggtatat    5940
agttgagtct gagagtatat tagaaagaga atatttcaag taatgaagct gacatgttta    6000
tatgtacttt gagagaagtg ttgtgagatt tgtacaaatg tatatgtaca ctttaaaaag    6060
caatataaga tagataaaaa aaatataaag aaaaaaagaa agaaagaaag aaagaaagag    6120
```

```
agaggctcat atatatatag aattgcttgc aaggaaagag agagagagag attgagatat   6180
cttttgggag aggagaaaga aaaagaaaat gggaagaggg agagtagaat tgaagaggat   6240
agagaacaag atcaataggc aagtgacgtt tgcaaagaga aggaatggtc ttttgaagaa   6300
agcatacgag ctttcagttc tatgtgatgc agaagttgct ctcatcatct tctcaaatag   6360
aggaaagctg tacgagtttt gcagtagttc gaggtatata tctacttttg tatatatatt   6420
acttataaca taaacatttt atatacatat taagtaacac aaaaatgtct tgtatgtatg   6480
ggtctctctg tgatgtgttg ttgtgtcgta cgtacgtgtt ctatcatatc cttttaaaag   6540
aagcaaagag gaaaaaaaat ttgggatacc ccaaatctgt atcattttat aacaagtttg   6600
cttttttgat gttcttttgt gtttctcttt gatttccatt tttgttttg attttttttc    6660
tatttctctt tacatctatc aaagttttt ttcttatatt ttattgctta tttgtttgtc    6720
tacttaattc acattatctg agagaagaac aatctatctg atatgaaatt agggttaatt   6780
tctcttgtga gtactcttta attcacataa gcttaaagtt tccacctttt gattctgggg   6840
gtcgtccaat tcgatcaaat cactcaattt tgttgtcaga ttgatataag ttcataggg    6900
gatattgttc ccacgacaat ccatttagt aaccttagg ggtttccaat tttgggtttt      6960
gaattgacgc taatgtcaaa ttcatctaaa gtccgttgga tatgtatact tggggatggg   7020
attcatcctt ttttctgggt tctttagatc ttctcttaaa agactaacag attttgttgt   7080
aaaccctagg aaacagttaa aaatcccatt tttaaaaaca tgttttgaac ttgatgagta   7140
agattaatgg aagaaatgat gttttgtgt ggtgtgaagc atgcttcgga cactggagag    7200
gtaccaaaag tgtaactatg gagcaccaga acccaatgtg ccttcaagag aggccttagc   7260
agttgtaccc aattctcttc tcttttcttct aattacctta attaattact ctcaattttt  7320
actttgattt ttagagtcaa atgattaatg ttataatttg tcatatactt caggaactta   7380
gtagccagca ggagtatctc aagcttaagg agcgttatga cgccttacag agaacccaaa   7440
ggtaaactaa ttagcttctt cagctacctt cagagagtgt ttgttttttt agtagatttt   7500
tttgatggtt ttgatgttga aataggaatc tgttgggaga agatcttgga cctctaagta   7560
caaaggagct tgagtcactt gagagacagc ttgattcttc cttgaagcag atcagagctc   7620
tcagggtact actttgttca tcaatatctt tatacactga tctatttcca tagtaagatt   7680
aaatttggtg tttaattctg cagacacagt ttatgcttga ccagctcaac gatcttcaga   7740
gtaaggtaaa taagaaaaca ctcattctcc tctctaaatt cctcatctaa aagtaatgta   7800
accaagaaaa cacaaatatt tggagcagga acgcatgctg actgagacaa ataaaactct   7860
aagactaagg gtaattaata tacattctca tatcaccaaa ttaatgcatc actaaatttg   7920
gttataatgt gtgtgtgtat atacatatgt gacagttagc tgatgggtat cagatgccac   7980
tccagctgaa ccctaaccaa gaagaggttg atcactacgg tcgtcatcat catcaacaac   8040
aacaacactc ccaagctttc ttccagcctt tggaatgtga acccattctt cagatcgggt   8100
aactttagac tagtataacc aatttgattt gagttctatt ataagctttt cttaagaaag   8160
tatctcaaac tactaaattt tatggagcag gtatcagggg caacaagatg gaatgggagc   8220
aggaccaagt gtgaataatt acatgttggg ttggttacct tatgacacca actctatttg   8280
aatctttctc acttaatcaa tccctctctt ttttttttga cattttttaag atgatgtttc   8340
tattttatta cctctctcat gttttctgtc ttgtgtgcat gtgtgtgtgt aatgtttatg   8400
cccttctatt attcaataat ttttcgaca attttgcttc ctattttac ccattactcc     8460
taaacttcct gatccagttt cttttaaaat aactcccatt ttatgcatgt tatctaacca   8520
```

```
attctcttaa ctatgattta tggtacgata taactcacag tctcacacta tctatttggt   8580
gttttttgt ttgagtcttg agaagggacc gcttgtttat ctctcttgtt aaagagcaac    8640
tcactggcca ctgcttatgt atctgtaggc cccacctata tcattttggc tatatctata   8700
cttttgtaga gggagtatta ctatagagaa gaagataaat ttggttctaa tatatcttgc   8760
aggtagttga tattctcaat tatcatgaag atttgataga caagtttatc agataccttta  8820
aacataggtt taagatctca attgaaatgt gaattcaccc gacgattaga gttacgatct   8880
aaggaagcgt ttcttgaatt ttgagtttgt ttgatcaaga gtagaatgct tttctattac   8940
taaggttgtt aatgcttata ttccatgacc aaggccaaga gaacaaacaa aaacatggtg   9000
cctcttgatg tatagtaatg gctcttaatg gtcatataca gagaaaaaaa gattaatgtc   9060
gttgcacaag cttgaagtta cttactcctc gtcttcctca ttagtgtctt cgtcttcctc   9120
atcctcatcg ctcccaatat agggcttcat ctacttgaaa accaaatgct catgcagtgg   9180
aaaaagataa cagaggttca aattaaggca aacaaaacta caagtgagaa agggaaacta   9240
caagtggtaa gatgtaatgt tttgactcaa aaccagatca gacaatgaaa aaaagtattg   9300
atacaaaaag tccatccgga agcataatta ccgcttgcag gatgtcatca gagatgtctg   9360
ttagtcggcc aatggcatag atggtgagcg gaccagagta gcgtaaatcc tctaaatact   9420
gtctaaaagc cggaccgacc cgacaaggat cacagtcaag gggaatagga cacctattga   9480
tatcccaaaa gactgttgtt acagccacat catccttgtc caactgggta gcccaagggg   9540
aaactagttg tggtaagagc ttgtttgact caaaaaatgg ctaactagga tgatgctgaa   9600
ttaccatctg ttcatgtttt tgactagaga gatgggtagt gaaattttca aagcctttgc   9660
aaaacgcctg tgggacctgt ttcagaaaaa gacttaaaag acttgagact caaggaaaat   9720
aatatccatt atataaagat gacaacaaat attaacggaa gtaggagtga ttgagaacga   9780
ttctagtaga agagacggct cgcaggacgt cgtttataat aggccaatgg cagagatagt   9840
gagaggaccg gagtagccta aattctttaa atgtcgtttg atacacggac caactagacg   9900
agcatcatac tcagagggaa ccggacacgt cttgatatcc cagaagaccg atgttacggc   9960
cttagcttgc tgccgcgttg ccttcatcat catcttctcc ttttaatcta taacggaaat  10020
caaacatcag ataaagcatt cgaaaagata gattgacaca ggttaaatca tccacttcag  10080
agaaaaagag agggacatgg ccgtaaacaa tgagataagg atcggcctaa tgtttataat  10140
gggcttgcgt ttaatgggcc tacagtttct tgaatcagcc ttatgcatga gtcctagtat  10200
tttatcaact tttttttttc atctttcttt agttacaata gatttaaagt gttttttgtt  10260
aatgccattg caaaatttgg taactgttta taacattgtt cctcacttca aaatttaaag  10320
caccattaat aaaagctata catataatta taacttgggt tttgtgcaaa aaaaacaaac  10380
aaattaaccct ttcattttaa ataaatgcaa ttcaataccg caatatcaaa agtaacccgt  10440
ataacccttta ttcgtgtata gattttagaa acagtataag tcaaattatc aaaactatgt  10500
tgttttaagc attttaaaaa taagaataat aataatgttg aagggtggat ttgaacccat  10560
gaactataga acaaaccaaa gcatgcataa ccacatgcgc cgaacaaacc aaaaactcat  10620
ggctttgtta aacatataaa aatattcgaa taaaaaatgt ggggaacttg ttaccagttt  10680
tggttctttt tggagccatt ttttttcaaca cagatattgt taaggagttt caggtaaaac  10740
tgtatattat gcagggaacc acagtaggct ataatgaaag tcacactgtg aagttagcag  10800
acaagttttt acttaaagat gtgagttgtg atcttttttga tgtaagtctt gatgtatatg  10860
ttgacaaatt atataagttt gtattgcata ttctatgact tacgaagttt ctatgcaaga  10920
```

```
aaagccggga gaaaatttcc gtcaagtaac taagagatcg taattcttgt ctgaagaaca    10980
acccttttt attatttgag tttaggttgc caacagtgaa caaagggacg agataccata     11040
tgacaaatat cctctaacgc catttcaaca gttaatcaac agtgtcggct atatgcatgt    11100
gctaacaatg cacaagaaca ttgtcaccat cccgtgaata tgaatattaa tgattatgaa    11160
cgagtttgta gagttccaag aggaaggtac taccttctca tactcattga tcatatattt    11220
tgtttcttgt ttgttttagt aactagggtt attcggattg tttttcaaaa taatagtaat    11280
atgtcaacta tatttataaa aaaaaaaact aaataacttt tgtacaattg atcatttttt    11340
aaatatatca taaagattca tcaatatatg aacatatatt tttaacaatt acactaattg    11400
gctatatagt gtatagttcc ttttgtggag aggtttaagt tcagttcaga gattattgta    11460
cttggtaaaa tatttgtcct tgttaattag ttcatcttct agaatacaga tttgggccat    11520
gtagtttccc agaaaacacc ggaaaaaaaa ttcacacttc accagaaaa caataaacga    11580
ggaacagagc ccaaactcat ccctataatt gggcccaaaa aaagcagagc aaaccaaacc    11640
aaaatcaagt aaatccattt acaaatatgc tttataatta ttatttttct caaccacaaa    11700
tatgctttat aatttatgta aatgttatat gaattattta cgatttattt taattacttt    11760
atcttggaat tatcttacga agttaatgaa aatattttaa atatctaatt tatatatgtc    11820
tggactaaaa taaatagaaa tatctgtatt ccaatcatca caaaaaaaaa attctcatca    11880
tctttgatat atagaaagtt tttaaaattt cagtttcaca gattttacca attatagttt    11940
tataagctta tgctaattat gtgatcaatg caaacaaaag ttgacaataa taaaatgaag    12000
tcaaatatga tagattccta ctataaatat agactcgtga ataatactcg aatcagtctc    12060
tgaggttttg ctggaaaaga aaaccgaag agctcaaaac agagtgcgtt tgtttctggg     12120
aatcttcaag cctctcactt gcgaagacga agcttactcg taaggtgatt atcttcttct    12180
tcttcttctt ttcaattcct ttttcgttca tctgaaatgt gaaatcatgt gacgtgacga    12240
ttaggttaac gatcgaattt cttaatttcg tatatgatta tcttctagtt tcttgatcag    12300
cacatcttgt tgttttcttt caatcgagac tgattctaga tgttcttaag gatcttgttc    12360
gatgaacttt gcatgaatca tccatatcga cgaactggtc tgatcttctt gttgttatgg    12420
attaagtttc ttgagataca agaaaggctt caatgatcaa tctgatctgt tttgatgaac    12480
acaaatcttt atctttgaac catggataag gtcaatttca caccatggct ggaggaagtt    12540
tatcaccggc gtcatctttg gaagatgtaa aggcatacgt caatgctgtg gaggtcgcat    12600
tgcaggaaat ggaacctgca agatttggaa tgtttgtaag actctttcgt ggttttacag    12660
ctcctaggtg tgtttggttt gctcttaaac agtctaaaga acaatgacac atgtgagaat    12720
tgattctgat gttattttc tctttgtagg atcggtatgc ctactttcag tgcacgcatg     12780
caggacctct tgaaagatca cccgagtctg tgtcttggtt taaatgtctt acttccacct    12840
gagtatcagt taaccatacc tcccgaggct agcgaagagt tcataaggt ggttggaaga     12900
agcgtaccag taccaccaaa ggtggttgga agaagtctac cacgtccgga gcctaccata    12960
gatgatgcga cttcatacct tattgctgtg aaggaagcct ttcatgatga acctgcaaaa    13020
tatgggaaa tgcttaagct cttgaaagat tttaaagctc gcaggtatgt attagttctt     13080
ttctccatgt tatgtttgat ttttcagtc tacagaacaa acacattatg tgaattgatt     13140
ctgatgttac taagtctctt tgtagagtcg atgccgcttg tgtcattgct agggtggagg    13200
aactcatgaa agatcacttg aatctgcttt ttggttctg tgtcttcctt tcagctacaa     13260
cgagttttac cacgaagctt aaggtataga gtgcttatag ttaccatttg atgtttccta    13320
```

-continued

| | |
|---|---|
| tatgttaact tgtggtttaa gtaacaaaat tgtccatgtg caggcaaggt ttcagggcga | 13380 |
| tggtagtcaa gtagttgact cagttcttca gataatgaga atgtacggtg agggaaacaa | 13440 |
| gtccaaacat gatgcgtatc aggaggtagg cttcttggta ggatactttg tgttgtgtgt | 13500 |
| tgcactttct tagttctttg gtttgatttg ctttgttatc ttttgcaggt cgttgcactt | 13560 |
| gttcagggtc atgacgattt agtcatggag ctttcacaaa ttttgactga tccacctact | 13620 |
| ggagtctaga gatagccaga tagctaagga gagtactgga agactgtaat ataccataag | 13680 |
| agacgaaaaa gaaagtagag cttctcacga aaagagagtg tttttagttt tcttttgcaa | 13740 |
| acattagagt tttgtttgat taacatgaca ttcaaaaata tgctatgctt ctatgttgag | 13800 |
| gtgtacaatg aattggtgta taagagacta aaagagagtg tatagtttct tgttgaggt | 13860 |
| ttctttatg ttgaggtgtt caatatgcta ttttcagggt aatctttta taagaaactg | 13920 |
| agaagggaaa cactcaaaaa acagagttca acgtagaaac aaaaacagag aggtgaactc | 13980 |
| atgaaagatc aatttaacct gcttgtgatg attggcttat caagagaatt gaagagattc | 14040 |
| acgattacac aaattcaatt cttaaagaca agagtagact gctaattctt attaaggctg | 14100 |
| ttaatgcttc ttgagagcat tgaccttttc cctgaggtaa taaagcttgg ctcttcttac | 14160 |
| tttcttcttg tccaccacct taatcaccct caggtttggg gaatacctgt caccaaaaca | 14220 |
| cctccactta catcagtatt ttccatgacc aaggcaaaca aagagaacat acaaaacatg | 14280 |
| gtggctcttg attataataa tggctcttaa tggtcatata caaaagtctg agagaaaaag | 14340 |
| attaaagtgg ctgcacaagc ttgaagcttg aagttactta caaggggaac atggattcga | 14400 |
| cgcccactcc agcaacaagc cttctaattc taaatgttga gttgagacca gcattacgcc | 14460 |
| ttgctatgac gacgcctttt acgattgata cacgcctctt gttctcaggc acttcctgtt | 14520 |
| caaacaaagt aaatgaaagg tttcacttag aagatgaaag atagtttgat cttactcacc | 14580 |
| caagaaaaag aaattacaac ctaggccaac agtagttacc acttttagct gcacaatgta | 14640 |
| accaggcttt atctctggaa tctctctaag agttctcact tcctcaactg cttccttgtc | 14700 |
| tacaatctgc agaggattgt gacatcggtg cttccttgtc tacatgatat atctaaatac | 14760 |
| aagtgtcaag ttcgagttgt agtacctgca taatatgctt agcggtttta tcaagccgct | 14820 |
| taaacttgat tctctgaggc acaacacaat ctgactcagg ggatccttga acagaatctc | 14880 |
| cagtggtgga aaaacacctc gacgaaaagt tttgtttctg ccaaaaaaat attcccaaga | 14940 |

<210> SEQ ID NO 4
<211> LENGTH: 1294
<212> TYPE: DNA
<213> ORGANISM: Arabidopsis thaliana
<220> FEATURE:
<223> OTHER INFORMATION: AGL2 cDNA
<220> FEATURE:
<221> NAME/KEY: CDS
<222> LOCATION: (387)..(1133)
<223> OTHER INFORMATION: AGAMOUS-LIKE 2 (AGL2)

<400> SEQUENCE: 4

| | |
|---|---|
| ccctcacaca ttcttatct tttgctctca atagattcca ttgattcaaa acaaaatttt | 60 |
| cattaagatt tcacaacctc cacacacttc caaacacaat taagagagg aaaaagaatc | 120 |
| aataaccta taaataaaaa atcagacaaa cagaagtttc ctcttcttct tccttaagct | 180 |
| agtaccttt gttcttgaaa ttagggttaa tttcttttt ccaaatacca tcaattctcc | 240 |
| agaccataaa aactcaaaaa gatcagatct ttcctctgaa aaagagatac ccaacttatg | 300 |
| tttttgtgtg tctgtatata gataaacatt acataccat atttgtgtat agacataaaa | 360 |

```
agtggaaatt aaggtaacaa aaagaa atg gga aga gga aga gta gag ctg aag      413
                              Met Gly Arg Gly Arg Val Glu Leu Lys
                                1               5 agg ata gag aac aaa atc aac aga caa gta acg ttt gca aag cgt agg       461
Arg Ile Glu Asn Lys Ile Asn Arg Gln Val Thr Phe Ala Lys Arg Arg
 10              15                  20                  25 aac ggt ttg ttg aag aaa gct tat gaa ttg tct gtt ctc tgt gat gct       509
Asn Gly Leu Leu Lys Lys Ala Tyr Glu Leu Ser Val Leu Cys Asp Ala
                 30                  35                  40 gaa gtt gct ctc atc atc ttc tcc aac cgt gga aag ctc tat gag ttt       557
Glu Val Ala Leu Ile Ile Phe Ser Asn Arg Gly Lys Leu Tyr Glu Phe
             45                  50                  55 tgc agc tcc tca aac atg ctc aag aca ctt gat cgg tac cag aaa tgc       605
Cys Ser Ser Ser Asn Met Leu Lys Thr Leu Asp Arg Tyr Gln Lys Cys
         60                  65                  70 agc tat gga tcc att gaa gtc aac aac aaa cct gcc aaa gaa ctt gag       653
Ser Tyr Gly Ser Ile Glu Val Asn Asn Lys Pro Ala Lys Glu Leu Glu
     75                  80                  85 aac agc tac aga gaa tat ctg aag ctt aag ggt aga tat gag aac ctt       701
Asn Ser Tyr Arg Glu Tyr Leu Lys Leu Lys Gly Arg Tyr Glu Asn Leu
 90                  95                 100                 105 caa cgt caa cag aga aat ctt ctt ggg gag gat tta gga cct ttg aat       749
Gln Arg Gln Gln Arg Asn Leu Leu Gly Glu Asp Leu Gly Pro Leu Asn
                110                 115                 120 tca aag gag tta gag cag ctt gag cgt caa ctg gac ggc tct ctc aag       797
Ser Lys Glu Leu Glu Gln Leu Glu Arg Gln Leu Asp Gly Ser Leu Lys
            125                 130                 135 caa gtt cgg tcc atc aag aca cag tac atg ctt gac cag ctc tcg gat       845
Gln Val Arg Ser Ile Lys Thr Gln Tyr Met Leu Asp Gln Leu Ser Asp
        140                 145                 150 ctt caa aat aaa gag caa atg ttg ctt gaa acc aat aga gct ttg gca       893
Leu Gln Asn Lys Glu Gln Met Leu Leu Glu Thr Asn Arg Ala Leu Ala
    155                 160                 165 atg aag ctg gat gat atg att ggt gtg aga agt cat cat atg gga gga      941
Met Lys Leu Asp Asp Met Ile Gly Val Arg Ser His His Met Gly Gly
170                 175                 180                 185 tgg gaa ggc ggt gaa cag aat gtt acc tac gcg cat cat caa gct cag      989
Trp Glu Gly Gly Glu Gln Asn Val Thr Tyr Ala His His Gln Ala Gln
                190                 195                 200 tct cag gga cta tac cag cct ctt gaa tgc aat cca act ctg caa atg     1037
Ser Gln Gly Leu Tyr Gln Pro Leu Glu Cys Asn Pro Thr Leu Gln Met
            205                 210                 215 ggg tat gat aat cca gta tgc tct gag caa atc act gcg aca aca caa     1085
Gly Tyr Asp Asn Pro Val Cys Ser Glu Gln Ile Thr Ala Thr Thr Gln
        220                 225                 230 gct cag gcg cag ccg gga aac ggt tac att cca gga tgg atg ctc tga     1133
Ala Gln Ala Gln Pro Gly Asn Gly Tyr Ile Pro Gly Trp Met Leu
    235                 240                 245 gaatcatgta ctgtgatgaa gctcacccac aaaagacctt atatatatat aaagtataga    1193
tacaagactt ggatttgtag acataagtgg ctaatataat ggtcctgagg atcttctaga    1253
catttgtatc ttttgggaat ccttgcttat attaagaatt c                        1294

<210> SEQ ID NO 5
<211> LENGTH: 248
<212> TYPE: PRT
<213> ORGANISM: Arabidopsis thaliana
<220> FEATURE:
<223> OTHER INFORMATION: AGAMOUS-LIKE 2 (AGL2)
```

<400> SEQUENCE: 5

```
Met Gly Arg Gly Arg Val Glu Leu Lys Arg Ile Glu Asn Lys Ile Asn
 1               5                  10                  15

Arg Gln Val Thr Phe Ala Lys Arg Arg Asn Gly Leu Leu Lys Lys Ala
             20                  25                  30

Tyr Glu Leu Ser Val Leu Cys Asp Ala Glu Val Ala Leu Ile Ile Phe
         35                  40                  45

Ser Asn Arg Gly Lys Leu Tyr Glu Phe Cys Ser Ser Ser Asn Met Leu
     50                  55                  60

Lys Thr Leu Asp Arg Tyr Gln Lys Cys Ser Tyr Gly Ser Ile Glu Val
 65                  70                  75                  80

Asn Asn Lys Pro Ala Lys Glu Leu Glu Asn Ser Tyr Arg Glu Tyr Leu
                 85                  90                  95

Lys Leu Lys Gly Arg Tyr Glu Asn Leu Gln Arg Gln Arg Asn Leu
            100                 105                 110

Leu Gly Glu Asp Leu Gly Pro Leu Asn Ser Lys Glu Leu Glu Gln Leu
            115                 120                 125

Glu Arg Gln Leu Asp Gly Ser Leu Lys Gln Val Arg Ser Ile Lys Thr
        130                 135                 140

Gln Tyr Met Leu Asp Gln Leu Ser Asp Leu Gln Asn Lys Glu Gln Met
145                 150                 155                 160

Leu Leu Glu Thr Asn Arg Ala Leu Ala Met Lys Leu Asp Asp Met Ile
                165                 170                 175

Gly Val Arg Ser His His Met Gly Gly Trp Glu Gly Gly Glu Gln Asn
            180                 185                 190

Val Thr Tyr Ala His His Gln Ala Gln Ser Gln Gly Leu Tyr Gln Pro
        195                 200                 205

Leu Glu Cys Asn Pro Thr Leu Gln Met Gly Tyr Asp Asn Pro Val Cys
    210                 215                 220

Ser Glu Gln Ile Thr Ala Thr Thr Gln Ala Gln Ala Gln Pro Gly Asn
225                 230                 235                 240

Gly Tyr Ile Pro Gly Trp Met Leu
                245
```

<210> SEQ ID NO 6
<211> LENGTH: 1349
<212> TYPE: DNA
<213> ORGANISM: Arabidopsis thaliana
<220> FEATURE:
<223> OTHER INFORMATION: AGL4 cDNA
<220> FEATURE:
<221> NAME/KEY: CDS
<222> LOCATION: (339)..(1091)
<223> OTHER INFORMATION: AGAMOUS-LIKE 4 (AGL4)

<400> SEQUENCE: 6

```
gattcacaaa aactttctt cagattcaca atctcatcac aacccttcaa aaagagaaaa      60
gatctaaaga ataaacaaga gccctaatat caaatcacaa ccaaaaaaac caagaaaagc    120
taattaaagt tttctctcta gctattcctc ttcttttctt gttcttgaaa actagggttt    180
acttcaccaa aagataagat cttccccag aaaaagcaat acccaagtca tgtttctgtg    240
tgtctgtata tagataaaac attacatacc ctaataaggt tacacaaata gctataaaag    300
agggaaaata agatagggat ttttgggt gaggaaag atg gga aga gga aga gta    356
                                          Met Gly Arg Gly Arg Val
                                           1               5
```

-continued

| | |
|---|---|
| gag ctc aag agg ata gag aac aaa atc aac aga caa gtg acg ttt gct<br>Glu Leu Lys Arg Ile Glu Asn Lys Ile Asn Arg Gln Val Thr Phe Ala<br>         10                   15                  20 | 404 |
| aaa cgt aga aat ggt ttg ctg aaa aaa gct tat gag ctt tct gtt ctc<br>Lys Arg Arg Asn Gly Leu Leu Lys Lys Ala Tyr Glu Leu Ser Val Leu<br>       25                   30                   35 | 452 |
| tgc gat gct gaa gtc tct ctc atc gtc ttc tcc aac cgt ggc aag ctc<br>Cys Asp Ala Glu Val Ser Leu Ile Val Phe Ser Asn Arg Gly Lys Leu<br>40                   45                   50 | 500 |
| tac gag ttc tgc agc acc tcc aac atg ctc aag aca ctg gaa agg tat<br>Tyr Glu Phe Cys Ser Thr Ser Asn Met Leu Lys Thr Leu Glu Arg Tyr<br>55                   60                  65                   70 | 548 |
| cag aag tgt agc tat ggc tcc att gaa gtc aac aac aaa cct gct aaa<br>Gln Lys Cys Ser Tyr Gly Ser Ile Glu Val Asn Asn Lys Pro Ala Lys<br>               75                   80                 85 | 596 |
| gag ctt gag aac agc tac aga gag tac ttg aag ctg aaa ggt aga tat<br>Glu Leu Glu Asn Ser Tyr Arg Glu Tyr Leu Lys Leu Lys Gly Arg Tyr<br>                90                   95                 100 | 644 |
| gaa aat ctg caa cgt cag cag aga aat ctt ctt gga gag gat ctt gga<br>Glu Asn Leu Gln Arg Gln Gln Arg Asn Leu Leu Gly Glu Asp Leu Gly<br>             105                 110                115 | 692 |
| cct ctg aat tca aag gag cta gag cag ctt gag cgt caa cta gac ggc<br>Pro Leu Asn Ser Lys Glu Leu Glu Gln Leu Glu Arg Gln Leu Asp Gly<br>        120                125                130 | 740 |
| tct ctg aag caa gtt cgc tgc atc aag aca cag tat atg ctt gac cag<br>Ser Leu Lys Gln Val Arg Cys Ile Lys Thr Gln Tyr Met Leu Asp Gln<br>135                  140                145              150 | 788 |
| ctc tct gat ctt caa ggt aag gag cat atc ttg ctt gat gcc aac aga<br>Leu Ser Asp Leu Gln Gly Lys Glu His Ile Leu Leu Asp Ala Asn Arg<br>             155                 160                165 | 836 |
| gct ttg tca atg aag ctg gaa gat atg atc ggc gtg aga cat cac cat<br>Ala Leu Ser Met Lys Leu Glu Asp Met Ile Gly Val Arg His His His<br>        170                175                180 | 884 |
| ata gga gga gga tgg gaa ggt ggt gat caa cag aat att gcc tat gga<br>Ile Gly Gly Gly Trp Glu Gly Gly Asp Gln Gln Asn Ile Ala Tyr Gly<br>185                  190                195 | 932 |
| cat cct cag gct cat tct cag gga cta tac caa tct ctt gaa tgt gat<br>His Pro Gln Ala His Ser Gln Gly Leu Tyr Gln Ser Leu Glu Cys Asp<br>        200                205                210 | 980 |
| ccc act ttg caa att gga tat agc cat cca gtg tgc tca gag caa atg<br>Pro Thr Leu Gln Ile Gly Tyr Ser His Pro Val Cys Ser Glu Gln Met<br>215                  220              225              230 | 1028 |
| gct gtg acg gtg caa ggt cag tcc caa caa gga aac ggc tac atc cct<br>Ala Val Thr Val Gln Gly Gln Ser Gln Gln Gly Asn Gly Tyr Ile Pro<br>             235                 240                245 | 1076 |
| ggc tgg atg ctg tga gcgatacttc ttcccccaat aaagatctta agcaagtact<br>Gly Trp Met Leu<br>        250 | 1131 |
| ggtgggtct tcgtggtgtg atcttagatc ttatgcatat gaataataat gttattgcac | 1191 |
| aagacttttg cttttgtaga cacaagtggc tatagctgta atagccttca acatctctct | 1251 |
| tctgtttcag gatttgtttg tgcctattgt aattgcttat atatgtatgg tttgtataat | 1311 |
| gtgtgaaatg ttaacatcga ccatgtctca tctggtga | 1349 |

<210> SEQ ID NO 7
<211> LENGTH: 250
<212> TYPE: PRT
<213> ORGANISM: Arabidopsis thaliana
<220> FEATURE:
<223> OTHER INFORMATION: AGAMOUS-LIKE 4 (AGL4)

<400> SEQUENCE: 7

```
Met Gly Arg Gly Arg Val Glu Leu Lys Arg Ile Glu Asn Lys Ile Asn
  1               5                  10                  15

Arg Gln Val Thr Phe Ala Lys Arg Arg Asn Gly Leu Leu Lys Lys Ala
             20                  25                  30

Tyr Glu Leu Ser Val Leu Cys Asp Ala Glu Val Ser Leu Ile Val Phe
         35                  40                  45

Ser Asn Arg Gly Lys Leu Tyr Glu Phe Cys Ser Thr Ser Asn Met Leu
 50                  55                  60

Lys Thr Leu Glu Arg Tyr Gln Lys Cys Ser Tyr Gly Ser Ile Glu Val
 65                  70                  75                  80

Asn Asn Lys Pro Ala Lys Glu Leu Glu Asn Ser Tyr Arg Glu Tyr Leu
                 85                  90                  95

Lys Leu Lys Gly Arg Tyr Glu Asn Leu Gln Arg Gln Arg Asn Leu
            100                 105                 110

Leu Gly Glu Asp Leu Gly Pro Leu Asn Ser Lys Glu Leu Glu Gln Leu
            115                 120                 125

Glu Arg Gln Leu Asp Gly Ser Leu Lys Gln Val Arg Cys Ile Lys Thr
        130                 135                 140

Gln Tyr Met Leu Asp Gln Leu Ser Asp Leu Gln Gly Lys Glu His Ile
145                 150                 155                 160

Leu Leu Asp Ala Asn Arg Ala Leu Ser Met Lys Leu Glu Asp Met Ile
                165                 170                 175

Gly Val Arg His His Ile Gly Gly Gly Trp Glu Gly Gly Asp Gln
            180                 185                 190

Gln Asn Ile Ala Tyr Gly His Pro Gln Ala His Ser Gln Gly Leu Tyr
        195                 200                 205

Gln Ser Leu Glu Cys Asp Pro Thr Leu Gln Ile Gly Tyr Ser His Pro
    210                 215                 220

Val Cys Ser Glu Gln Met Ala Val Thr Val Gln Gly Gln Ser Gln Gln
225                 230                 235                 240

Gly Asn Gly Tyr Ile Pro Gly Trp Met Leu
                245                 250
```

<210> SEQ ID NO 8
<211> LENGTH: 827
<212> TYPE: DNA
<213> ORGANISM: Arabidopsis thaliana
<220> FEATURE:
<223> OTHER INFORMATION: AGL9 cDNA
<220> FEATURE:
<221> NAME/KEY: CDS
<222> LOCATION: (10)..(819)
<223> OTHER INFORMATION: AGAMOUS-LIKE 9 (AGL9)

<400> SEQUENCE: 8

```
cccggatcc aaa atg gga aga ggg aga gta gaa ttg aag agg ata gag aac      51
          Lys Met Gly Arg Gly Arg Val Glu Leu Lys Arg Ile Glu Asn
            1               5                  10 aag atc aat agg caa gtg acg ttt gca aag aga agg aat ggt ctt ttg       99
Lys Ile Asn Arg Gln Val Thr Phe Ala Lys Arg Arg Asn Gly Leu Leu
 15                  20                  25                  30 aag aaa gca tac gag ctt tca gtt cta tgt gat gcg gaa gtt gct ctc      147
Lys Lys Ala Tyr Glu Leu Ser Val Leu Cys Asp Ala Glu Val Ala Leu
                 35                  40                  45 atc atc ttc tca aat aga gga aag ctg tac gag ttt tgc agt agt tcg      195
Ile Ile Phe Ser Asn Arg Gly Lys Leu Tyr Glu Phe Cys Ser Ser Ser
         50                  55                  60
```

```
agc atg ctt cgg aca ctg gag agg tac caa aag tgt aac tat gga gca      243
Ser Met Leu Arg Thr Leu Glu Arg Tyr Gln Lys Cys Asn Tyr Gly Ala
        65                  70                  75 cca gaa ccc aat gtg cct tca aga gag gcc tta gca gaa ctt agt agc      291
Pro Glu Pro Asn Val Pro Ser Arg Glu Ala Leu Ala Glu Leu Ser Ser
 80                  85                  90 cag cag gag tat ctc aag ctt aag gag cgt tat gac gcc tta cag aga      339
Gln Gln Glu Tyr Leu Lys Leu Lys Glu Arg Tyr Asp Ala Leu Gln Arg
 95                 100                 105                 110 acc caa agg aat ctg ttg gga gaa gat ctt gga cct cta agt aca aag      387
Thr Gln Arg Asn Leu Leu Gly Glu Asp Leu Gly Pro Leu Ser Thr Lys
                115                 120                 125 gag ctt gag tca ctt gag aga cag ctt gat tct tcc ttg aag cag atc      435
Glu Leu Glu Ser Leu Glu Arg Gln Leu Asp Ser Ser Leu Lys Gln Ile
            130                 135                 140 aga gct ctc agg aca cag ttt atg ctt gac cag ctc aac gat ctt cag      483
Arg Ala Leu Arg Thr Gln Phe Met Leu Asp Gln Leu Asn Asp Leu Gln
        145                 150                 155 agt aag gaa cgc atg ctg act gag aca aat aaa act cta aga cta agg      531
Ser Lys Glu Arg Met Leu Thr Glu Thr Asn Lys Thr Leu Arg Leu Arg
    160                 165                 170 tta gct gat ggg tat cag atg cca ctc cag ctg aac cct aac caa gaa      579
Leu Ala Asp Gly Tyr Gln Met Pro Leu Gln Leu Asn Pro Asn Gln Glu
175                 180                 185                 190 gag gtt gat cac tac ggt cgt cat cat cat caa caa caa caa cac tcc      627
Glu Val Asp His Tyr Gly Arg His His His Gln Gln Gln Gln His Ser
                195                 200                 205 caa gct ttc ttc cag cct ttg gaa tgt gaa ccc att ctt cag atc ggg      675
Gln Ala Phe Phe Gln Pro Leu Glu Cys Glu Pro Ile Leu Gln Ile Gly
            210                 215                 220 tat cag ggg caa caa gat gga atg gga gca gga cca agt gtg aat aat      723
Tyr Gln Gly Gln Gln Asp Gly Met Gly Ala Gly Pro Ser Val Asn Asn
        225                 230                 235 tac atg ttg ggt tgg tta cct tat gac acc aac tct att tga atc ttt      771
Tyr Met Leu Gly Trp Leu Pro Tyr Asp Thr Asn Ser Ile     Ile Phe
    240                 245                 250 ctc act taa tca atc cct ctc ttt ttt ttt ttg aca ttt tta aga tga      819
Leu Thr     Ser Ile Pro Leu Phe Phe Phe Leu Thr Phe Leu Arg
255                 260                 265                 270 tgtttcta                                                              827

<210> SEQ ID NO 9
<211> LENGTH: 251
<212> TYPE: PRT
<213> ORGANISM: Arabidopsis thaliana
<220> FEATURE:
<223> OTHER INFORMATION: AGAMOUS-LIKE 9 (AGL9)

<400> SEQUENCE: 9

Lys Met Gly Arg Gly Arg Val Glu Leu Lys Arg Ile Glu Asn Lys Ile
 1               5                  10                  15

Asn Arg Gln Val Thr Phe Ala Lys Arg Arg Asn Gly Leu Leu Lys Lys
            20                  25                  30

Ala Tyr Glu Leu Ser Val Leu Cys Asp Ala Glu Val Ala Leu Ile Ile
        35                  40                  45

Phe Ser Asn Arg Gly Lys Leu Tyr Glu Phe Cys Ser Ser Ser Ser Met
    50                  55                  60

Leu Arg Thr Leu Glu Arg Tyr Gln Lys Cys Asn Tyr Gly Ala Pro Glu
65                  70                  75                  80
```

```
Pro Asn Val Pro Ser Arg Glu Ala Leu Ala Glu Leu Ser Ser Gln Gln
            85                  90                  95

Glu Tyr Leu Lys Leu Lys Glu Arg Tyr Asp Ala Leu Gln Arg Thr Gln
            100                 105                 110

Arg Asn Leu Leu Gly Glu Asp Leu Gly Pro Leu Ser Thr Lys Glu Leu
            115                 120                 125

Glu Ser Leu Glu Arg Gln Leu Asp Ser Ser Leu Lys Gln Ile Arg Ala
            130                 135                 140

Leu Arg Thr Gln Phe Met Leu Asp Gln Leu Asn Asp Leu Gln Ser Lys
145                 150                 155                 160

Glu Arg Met Leu Thr Glu Thr Asn Lys Thr Leu Arg Leu Arg Leu Ala
            165                 170                 175

Asp Gly Tyr Gln Met Pro Leu Gln Leu Asn Pro Asn Gln Glu Glu Val
            180                 185                 190

Asp His Tyr Gly Arg His His His Gln Gln Gln Gln His Ser Gln Ala
            195                 200                 205

Phe Phe Gln Pro Leu Glu Cys Glu Pro Ile Leu Gln Ile Gly Tyr Gln
            210                 215                 220

Gly Gln Gln Asp Gly Met Gly Ala Gly Pro Ser Val Asn Asn Tyr Met
225                 230                 235                 240

Leu Gly Trp Leu Pro Tyr Asp Thr Asn Ser Ile
            245                 250

<210> SEQ ID NO 10
<211> LENGTH: 4
<212> TYPE: PRT
<213> ORGANISM: Arabidopsis thaliana
<220> FEATURE:
<223> OTHER INFORMATION: AGL9 cDNA peptide

<400> SEQUENCE: 10

Ile Phe Leu Thr
  1

<210> SEQ ID NO 11
<211> LENGTH: 12
<212> TYPE: PRT
<213> ORGANISM: Arabidopsis thaliana
<220> FEATURE:
<223> OTHER INFORMATION: AGL9 cDNA peptide

<400> SEQUENCE: 11

Ser Ile Pro Leu Phe Phe Phe Leu Thr Phe Leu Arg
  1               5                   10

<210> SEQ ID NO 12
<211> LENGTH: 5368
<212> TYPE: DNA
<213> ORGANISM: Arabidopsis thaliana
<220> FEATURE:
<223> OTHER INFORMATION: AP1 promoter

<400> SEQUENCE: 12
gaattccccg atctccata tacatatcat acatatatat agtatactat ctttagactg    60
atttctctat acactatctt ttaacttatg tatcgtttca aaactcagga cgtacatgtt   120
ttaaatttgg ttatataacc acgaccattt caagtatata tgtcatacca taccagattt   180
aatataactt ctatgaagaa atacataaa gttggattaa aatgcaagtg acatcttttt    240
agcataggtt catttggcat agaagaaata tataactaaa aatgaacttt aacttaaata   300
```

```
gattttacta tattacaatt ttttctttt acatggtcta atttatttt ctaaaattag      360
tatgattgtt gttttgatga acaataata ccgtaagcaa tagttgctaa aagatgtcca      420
aatatttata aattacaaag taaatcaaat aaggaagaag acacgtggaa acaccaaat      480
aagagaagaa atggaaaaaa cagaaagaaa ttttttaaca agaaaaatca attagtcctc      540
aaacctgaga tatttaaagt aatcaactaa acaggaaca cttgactaac aaagaaattt       600
gaaatgtggt ccaactttca cttaattata ttgttttctc taaggcttat gcaatatatg      660
ccttaagcaa atgccgaatc tgttttttt tttgttatt ggatattgac tgaaaataag       720
gggttttttc acacttgaag atctcaaaag agaaaactat tacaacggaa attcattgta      780
aaagaagtga ttaagcaaat tgagcaaagg ttttttatgtg gtttatttca ttatatgatt     840
gacatcaaat tgtatatata tggttgtttt atttaacaat atatatggat ataacgtaca     900
aactaaatat gtttgattga cgaaaaaaaa tatatgtatg tttgattaac aacatagcac      960
atattcaact gattttgtc ctgatcatct acaacttaat aagaacacac aacattgaaa     1020
aaatctttga caaaatacta tttttgggtt tgaaattttg aatacttaca attattcttc     1080
tcgatcttcc tctcttttcct taaatcctgc gtacaaatcc gtcgacgcaa tacattacac      1140
agttgtcaat tggttctcag ctctaccaaa aacatctatt gccaaaagaa aggtctattt      1200
gtacttcact gttacagctg agaacattaa atataataag caaatttgat aaaacaaagg      1260
gttctcacct tattccaaaa gaatagtgta aaatagggta atagagaaat gttaataaaa      1320
ggaaattaaa aatagatatt ttggttggtt cagattttgt ttcgtagatc tacagggaaa     1380
tctccgccgt caatgcaaag cgaaggtgac acttgggaa ggaccagtgg tccgtacaat       1440
gttacttacc catttctctt cacgagacgt cgataatcaa attgtttatt ttcatatttt      1500
taagtccgca gttttattaa aaaatcatgg acccgacatt agtacgagat ataccaatga     1560
gaagtcgaca cgcaaatcct aaagaaacca ctgtggtttt tgcaaacaag agaaaccagc      1620
tttagctttt ccctaaaacc actcttaccc aaatctctcc ataaataaag atcccgagac      1680
tcaaacacaa gtctttttat aaaggaagaa gagaaaaact ttcctaattg gttcatacca      1740
aagtctgagc tcttctttat atctctcttg tagtttctta ttggggggtct ttgttttgtt     1800
tggttcttt agagtaagaa gtttcttaaa aaaggatcaa aaatgggaag gggtagggtt       1860
caattgaaga ggatagagaa caagatcaat agacaagtga cattctcgaa aagaagagct      1920
ggtcttttga agaaagctca tgagatctct gttctctgtg atgctgaagt tgctcttgtt      1980
gtcttctccc ataaggggaa actcttcgaa tactccactg attcttggta acttcaacta     2040
attctttact tttaaaaaaa tctttttaatc tgctactta tatagttttt ttccccctta      2100
agttgactac ttgattgcc ctaattattc actactgctt ttgttatata ttttctaggg      2160
cttccatttt tggattttt gattagccag aaaaatgttt aatacaaatt tgtataattt      2220
aaaaatcaaa actttagggc cgtagtgaag tgaaccctag aacacacaga ttataccata     2280
gtaattacct tgatatattg tgcaatattt atcagcatca tatcttcaaa ctcaagagat      2340
atagaagggt atgttaatct ttgaactagg gttttgatcc ctaactcata atgaatcctt      2400
ttgttctcca atagccatgt ctttcgaatt tgcagatcta agctctaatt gatgccatag      2460
taagaaaata agatctgtag ttttcactcg ctcactgagt tcgagtttta aatgaagtgt     2520
cgtttctttt ttcatatata gttgcaactg gattataatt aaaaaatatt atgggacgag      2580
aaaataattt aaaatagata tagataacaa tgtcaaattg agaatttttt attagaaaga      2640
atatttaact tacgagttgt ttttttttcag ctgtaaaaga atatctaatt tgttctcacg     2700
```

```
actgtgtctt catgttttgc aaatctaagc aaagaaaatg tttaaactcg gatcttaaga    2760
ttatgaactc gtaatataaa acactatata gtattaaatt tgaactagtg ttgcttcttt    2820
tgctactttg actttagaaa ttaaaactga aacaaagatg tcaaatctga gtagggagtc    2880
tttgacctct ggggatccat aaaaagaact aactccatcc taaaatcggc ttcttaccga    2940
tggtcaaact tagctccaac aagcaacagc tgttcttctt tttttttttt tttttttttt    3000
tttaagcatt gtccttgttc tgaaaaaaaa taagattggg aaattggcaa gattataata    3060
atttattata atgtgtcgca ctaagaagat tttctgtacc taattgtagc aaaattaaag    3120
aaaccgcagt tagaactcga agctaagagc atagggtcta tgattcatac tgttttgtta    3180
ttataaaggt atcatagaga tcggtacttg atttgttata ggaaatcttg gtttaattgc    3240
ataaaaccat cattagattt atcctaaaat gtgatgatat tttggtcaca tctccatatt    3300
atttatataa taaaatgata attggttgat gataaagcta accctaattc tgtgaaatga    3360
tcagtatgga gaagatactt gaacgctatg agaggtactc ttacgccgaa agacagctta    3420
ttgcacctga gtccgacgtc aatgtatttc aataaatatt tctccttttta atccacatat    3480 atattatatc aatctatttg tagtattgat gaattttatt tgtataaaac ttctggtaca    3540
cagacaaact ggtcgatgga gtataacagg cttaaggcta agattgagct tttggagaga    3600
aaccagaggt acacatttac actcatcaca tttctatcta gaaatcgat cgggttccat    3660 tttaaagtaa gttaaaattc attgatgcta ttgaaattca ggcattatct tggggaagac    3720
ttgcaagcaa tgagccctaa agagcttcag aatctggagc agcagcttga cactgctctt    3780
aagcacatcc gcactagaaa agtattgcct tctgctattt cgttgaacat atctatataa    3840
cttaaacgtt tacaagtgtt attataatgt gaacattgaa atacatatgt gtatgtatca    3900
atatatatat cagtaatcaa tatcaatttg atatgtctat aggttggttc gaatgtatga    3960
gttatgttgt gtattttaag actccatatt acttaaagta atgggttgtt aatgttgatg    4020
tgtgtgtatg cagaaccaac ttatgtacga gtccatcaat gagctccaaa aaaggtatg    4080 taaaacccct atcaaatgta tgtcttatag agaaacgtat aggaaagcta attaacaatc    4140
gtgccgtttc ggaaatgaca ggagaaggcc atacaggagc aaaacagcat gctttctaaa    4200
caggtaacac atgtcatcat ttctctttca tcaacatgtt gtccattgca ttactgttac    4260
cttccactgt tctgctccac acttccagcc aagctatacc tacgatatct tcatatctcc    4320
acttaacttc ggcaccatta ataaaaata gaaaatcttt gcaaatttgt ttgaaatagc    4380
atagatgttg tctattgatt gatataatca ccagcctgta cgtagatatg gtttgtccgt    4440
ttagttttaa ggtgtctctc ggattgaaaa tattttgaaa tcttttgaaa tgtttgtccc    4500
atcattctta cttagctcat atctatgtat atgaatatag acactactcc taattataaa    4560
atgttataat agttcattgc atgagtgcaa ctgtgaaaat aactatttgt aaccattgca    4620
tatatatagt ttcttcactt tgaaattga tgatgataat atggtttgaa ataaatttgc    4680
tggcagatca aggagaggga aaaaattctt agggctcaac aggagcagtg ggatcagcag    4740
aaccaaggcc acaatatgcc tccccctctg ccaccgcagc agcaccaaat ccagcatcct    4800
tacatgctct ctcatcagcc atctcctttt ctcaacatgg ggtaacaaaa aattactaat    4860
cagtcttaat ttaaagcaca tatgttatgc aagctagtta cgttaggtgt tgtaatttca    4920
ttgaagttat agctgttagt gatggttaca tgatgctaga ttttgaaact agaaaacttt    4980 atttttaaaac attattttat taacgtaggt taatgcaatg tcgccaaac gaacaaactt    5040 attagtgtgg aaaaatgtac atggaatggt tgcgaaaagc ctaagtcgac ttttgttgtt    5100
```

-continued

```
gttggtctat gtgtttaagt acaatttttag tttgttagat aaatgaaatt aatatatctt      5160
tgacatttca caatggactg atatttgatt tcctttgtt gtacggtgaa acatatgatt       5220
acatatgcac tttcatatat atcctatgta tgattgtgaa tgcagtggtc tgtatcaaga      5280
agatgatcca atggcaatga ggaggaatga tctcgaactg actcttgaac ccgtttacaa     5340
ctgcaacctt ggctgcttcg ccgcatga                                         5368
```

```
<210> SEQ ID NO 13
<211> LENGTH: 1220
<212> TYPE: DNA
<213> ORGANISM: Arabidopsis thaliana
<220> FEATURE:
<223> OTHER INFORMATION: AP1 cDNA
<220> FEATURE:
<221> NAME/KEY: CDS
<222> LOCATION: (141)..(911)
<223> OTHER INFORMATION: AP1

<400> SEQUENCE: 13
```

```
gaattcggca cgagaacttt cctaattggt tcataccaaa gtctgagctc ttctttatat       60
ctctcttgta gtttcttatt gggggtcttt gttttgtttg gttcttttag agtaagaagt      120
ttcttaaaaa aggatcaaaa atg gga agg ggt agg gtt caa ttg aag agg ata       173
                       Met Gly Arg Gly Arg Val Gln Leu Lys Arg Ile
                         1               5                  10 gag aac aag atc aat aga caa gtg aca ttc tcg aaa aga aga gct ggt         221
Glu Asn Lys Ile Asn Arg Gln Val Thr Phe Ser Lys Arg Arg Ala Gly
             15                  20                  25 ctt ttg aag aaa gct cat gag atc tct gtt ctc tgt gat gct gaa gtt         269
Leu Leu Lys Lys Ala His Glu Ile Ser Val Leu Cys Asp Ala Glu Val
 30                  35                  40 gct ctt gtt gtc ttc tcc cat aag ggg aaa ctc ttc gaa tac tcc act         317
Ala Leu Val Val Phe Ser His Lys Gly Lys Leu Phe Glu Tyr Ser Thr
             45                  50                  55 gat tct tgt atg gag aag ata ctt gaa cgc tat gag agg tac tct tac         365
Asp Ser Cys Met Glu Lys Ile Leu Glu Arg Tyr Glu Arg Tyr Ser Tyr
 60                  65                  70                  75 gcc gaa aga cag ctt att gca cct gag tcc gac gtc aat aca aac tgg         413
Ala Glu Arg Gln Leu Ile Ala Pro Glu Ser Asp Val Asn Thr Asn Trp
                 80                  85                  90 tcg atg gag tat aac agg ctt aag gct aag att gag ctt ttg gag aga         461
Ser Met Glu Tyr Asn Arg Leu Lys Ala Lys Ile Glu Leu Leu Glu Arg
             95                 100                 105 aac cag agg cat tat ctt ggg gaa gac ttg caa gca atg agc cct aaa         509
Asn Gln Arg His Tyr Leu Gly Glu Asp Leu Gln Ala Met Ser Pro Lys
        110                 115                 120 gag ctt cag aat ctg gag cag cag ctt gac act gct ctt aag cac atc         557
Glu Leu Gln Asn Leu Glu Gln Gln Leu Asp Thr Ala Leu Lys His Ile
125                 130                 135 cgc act aga aaa aac caa ctt atg tac gag tcc atc aat gag ctc caa         605
Arg Thr Arg Lys Asn Gln Leu Met Tyr Glu Ser Ile Asn Glu Leu Gln
140                 145                 150                 155 aaa aag gag aag gcc ata cag gag caa aac agc atg ctt tct aaa cag         653
Lys Lys Glu Lys Ala Ile Gln Glu Gln Asn Ser Met Leu Ser Lys Gln
                160                 165                 170 atc aag gag agg gaa aaa att ctt agg gct caa cag gag cag tgg gat         701
Ile Lys Glu Arg Glu Lys Ile Leu Arg Ala Gln Gln Glu Gln Trp Asp
            175                 180                 185 cag cag aac caa ggc cac aat atg cct ccc cct ctg cca ccg cag cag         749
Gln Gln Asn Gln Gly His Asn Met Pro Pro Pro Leu Pro Pro Gln Gln
        190                 195                 200
```

```
cac caa atc cag cat cct tac atg ctc tct cat cag cca tct cct ttt      797
His Gln Ile Gln His Pro Tyr Met Leu Ser His Gln Pro Ser Pro Phe
205             210                 215 ctc aac atg ggt ggt ctg tat caa gaa gat gat cca atg gca atg agg      845
Leu Asn Met Gly Gly Leu Tyr Gln Glu Asp Asp Pro Met Ala Met Arg
220             225                 230                 235 agg aat gat ctc gaa ctg act ctt gaa ccc gtt tac aac tgc aac ctt      893
Arg Asn Asp Leu Glu Leu Thr Leu Glu Pro Val Tyr Asn Cys Asn Leu
                240                 245                 250 ggc tgc ttc gcc gca tga agcatttcca tatatatata tttgtaatcg             941
Gly Cys Phe Ala Ala
                255 tcaacaataa aaacagtttg ccacatacat ataaatagtg gctaggctct tttcatccaa   1001 ttaatatatt ttggcaaatg ttcgatgttc ttatatcatc atatataaat tagcaggctc   1061 ctttcttctt ttgtaatttg ataagtttat ttgcttcaat atggagcaaa attgtaatat   1121 atttgaaggt cagagagaat gaacgtgaac ttaatagaaa aaaaaaaaaa aaaaaaaaa    1181 aaaaaaaaaa aaaaaaccc gacgtagctc gaggaattc                           1220

<210> SEQ ID NO 14
<211> LENGTH: 256
<212> TYPE: PRT
<213> ORGANISM: Arabidopsis thaliana
<220> FEATURE:
<223> OTHER INFORMATION: AP1

<400> SEQUENCE: 14

Met Gly Arg Gly Arg Val Gln Leu Lys Arg Ile Glu Asn Lys Ile Asn
 1               5                  10                  15

Arg Gln Val Thr Phe Ser Lys Arg Arg Ala Gly Leu Leu Lys Lys Ala
                20                  25                  30

His Glu Ile Ser Val Leu Cys Asp Ala Glu Val Ala Leu Val Val Phe
            35                  40                  45

Ser His Lys Gly Lys Leu Phe Glu Tyr Ser Thr Asp Ser Cys Met Glu
        50                  55                  60

Lys Ile Leu Glu Arg Tyr Glu Arg Tyr Ser Tyr Ala Glu Arg Gln Leu
 65                 70                  75                  80

Ile Ala Pro Glu Ser Asp Val Asn Thr Asn Trp Ser Met Glu Tyr Asn
                85                  90                  95

Arg Leu Lys Ala Lys Ile Glu Leu Leu Glu Arg Asn Gln Arg His Tyr
            100                 105                 110

Leu Gly Glu Asp Leu Gln Ala Met Ser Pro Lys Glu Leu Gln Asn Leu
        115                 120                 125

Glu Gln Gln Leu Asp Thr Ala Leu Lys His Ile Arg Thr Arg Lys Asn
    130                 135                 140

Gln Leu Met Tyr Glu Ser Ile Asn Glu Leu Gln Lys Lys Glu Lys Ala
145                 150                 155                 160

Ile Gln Glu Gln Asn Ser Met Leu Ser Lys Gln Ile Lys Glu Arg Glu
                165                 170                 175

Lys Ile Leu Arg Ala Gln Gln Glu Gln Trp Asp Gln Gln Asn Gln Gly
            180                 185                 190

His Asn Met Pro Pro Leu Pro Pro Gln Gln His Gln Ile Gln His
        195                 200                 205

Pro Tyr Met Leu Ser His Gln Pro Ser Pro Phe Leu Asn Met Gly Gly
    210                 215                 220
```

```
Leu Tyr Gln Glu Asp Asp Pro Met Ala Met Arg Arg Asn Asp Leu Glu
225                 230                 235                 240

Leu Thr Leu Glu Pro Val Tyr Asn Cys Asn Leu Gly Cys Phe Ala Ala
                245                 250                 255
```

```
<210> SEQ ID NO 15
<211> LENGTH: 1374
<212> TYPE: DNA
<213> ORGANISM: Arabidopsis thaliana
<220> FEATURE:
<223> OTHER INFORMATION: AGL4 cDNA
<220> FEATURE:
<221> NAME/KEY: CDS
<222> LOCATION: (347)..(1099)
<223> OTHER INFORMATION: AGL4

<400> SEQUENCE: 15
gaattccgga ttcacaaaaa cttttcttca gattcacaat ctcatcacaa cccttcaaaa      60
agagaaaaga tctaaagaat aaacaagagc cctaatatca aatcacaacc aaaaaaaacca   120 aagaaagcta attaaagttt tctctctagc tattcctctt cttttcttgt tcttgaaaac    180
tagggtttac ttcaccaaaa gataagatct ttccccagaa aaagcaatac ccaagtcatg    240
tttctgtgtg tctgtatata gataaaacat tacataccct aataaggtta cacaaatagc    300
tataaaagag ggaaataag ataggattt tttggggtga ggaagatgg gaagaggaag      360 agtagagctc aagaggatag agaacaaaat caacagacaa gtgacgtttg ctaaacgtag   420
aaatggtttg ctgaaaaaag cttatgagct ttctgttctc tgcgatgctg aagtctctct    480
catcgtcttc tccaaccgtg gcaagctcta cgagttctgc agcacctcca acatgctcaa    540
gacactggaa aggtatcaga agtgtagcta tggctccatt gaagtcaaca acaaacctgc    600
taaagagctt gagaacagct acagagagta cttgaagctg aaaggtagat atgaaaatct    660
gcaacgtcag cagagaaatc ttcttggaga ggatcttgga cctctgaatt caaaggagct    720
agagcagctt gagcgtcaac tagacggctc tctgaagcaa gttcgctgca tcaagacaca    780
gtatatgctt gaccagctct ctgatcttca aggtaaggag catatcttgc ttgatgccaa    840
cagagctttg tcaatgaagc tggaagatat gatcggcgtg agacatcacc atataggagg    900
aggatgggaa ggtggtgatc aacagaatat tgcctatgga catcctcagg ctcattctca    960
gggactatac caatctcttg aatgtgatcc cactttgcaa attggatata gccatccagt   1020
gtgctcagag caaatggctg tgacggtgca aggtcagtcc caacaaggaa acggctacat   1080
ccctggctgg atgctgtgag cgatacttct tcccccaata aagatcttaa gcaagtactg   1140
gtggggtctt cgtggtgtga tcttagatct tatgcatatg aataataatg ttattgcaca   1200
agacttttgc ttttgtagac acaagtggct atagctgtaa tagccttcaa catctctctt   1260
ctgtttcagg atttgtttgt gcctattgta attgcttata tatgtatggt ttgtataatg   1320
tgtgaaatgt taacatcgac catgtctcat ctggtgaaaa aaaaaaaaaa aaaa          1374

<210> SEQ ID NO 16
<211> LENGTH: 1303
<212> TYPE: DNA
<213> ORGANISM: Arabidopsis thaliana
<220> FEATURE:
<223> OTHER INFORMATION: AGL2 cDNA
<220> FEATURE:
<221> NAME/KEY: CDS
<222> LOCATION: (396)..(1142)
<223> OTHER INFORMATION: AGL2
```

```
<400> SEQUENCE: 16
gaattccggc cctcacacat ttcttatctt ttgctctcaa tagattccat tgattcaaaa      60
caaaattttc attaagattt cacaacctcc acacacttcc aaacacaatt aaagagagga     120
aaaagaatca ataaccctat aaataaaaaa tcagacaaac agaagtttcc tcttcttctt     180
ccttaagcta gtacctttg ttcttgaaat tagggttaat ttcttttttc caaataccat      240
caattctcca gaccataaaa actcaaaaag atcagatctt tcctctgaaa aagagatacc     300
caacttatgt ttttgtgtgt ctgtatatag ataaacatta catacccata tttgtgtata     360
gacataaaaa gtggaaatta aggtaacaaa aagaaatggg aagaggaaga gtagagctga     420
agaggataga gaacaaaatc aacagacaag taacgtttgc aaagcgtagg aacggtttgt     480
tgaagaaagc ttatgaattg tctgttctct gtgatgctga agttgctctc atcatcttct     540
ccaaccgtgg aaagctctat gagttttgca gctcctcaaa catgctcaag acacttgatc     600
ggtaccagaa atgcagctat ggatccattg aagtcaacaa caaacctgcc aaagaacttg     660
agaacagcta cagagaatat ctgaagctta agggtagata tgagaacctt caacgtcaac     720
agagaaatct tcttggggag gatttaggac ctttgaattc aaaggagtta gagcagcttg     780
agcgtcaact ggacggctct ctcaagcaag ttcggtccat caagacacag tacatgcttg     840
accagctctc ggatcttcaa aataaagagc aaatgttgct tgaaaccaat agagctttgg     900
caatgaagct ggatgatatg attggtgtga gaagtcatca tatgggagga tgggaaggcg     960
gtgaacagaa tgttacctac gcgcatcatc aagctcagtc tcaggacta taccagcctc    1020 ttgaatgcaa tccaactctg caaatggggt atgataatcc agtatgctct gagcaaatca    1080
ctgcgacaac acaagctcag gcgcagccgg gaaacggtta cattccagga tggatgctct    1140
gagaatcatg tactgtgatg aagctcaccc acaaaagacc ttatatatat ataaagtata    1200
gatacaagac ttggatttgt agacataagt ggctaatata atggtcctga ggatcttcta    1260
gacatttgta tcttttggga atccttgctt atattaagaa ttc                     1303

<210> SEQ ID NO 17
<211> LENGTH: 30
<212> TYPE: DNA
<213> ORGANISM: Artificial Sequence
<220> FEATURE:
<223> OTHER INFORMATION: Description of Artificial Sequence:forward
      primer AP1HIN

<400> SEQUENCE: 17
caagcttgta cacatttaca ctcatcacat                                       30

<210> SEQ ID NO 18
<211> LENGTH: 28
<212> TYPE: DNA
<213> ORGANISM: Artificial Sequence
<220> FEATURE:
<223> OTHER INFORMATION: Description of Artificial Sequence:reverse
      primer AP1BAM

<400> SEQUENCE: 18
cggatcctgc gcgaagcagc caaggttg                                         28
```

What is claimed is:

1. A transgenic plant characterized by suppressed flowering, comprising a nucleic acid molecule comprising a floral organ selective regulatory element that comprises nucleotides 292-851 of SEQ ID NO:2, operatively linked to a nucleotide sequence encoding a cytotoxic gene product, wherein said nucleic acid molecule is heritable by progeny thereof.

2. The transgenic plant of claim 1, wherein said cytotoxic gene product is selected from the group consisting of diphtheria toxic A chain, RNase T1, Barnase Rnase, ricin toxin A chain, and herpes simplex virus thymidine kinase (tk) gene.

3. A tissue derived from the transgenic plant of any of claims 1, or 2.

4. The tissue of claim 3, which is capable of non-vegetative propagation.

5. The tissue of claim 3, which is capable of vegetative propagation.

6. The plant of claim 1, wherein said plant is a woody plant.

7. The plant of claim 6, wherein said plant is a tree.

8. A method of producing a transgenic plant characterized by suppressed flowering, comprising introducing into a plant an exogenous nucleic acid molecule comprising a floral organ selective regulatory element, wherein said regulatory element comprises nucleotides 292-851 of SEQ ID NO:2, wherein the regulatory element is operatively linked to a nucleotide sequence encoding a cytotoxic gene product, whereby flowering is suppressed due to selective expression of said exogenous nucleic acid molecule in said floral organ, and wherein said nucleic acid molecule is heritable by progeny thereof.

9. The method of claim 8, wherein said cytotoxic gene product is selected from the group consisting of diphtheria toxic A chain, RNase T1, Barnase Rnase, ricin toxin A chain, and herpes simplex virus thymidine kinase (tk) gene.

10. The method of claim 8, wherein the nucleic acid molecule is introduced into the plant by *Agrobacterium*-mediated transformation.

11. The method of claim 10, wherein *Agrobacterium tumefaciens* is used to introduce the nucleic acid molecule into the plant.

12. The method of claim 10, wherein *Agrobacterium rhizogenes* is used to introduce the nucleic acid molecule into the plant.

13. The transgenic plant of claim 1, wherein said plant is obtainable by a process comprising the steps of (i) introducing into a plant an exogenous nucleic acid molecule comprising the floral organ selective regulatory element, wherein said regulatory element is operatively linked to a nucleotide sequence encoding a cytotoxic gene product; (ii) identifying or selecting a population of plants whose flowering is suppressed; (iii) generating a progeny transgenic plant therefrom.

14. An isolated nucleic acid molecule, comprising a floral organ selective regulatory element that comprises nucleotides 292-851 of SEQ ID NO:2, operatively linked to a nucleotide sequence encoding a cytotoxic gene product.

15. The isolated nucleic acid molecule of claim 14, wherein said cytotoxic gene product is selected from the group consisting of diphtheria toxic A chain, RNase T1, Barnase Rnase, ricin toxin A chain, and herpes simplex virus thymidine kinase (tk) gene.

16. A kit for producing a transgenic plant characterized by suppressed flowering, comprising packaging containing a plant expression vector comprising a floral organ selective regulatory element that comprises nucleotides 292-851 of SEQ ID NO:2, wherein the regulatory element is operatively linked to a nucleotide sequence encoding a cytotoxic gene product, and instructions for transforming a susceptible plant with said vector.

17. The kit of claim 16, wherein said cytotoxic gene product is selected from the group consisting of diphtheria toxic A chain, RNase T1, Barnase Rnase, ricin toxin A chain, and herpes simplex virus thymidine kinase (tk) gene.

* * * * *